US005734016A

United States Patent [19]
Levens et al.

[11] Patent Number: 5,734,016
[45] Date of Patent: Mar. 31, 1998

[54] FUSE BINDING PROTEIN AND METHOD FOR INHIBITING EXPRESSION OF FUSE BINDING PROTEIN

[75] Inventors: David L. Levens, Bethesda; Robert C. Duncan, Mt. Rainer; Mark I. Avigan, Silver Spring, all of Md.

[73] Assignee: The United States of America as represented by the Secretary of the Department of Health and Human Services, Washington, D.C.

[21] Appl. No.: 726,160

[22] Filed: Oct. 4, 1996

Related U.S. Application Data

[63] Continuation of Ser. No. 21,608, Feb. 22, 1993, Pat. No. 5,580,760.

[51] Int. Cl.$^6$ ............................................. C07K 14/00
[52] U.S. Cl. .................................. 530/324; 530/350
[58] Field of Search .......................... 435/91.2, 240.2, 435/320.1, 325; 536/23.1, 24.31, 23.5, 24.5; 530/350, 300, 324; 514/44

[56] References Cited

U.S. PATENT DOCUMENTS 5,580,760  12/1996  Levens et al. ...................... 435/91.2
5,585,479  12/1996  Hoke et al. ......................... 536/24.5

OTHER PUBLICATIONS

Avigan, M.I., et al."A Far Upstream Element Stimulates c–myc Expression in Undifferentiated Leukemia Cells," *J. Biol. Chem.*, 265, 18538–18545 (1990).

Sigma Molecular Biology, published by Sigma Chemical Company St. Louis, MO; 51–52 (1989).

Avigan, M.I., et al. "Cloning of the cellular factor which binds the far upstream element (FUSE) of the c–myc gene," *J. Cell. Biochem.*, vol. 50, Suppl. 0 (16 part A), 1992, p. 83, abstract No. B 211, which is an abstract of an oral presentation given at the Keystone Symposium on Transcription Regulation, Tamorron, Colorado, USA, Jan. 13–20, 1992.

Duncan, R., et al. "The human c–myc FUSE element binds a differentiation regulated protein with a novel structure," *Biomed. Pharmacother.*, vol. 46, 5–7 (1992), p. 243, abstract No. 11, which is an abstract of an oral presentation given at the 5th International Congress on Differentiation Therapy, Villasimius, Italy, 2–5 Sep., 1992.

Barinaga, M. 1994 Science vol. 266, p. 1326.

Marshall, E.M. 1995 Science vol. 269, pp. 1050–1055.

Crystal, R. 1995 Science vol. 270, pp. 404–410.

Jolly, D. 1994 Cancer Gene Therapy vol. 1(1) pp. 51–64.

Orkin et al. Dec. 1995 Report and Recommendations of the Panel to Assess the NIH Investment in Research on Gene Therapy.

Roush, W. Science May 23, 1997 vol. 276, pp. 1192–1193.

Gura, T. 1995 Science vol. 270, pp. 575–577.

Wagner, R.W. 1994 Nature, vol. 372, pp. 333–335.

*Primary Examiner*—James Ketter
*Assistant Examiner*—Ivan Yucel
*Attorney, Agent, or Firm*—Morgan & Finnegan

[57] ABSTRACT

The Far Upstream Element (FUSE) of the human c–myc gene stimulates expression in undifferentiated cells. A FUSE binding protein (FBP), also referred to as DROME (DNA-binding regulator of c–myc expression), is active in undifferentiated but not differentiated cell extracts. Cloned FBP exhibits the same DNA-binding specificity as the purified human protein and can trans-activate in a FUSE dependent manner. Sequence-specific binding to the FUSE oligonucleotide requires at least two copies of a repeat-helix unit which defines a new DNA-binding motif. Expression of FBP mRNA declined in parallel with decreased FUSE binding activity upon differentiation suggesting transcriptional regulation of FBP.

30 Claims, 9 Drawing Sheets

```
1   V P D G M V G F I I G R G G E Q I S R I Q Q E S G C K I Q I
2   I P A S K A G L V I G K G G E T I K Q L Q E R A G V K M V M
3   I P R F A V G I V I G R N G E M I K K I Q N D A G V R I Q F
4   V P T G K T G L I I G K G G E T I K S I S Q Q S G A R I E L
```

FUSE BINDING PROTEIN AND METHOD FOR INHIBITING EXPRESSION OF FUSE BINDING PROTEIN

This application is a continuation of application Ser. No. 08/021,608, filed Feb. 22, 1993 now U.S. Pat. No. 5,580,760.

FILED OF THE INVENTION

The present invention relates to a novel human cDNA and the encoded protein which interacts with a cis-element activator, known as the FUSE binding protein. A novel DNA-binding regulator of c-myc expression ("DROME") was purified, and then proteolytically and chemically degraded to peptides. These peptides were separated by HPLC and the sequences of multiple peptides were determined. Using the information from the peptide sequence, specific oligonucleotide primers were synthesized and then used as primers for the polymerase chain reaction employing human cDNA as a template. The resulting products were cloned and sequenced, and shown to encode additional peptides of the DROME protein. These DNA segments were then employed as probes to screen multiple phage libraries in order to reconstruct a full length reading frame from several overlapping clones. This information allows the expression of a full length protein. As used herein, the terms DROME and FUSE binding protein ("FBP") are synonymous.

BACKGROUND OF THE INVENTION

The c-myc proto-oncogene plays a central role in normal cell proliferation and programmed cell death (Y. Shi, J. Glynn, L. Guilbert, T. Cotter, R. Bissonnette, and D. Green, "Role for c-myc in activation-induced apoptotic cell death in T cell hybridomas," Science, 257:212–214 (1992)) and its deregulation contributes to the formation of a variety of tumors. (J. M. Bishop, Annu. Rev. Biochem. 52,301–354 (1983); M. D. Cole, "The myc oncogene: its role in transformation and differentiation." Annu. Rev. Genet. 20, 361–384 (1986); S. Cory, Adv. Cancer Res. 47, 189–234 (1986)).

Down regulation of the c-myc proto-oncogene occurs in the human promonomyelocytic leukemia cell line HL60 and human monoblastic line, U937, upon induction of differentiation. (C. Dony, M. Kessel, and P. Gruss, Nature. 317, 636–639 (1985); L. E. Grosso, and H. C. Pitot, Cancer Res. 45, 847–850 (1985); T. Watanabe, E. Sariban, T. Mitchell, and D. Kufe, Biochem. Biophys. Res. Commun. 126, 999–1005 (1985); D. L. Bentley, and M. Groudine, Nature, 321, 702–706 (1986); D. Eick and G. W. Bornkamm, Nucleic Acids Res. 14, 8331–8346 (1986); T. Endo, and B. Nadal-Ginard, Mol. Cell. Biol. 6, 1412–1421 (1986)). This suppression of c-myc expression occurs by two mechanisms; within three hours there is a block to elongation which can be reversed by removal of the differentiation agent. Subsequently, transcriptional initiation ceases, coinciding with irreversible commitment to the differentiation pathway. (U. Siebenlist, P. Bressler, and K. Kelly, Mol. Cel. Biol. 8, 867–874 (1988)).

A Far Upstream Element ("FUSE") which is required for maximal transcription of c-myc, binds a factor (DROME or FUSE binding protein ("FBP")) which is present in extracts of undifferentiated cells, but disappears upon differentiation. (M. I. Avigan, B. Strober, and D. Levens, "A Far Upstream Element Stimulates c-myc Expression In Undifferentiated Leukemia Cells." J. Biol. Chem. 265, 18538–18545 (1990)). The disappearance of this binding activity occurs 24 hours after addition of the differentiation agent coinciding with the loss of initiation of c-myc transcription. The FUSE site differs from other described positive regulatory elements for myc in a number of ways. Despite its placement a long distance from the transcription start site (−1500 bp relative to the myc P1 promoter), the FUSE element will not act as a traditional enhancer; multiple copies inserted upstream of a heterologous promoter do not stimulate transcription in transection experiments. However, when the FUSE site is present with additional c-myc regulatory sequences, specific stimulation of the c-myc promoter is observed, indicating that FUSE works in concert with other myc elements. These features suggest that the factor binding to this site may act to stimulate transcription by an unusual mechanism.

SUMMARY OF THE INVENTION

The nucleotide sequence for a novel DNA-binding regulator of c-myc expression is provided, together with the amino acid sequence for the encoded protein. The protein interacts with an activator cis-element approximately 1500 basepairs 5' of the human c-myc gene promoter P1. The cDNA and variations thereof have the nucleotide sequences of SEQ ID NO:1, SEQ ID NO:5, SEQ ID NO:7 and SEQ ID NO:9, and the proteins have the amino acid sequences of SEQ ID NO:2, SEQ ID NO:6, SEQ ID NO:8 and SEQ ID NO:10.

With the given sequence for the cDNA and protein of the present invention, one may now study genetic abnormalities of c-myc expression, in addition to numerous other uses of the gene and encoded protein.

The gene encoding the DROME or FUSE binding protein is useful in the diagnosis of disease states. Specific nucleic acid probes derived from knowledge of the DROME sequence and genetic map for PCR or hybridization are useful to analyze mutations, translocations and other genetic derangements that are associated with abnormalities of DROME or c-myc expression. Because DROME is highly activated during T-cell stimulation, these probes are useful to analyze immune system abnormalities. The DROME probes are also useful to analyze a variety of physiologic and pathologic conditions.

Knowledge of the cDNA and genomic structures of DROME allows the construction of vectors which express DROME or which express anti-sense DROME sequence. Oligonucleotide and expression vector anti-sense approaches to block DROME expression are useful to modulate DROME expression in vivo, which results in therapeutic modification of the levels of expression of genes regulated by DROME. Such strategies are of therapeutic value to certain pathologic conditions or can be used to provide prophylactic or beneficial changes in DROME expression in pre-pathologic conditions. If genetic disorders can be ascribed to abnormalities of the DROME protein or its expression, then gene therapy for such disorders will be heavily dependent on the information and materials derived from the characterization of the DROME gene and its cDNA.

Expression of the DROME protein itself in prokaryotic and eukaryotic expression vectors is useful in several regards. The DROME protein or fragments thereof are useful as an immunogen to generate polyclonal and monoclonal antibodies which can then be used to detect and quantitate the DROME protein. The DROME protein itself is useful as a probe to identify and quantify proteins which interact with or modify DROME; similarly, if the DROME protein is immobilized as a ligand for larger scale operations, the DROME interacting or modifying molecules can be purified. All of these proteins can be employed singly or in combination together with existing technologies as assay kits to detect, quantitate and analyze DROME protein.

Structural analysis of the DROME protein has defined a new DNA binding motif composed of a unique repeating element followed by an amphipathic helix. Knowledge of these structural elements together with knowledge of the complete cDNA sequence permits the identification, cloning and characterization of the genes for related proteins and DROME homologs using hybridization based or PCR based methods.

Because proteins which share structural motifs often share biochemical properties as well as functional and physiological roles, it is expected that DROME homologs and other proteins with the newly defined DNA binding motif are also important regulators of cell growth and other cellular processes. The same approaches used to modify DROME expression by sense and anti-sense vectors and anti-sense oligonucleotides is applied to DROME homologs and proteins sharing the DROME DNA binding motif in order to alter cell growth and cellular properties. These proteins or fragments thereof, which are either DROME homologs or recognizable as DNA binding proteins because they possess the DNA binding motif described herein, are useful for the generation of antibodies and diagnostic kits to relate these molecules to cancer, genetic and other human maladies. These proteins, antibodies and kits are useful in the diagnosis, treatment and study of human diseases.

Similarly, altered forms of the protein, either due to post-translational modification or altered RNA processing resulting from altered splicing or other RNA modifications, are identified and characterized utilizing the protein, antibody and nucleic acid probes outlined above. Each of these new proteins and/or genes all related to DROME are then subjected to similar analyses.

DETAILED DESCRIPTION OF THE INVENTION

A 70 kilodalton (kd) FUSE binding protein (FBP) has been purified from undifferentiated HL60 cells, the protein eluted from an SDS acrylamide gel and the amino acid sequence of internal peptides determined. The peptide sequences enabled the design of oligonucleotide PCR primers used to amplify cDNA template prepared from undifferentiated U937 cell total RNA.

Reverse transcriptase-polymerase chain reaction (RT-PCR) was performed as described in D. Rappolee, A. Wang, D. Mark, and Z. Werb, *J. Cell. Biochem.* 39,1 (1989). In the RT step 5 µg total U937 RNA, 1.5 µg of random hexamer primers (Promega) and 20 µMoles of each deoxynucleotide triphosphate (dNTP) were incubated in a 40 µl reaction with Superscript Reverse Transcriptase (BRL) and the manufacturer's reaction buffer adjusted to 10 mM dithiothreitol at 45° C. for 1 hour. After ethanol precipitation and reconstitution in 40 µl dH$_2$O, 2 µl of the RT reaction products were used as template in a 50 µl PCR reaction with 20 pMoles of each degenerate primer, 20 nMoles each dNTP, 1.5 units Amplitaq polymerase (Perkin Elmer Cetus) and the manufacturer's buffer adjusted to 7.5 mM MgCL$_2$. Samples were incubated through 25 cycles of 94° C., 55° C., and 72° C., 2 minutes at each temperature.

Two amplified products contained open reading frames encoding segments identical to peptide sequences from purified FBP confirming that the authentic cDNA had been obtained.

Figure 1A:
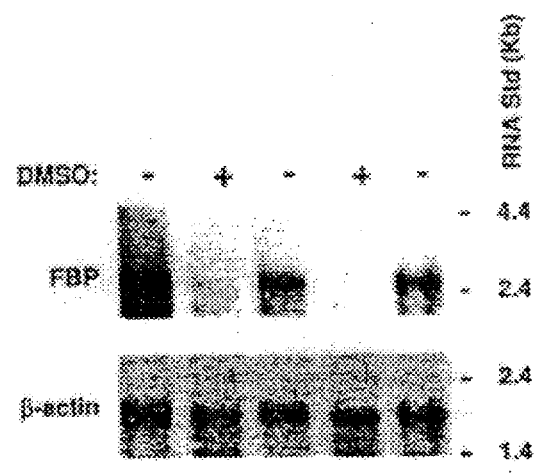
FIGS. 1A and 1B depict radiographs showing reduced expression over time of FBP mRNA.
Figure 1B:
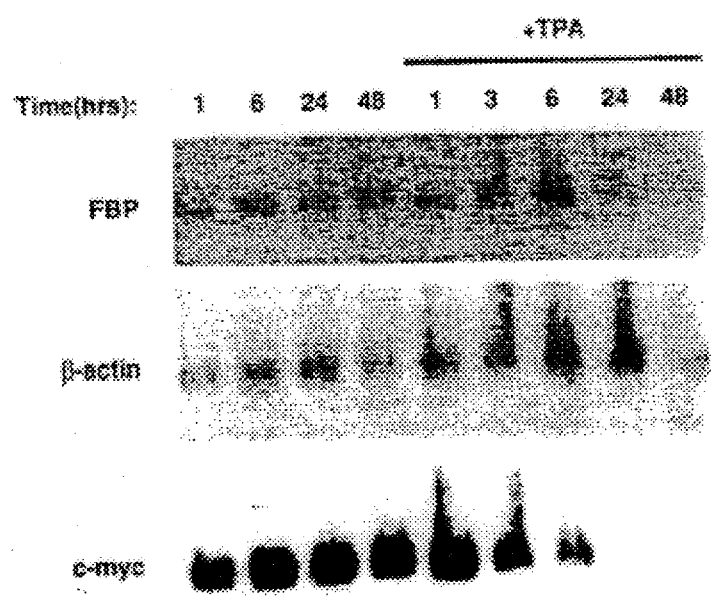

The PCR fragments hybridized to a single 2.6 kilobase (kb) RNA which disappeared after DMSO induced differentiation (FIG. 1A) consistent with the loss of FUSE binding activity after DMSO treatment. Polyadenylated RNA (10 µg) from cultured cells (J. M. Chirgwin et al., Biochemistry, 18, 5294 (1979)) was separated on a 1% agarose-formaldehyde gel, transferred to nitrocellulose and hybridized with a $^{32}$P probe from FBP, B-actin, or human c-myc cDNAs. FIG. 1A shows RNA prepared from HL60 cells grown 48 hrs. in the presence (+) or absence (−) of 1.3% Dimethyl Sulfoxide (DMSO) in RPMI medium supplemented with 10% fetal calf serum, glutamine, penicillin and streptomycin. FIG. 1B shows RNA prepared from HL60 cells cultured as indicated with or without 50 ng/ml 12-o-tetradecanohlphorbol 13-acetate (TPA) in the same medium as above.

As depicted in FIG. 1B, expression of the 2.6 kb transcript sharply declined after 24 hours of treatment with TPA and was undetectable at 48 hours paralleling: 1) the disappearance of the FUSE binding activity, 2) a dramatic decrease in c-myc transcriptional initiation and, 3) irreversible commitment to terminal differentiation. Hence, FBP mRNA and binding activity are shut off synchronously during differentiation.

A full length FBP cDNA sequence was assembled from overlapping clones obtained from three libraries using the PCR fragments as probes. All three cDNA libraries were prepared from poly A selected RNA and ligated into the lambda Zap II vector (Stratagene). Source RNAs were from undifferentiated HL60 cells, the B lymphoma cell line, BJAB, and PMA/PHA stimulated pooled human peripheral blood lymphocytes (PBLs).

Figure 2:
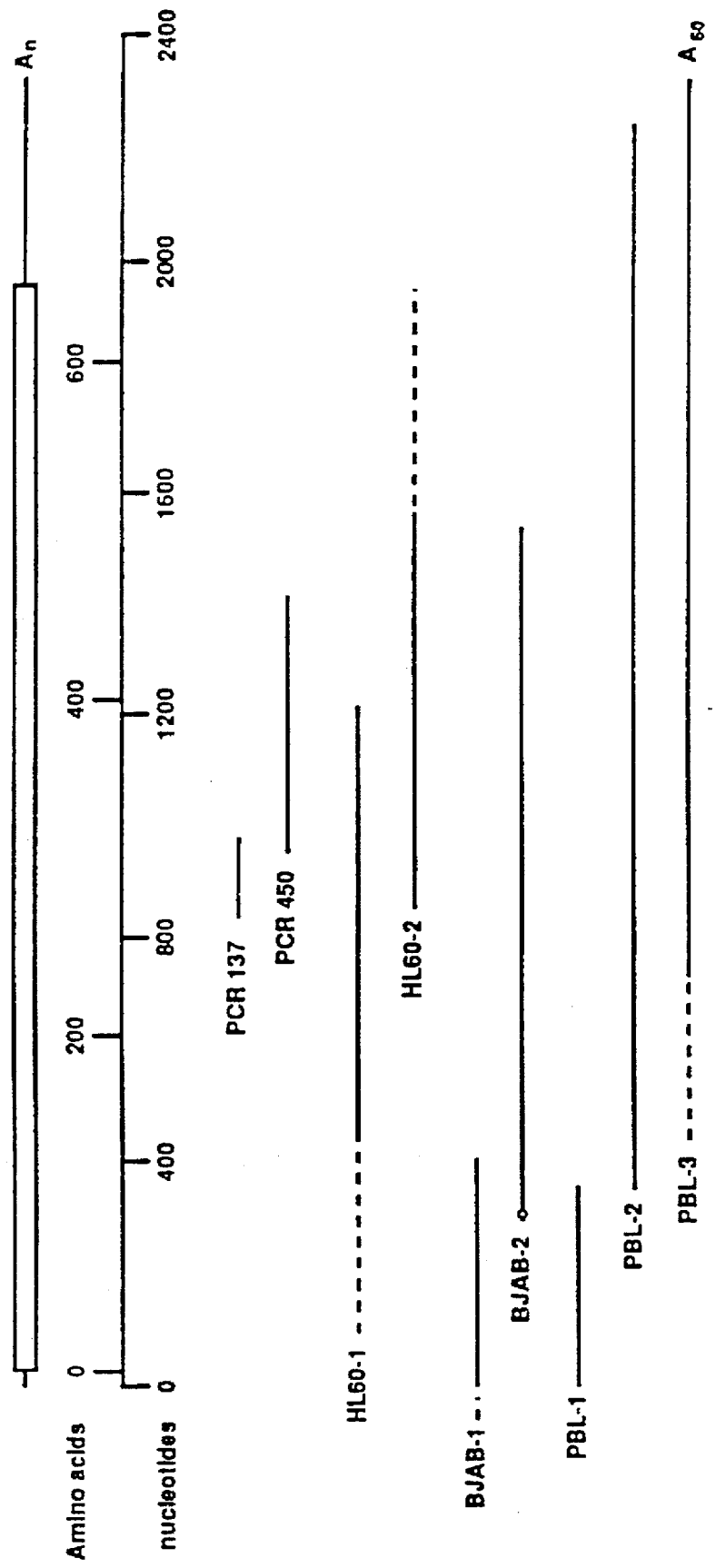
FIG. 2 gives the primary structure of DROME or FUSE binding protein (FBP) cDNA sequences.

The composite 2,384 bp cDNA contains 26 bp of 5' untranslated sequence, 1932 bp of open reading frame, and 426 bp of 3' untranslated including a poly A addition signal and 60 bp of poly A tail, as shown in FIG. 2.

The open box (FIG. 2) in the composite cDNA indicates the coding region, $A_n$ the poly A tail. The position of PCR products and clones are shown, solid lines represent vertically aligned identical sequence, dashed lines represent non-homologous sequence. Clone names at left indicate source or library of origin. The nonhomologous sequences in the HL60 clones, BJAB-1, and PBL-3 most likely are from reverse transcribed, unspliced pre-mRNA or extraneous cDNA fragments ligated together during the preparation of the libraries. The open circle on clone BJAB-2 indicates the position of the 3 base pair deletion. Dideoxy sequencing (Sequenase, U.S. Biochemical) followed the manufacturer's protocol.

The nucleic acid sequence (SEQ ID NO:1) of the full length cDNA is as follows:

| | | | | | | | | | | | | |
|---|---|---|---|---|---|---|---|---|---|---|---|---|
| GCGGCAGCGG CTCTTATAGT GCAACC | | | | | | ATG | GCA | GAC | TAT | TCA | ACA | 44 |
| CGCCGTCGCC GAGAATATCA CGTTGG | | | | | | TAC | CGT | CTG | ATA | AGT | TGT | |
| | | | Met<br>1 | | | Ala | Asp | Tyr | Ser | Ser<br>5 | Thr | |
| GTG | CCT | CCC | CCC | TCT | TCT | GGC | TCA | GCT | GGT | GGC | GGT | GGT | 83 |
| CAC | GGA | GGG | GGG | AGA | AGA | CCG | AGT | CGA | CCA | CCG | CCA | CCA | |
| Val | Pro | Pro | Pro<br>10 | Ser | Ser | Gly | Ser | Ala<br>15 | Gly | Gly | Gly | Gly | |
| GGC | GGC | GGT | GGT | GGT | GGA | GGA | GTT | AAC | GAC | GCT | TTC | AAA | 122 |
| CCG | CCG | CCA | CCA | CCA | CCT | CCT | CAA | TTG | CTG | CGA | AAG | TTT | |
| Gly<br>20 | Gly | Gly | Gly | Gly | Gly<br>25 | Gly | Val | Asn | Asp | Ala<br>30 | Phe | Lys | |
| GAT | GCA | CTG | CAG | AGA | GCC | CGG | CAG | ATT | GCA | GCA | AAA | ATT | 161 |
| CTA | CGT | GAC | GTC | TCT | CGG | GCC | GTC | TAA | CGT | CGT | TTT | TAA | |
| Asp | Ala | Leu<br>35 | Gln | Arg | Ala | Arg | Gln<br>40 | Ile | Ala | Ala | Lys | Ile<br>45 | |
| GGA | GGT | GAT | GCA | GGG | ACA | TCA | CTG | AAT | TCA | AAT | GAC | TAT | 200 |
| CCT | CCA | CTA | CGT | CCC | TGT | AGT | GAC | TTA | AGT | TTA | CTG | ATA | |
| Gly | Gly | Asp | Ala | Gly<br>50 | Thr | Ser | Leu | Asn | Ser<br>55 | Asn | Asp | Tyr | |
| GGT | TAT | GGG | GGA | CAA | AAA | AGA | CCT | TTA | GAA | GAT | GGA | GAT | 239 |
| CCA | ATA | CCC | CCT | GTT | TTT | TCT | GGA | AAT | CTT | CTA | CCT | CTA | |
| Gly | Tyr<br>60 | Gly | Gly | Gln | Lys | Arg<br>65 | Pro | Leu | Glu | Asp | Gly<br>70 | Asp | |
| CAA | CCA | GAT | GCT | AAG | AAA | GTT | GCT | CCT | CAA | AAT | GAC | TCT | 278 |
| GTT | GGT | CTA | CGA | TTC | TTT | CAA | CGA | GGA | GTT | TTA | CTG | AGA | |
| Gln | Pro | Asp | Ala<br>75 | Lys | Lys | Val | Ala | Pro<br>80 | Gln | Asn | Asp | Ser | |
| TTT | GGA | ACA | CAG | TTA | CCA | CCG | ATG | CAT | CAG | CAG | CAA | AGC | 317 |
| AAA | CCT | TGT | GTC | AAT | GGT | GGC | TAC | GTA | GTC | GTC | GTT | TCG | |
| Phe<br>85 | Gly | Thr | Gln | Leu | Pro<br>90 | Pro | Met | His | Gln | Gln<br>95 | Gln | Ser | |
| AGA | TCT | GTA | ATG | ACA | GAA | GAA | TAC | AAA | GTT | CCA | GAT | GGA | 356 |
| TCT | AGA | CAT | TAC | TGT | CTT | CTT | ATG | TTT | CAA | GGT | CTA | CCT | |
| Arg | Ser | Val<br>100 | Met | Thr | Glu | Glu | Tyr<br>105 | Lys | Val | Pro | Asp | Gly<br>110 | |
| ATG | GTT | GGA | TTC | ATA | ATT | GGC | AGA | GGA | GGT | GAA | CAG | ATC | 395 |
| TAC | CAA | CCT | AAG | TAT | TAA | CCG | TCT | CCT | CCA | CTT | GTC | TAG | |
| Met | Val | Gly | Phe | Ile<br>115 | Ile | Gly | Arg | Gly | Gly<br>120 | Glu | Gln | Ile | |
| TCA | CGC | ATA | CAA | CAG | GAA | TCT | GGA | TGC | AAA | ATA | CAG | ATA | 434 |
| AGT | GCG | TAT | GTT | GTC | CTT | AGA | CCT | ACG | TTT | TAT | GTC | TAT | |
| Ser | Arg<br>125 | Ile | Gln | Gln | Glu | Ser<br>130 | Gly | Cys | Lys | Ile | Gln<br>135 | Ile | |
| GCT | CCT | GAC | AGT | GGT | GGC | CTT | CCA | GAA | AGG | TCC | TGT | ATG | 473 |
| CGA | GGA | CTG | TCA | CCA | CCG | GAA | GGT | CTT | TCC | AGG | ACA | TAC | |
| Ala | Pro | Asp | Ser<br>140 | Gly | Gly | Leu | Pro | Glu<br>145 | Arg | Ser | Cys | Met | |
| TTA | ACT | GGA | ACA | CCT | GAA | TCT | GTC | CAG | TCA | GCA | AAA | CGG | 512 |
| AAT | TGA | CCT | TGT | GGA | CTT | AGA | CAG | GTC | AGT | CGT | TTT | GCC | |
| Leu<br>150 | Thr | Gly | Thr | Pro | Glu<br>155 | Ser | Val | Gln | Ser | Ala<br>160 | Lys | Arg | |
| TTA | CTG | GAC | CAG | ATT | GTT | GAA | AAA | GGA | AGA | CCA | GCT | CCT | 551 |
| AAT | GAC | CTG | GTC | TAA | CAA | CTT | TTT | CCT | TCT | GGT | CGA | GGA | |
| Leu | Leu | Asp<br>165 | Gln | Ile | Val | Glu | Lys<br>170 | Gly | Arg | Pro | Ala | Pro<br>175 | |
| GGC | TTC | CAT | CAT | GGC | GAT | GGA | CCG | GGA | AAT | GCA | GTT | CAA | 590 |
| CCG | AAG | GTA | GTA | CCG | CTA | CCT | GGC | CCT | TTA | CGT | CAA | GTT | |
| Gly | Phe | His | His<br>180 | Gly | Asp | Gly | Pro | Gly<br>185 | Asn | Ala | Val | Gln | |
| GAA | ATC | ATG | ATT | CCA | GCT | AGC | AAG | GCA | GGA | TTA | GTC | ATT | 629 |
| CTT | TAG | TAC | TAA | GGT | CGA | TCG | TTC | CGT | CCT | AAT | CAG | TAA | |
| Glu | Ile<br>190 | Met | Ile | Pro | Ala<br>195 | Ser | Lys | Ala | Gly<br>200 | Leu | Val | Ile | |
| GGA | AAA | GGG | GGA | GAA | ACT | ATT | AAA | CAG | CTT | CAG | GAA | CGG | 668 |
| CCT | TTT | CCC | CCT | CTT | TGA | TAA | TTT | GTC | GAA | GTC | CTT | GCC | |
| Gly | Lys | Gly | Gly<br>205 | Glu | Thr | Ile | Lys | Gln<br>210 | Leu | Gln | Glu | Arg | |
| GCT | GGA | GTT | AAA | ATG | GTT | ATG | ATT | CAA | GAC | GGG | CCG | CAG | 707 |
| CGA | CCT | CAA | TTT | TAC | CAA | TAC | TAA | GTT | CTG | CCC | GGC | GTC | |
| Ala<br>215 | Gly | Val | Lys | Met | Val<br>220 | Met | Ile | Gln | Asp | Gly<br>225 | Pro | Gln | |
| AAC | ACT | GGT | GCT | GAC | AAA | CCT | CTT | AGG | ATT | ACA | GGA | GAC | 746 |
| TTG | TGA | CCA | CGA | CTG | TTT | GGA | GAA | TCC | TAA | TGT | CCT | CTG | |
| Asn | Thr | Gly<br>230 | Ala | Asp | Lys | Pro | Leu<br>235 | Arg | Ile | Thr | Gly | Asp<br>240 | |
| CCA | TAT | AAA | GTT | CAA | CAA | GCC | AAG | GAA | ATG | GTG | TTA | GAG | 785 |
| GGT | ATA | TTT | CAA | GTT | GTT | CGG | TTC | CTT | TAC | CAC | AAT | CTC | |
| Pro | Tyr | Lys | Val | Gln<br>245 | Gln | Ala | Lys | Glu | Met<br>250 | Val | Leu | Glu | |

-continued

| | | | | | | | | | | | | |
|---|---|---|---|---|---|---|---|---|---|---|---|---|
| TTA | ATT | CGT | GAT | CAA | GGC | GGT | TTC | AGA | GAA | GTT | CGG | AAT | 824 |
| AAT | TAA | GCA | CTA | GTT | CCG | CCA | AAG | TCT | CTT | CAA | GCC | TTA | |
| Leu | Ile | Arg | Asp | Gln | Gly | Gly | Phe | Arg | Glu | Val | Arg | Asn | |
| | 255 | | | | | 260 | | | | | 265 | | |
| GAG | TAT | GGG | TCA | AGA | ATA | GGA | GGA | AAT | GAA | GGG | ATA | GAT | 863 |
| CTC | ATA | CCC | AGT | TCT | TAT | CCT | CCT | TTA | CTT | CCC | TAT | CTA | |
| Glu | Tyr | Gly | Ser | Arg | Ile | Gly | Gly | Asn | Glu | Gly | Ile | Asp | |
| | | | 270 | | | | | 275 | | | | | |
| GTC | CCC | ATT | CCA | AGA | TTT | GCT | GTT | GGC | ATT | GTA | ATA | GGA | 902 |
| CAG | GGG | TAA | GGT | TCT | AAA | CGA | CAA | CCG | TAA | CAT | TAT | CCT | |
| Val | Pro | Ile | Pro | Arg | Phe | Ala | Val | Gly | Ile | Val | Ile | Gly | |
| 280 | | | | | 285 | | | | | 290 | | | |
| AGA | AAT | GGA | GAG | ATG | ATC | AAA | AAA | ATA | CAA | AAT | GAT | GCT | 941 |
| TCT | TTA | CCT | CTC | TAC | TAG | TTT | TTT | TAT | GTT | TTA | CTA | CGA | |
| Arg | Asn | Gly | Glu | Met | Ile | Lys | Lys | Ile | Gln | Asn | Asp | Ala | |
| | | 295 | | | | | 300 | | | | | 305 | |
| GGT | GTT | CGC | ATT | CAG | TTT | AAG | CCA | GAT | GAT | GGG | ACA | ACA | 980 |
| CCA | CAA | GCG | TAA | GTC | AAA | TTC | GGT | CTA | CTA | CCC | TGT | TGT | |
| Gly | Val | Arg | Ile | Gln | Phe | Lys | Pro | Asp | Asp | Gly | Thr | Thr | |
| | | | | 310 | | | | | 315 | | | | |
| CCC | GAA | AGG | ATA | GCA | CAA | ATA | ACA | GGA | CCT | CCA | GAC | CGA | 1019 |
| GGG | CTT | TCC | TAT | CGT | GTT | TAT | TGT | CCT | GGA | GGT | CTG | GCT | |
| Pro | Glu | Arg | Ile | Ala | Gln | Ile | Thr | Gly | Pro | Pro | Asp | Arg | |
| | 320 | | | | | 325 | | | | | 330 | | |
| TGT | CAA | CAT | GCT | GCA | GAA | ATT | ATT | ACA | GAC | CTT | CTT | CGA | 1058 |
| ACA | GTT | GTA | CGA | CGT | CTT | TAA | TAA | TGT | CTG | GAA | GAA | GCT | |
| Cys | Gln | His | Ala | Ala | Glu | Ile | Ile | Thr | Asp | Leu | Leu | Arg | |
| | | | 335 | | | | | 340 | | | | | |
| AGT | GTT | CAG | GCT | GGT | AAT | CCT | GGT | GGA | CCT | GGA | CCT | GGT | 1097 |
| TCA | CAA | GTC | CGA | CCA | TTA | GGA | CCA | CCT | GGA | CCT | GGA | CCA | |
| Ser | Val | Gln | Ala | Gly | Asn | Pro | Gly | Gly | Pro | Gly | Pro | Gly | |
| 345 | | | | | 350 | | | | | 355 | | | |
| GGT | CGA | GGA | AGA | GGT | AGA | GGT | CAA | GGC | AAC | TGG | AAC | ATG | 1136 |
| CCA | GCT | CCT | TCT | CCA | TCT | CCA | GTT | CCG | TTG | ACC | TTG | TAC | |
| Gly | Arg | Gly | Arg | Gly | Arg | Gly | Gln | Gly | Asn | Trp | Asn | Met | |
| | | | 360 | | | | | 365 | | | | | 370 |
| GGA | CCA | CCT | GGT | GGA | TTA | CAG | GAA | TTT | AAT | TTT | ATT | GTG | 1175 |
| CCT | GGT | GGA | CCA | CCT | AAT | GTC | CTT | AAA | TTA | AAA | TAA | CAC | |
| Gly | Pro | Pro | Gly | Gly | Leu | Gln | Glu | Phe | Asn | Phe | Ile | Val | |
| | | | | 375 | | | | | 380 | | | | |
| CCA | ACT | GGG | AAA | ACT | GGA | TTA | ATA | ATA | GGA | AAA | GGA | GGT | 1214 |
| GGT | TGA | CCC | TTT | TGA | CCT | AAT | TAT | TAT | CCT | TTT | CCT | CCA | |
| Pro | Thr | Gly | Lys | Thr | Gly | Leu | Ile | Ile | Gly | Lys | Gly | Gly | |
| | | 385 | | | | | 390 | | | | | 395 | |
| GAA | ACC | ATA | AAA | AGC | ATA | AGC | CAG | CAG | TCT | GGT | GCA | AGA | 1253 |
| CTT | TGG | TGT | TTT | TCG | TAT | TCG | GTC | GTC | AGA | CCA | CGT | TCT | |
| Glu | Thr | Ile | Lys | Ser | Ile | Ser | Gln | Gln | Ser | Gly | Ala | Arg | |
| | | | 400 | | | | | 405 | | | | | |
| ATA | GAA | CTT | CAG | AGA | AAT | CCT | CCA | CCA | AAT | GCA | GAT | CCT | 1292 |
| TAT | CTT | GAA | GTC | TCT | TTA | GGA | GGT | GGT | TTA | CGT | CTA | GGA | |
| Ile | Glu | Leu | Gln | Arg | Asn | Pro | Pro | Pro | Asn | Ala | Asp | Pro | |
| 410 | | | | | 415 | | | | | 420 | | | |
| AAT | ATG | AAG | TTA | TTT | ACA | ATT | CGT | GGC | ACT | CCA | CAA | CAG | 1331 |
| TTA | TAC | TTC | AAT | AAA | TGT | TAA | GCA | CCG | TGA | GGT | GTT | GTC | |
| Asn | Met | Lys | Leu | Phe | Thr | Ile | Arg | Gly | Thr | Pro | Gln | Gln | |
| | | 425 | | | | | 430 | | | | | 435 | |
| ATA | GAC | TAT | GCT | CGG | CAA | CTC | ATA | GAA | GAA | AAG | ATT | GGT | 1370 |
| TAT | CTG | ATA | CGA | GCC | GTT | GAG | TAT | CTT | CTT | TTC | TAA | CCA | |
| Ile | Asp | Tyr | Ala | Arg | Gln | Leu | Ile | Glu | Glu | Lys | Ile | Gly | |
| | | | | 440 | | | | | 445 | | | | |
| GGC | CCA | GTA | AAT | CCT | TTA | GGG | CCA | CCT | GTA | CCC | CAT | GGG | 1409 |
| CCG | GGT | CAT | TTA | GGA | AAT | CCC | GGT | GGA | CAT | GGG | GTA | CCC | |
| Gly | Pro | Val | Asn | Pro | Leu | Gly | Pro | Pro | Val | Pro | His | Gly | |
| | 450 | | | | | 455 | | | | | 460 | | |
| CCC | CAT | GGT | GTC | CCA | GGC | CCC | CAT | GGA | CCT | CCT | GGG | CCT | 1448 |
| GGG | GTA | CCA | CAG | GGT | CCG | GGG | GTA | CCT | GGA | GGA | CCC | GGA | |
| Pro | His | Gly | Val | Pro | Gly | Pro | His | Gly | Pro | Pro | Gly | Pro | |
| | | | 465 | | | | | 470 | | | | | |
| CCA | GGG | CCT | GGA | ACT | CCA | ATG | GGA | CCA | TAC | AAC | CCT | GCA | 1487 |
| GGT | CCC | GGA | CCT | TGA | GGT | TAC | CCT | GGT | ATG | TTG | GGA | CGT | |
| Pro | Gly | Pro | Gly | Thr | Pro | Met | Gly | Pro | Tyr | Asn | Pro | Ala | |
| 475 | | | | | 480 | | | | | 485 | | | |
| CCT | TAT | AAT | CCT | GGA | CCA | CCA | GGC | CCG | GCT | CCT | CAT | GGT | 1526 |
| GGA | ATA | TTA | GGA | CCT | GGT | GGT | CCG | GGC | CGA | GGA | GTA | CCA | |
| Pro | Tyr | Asn | Pro | Gly | Pro | Pro | Gly | Pro | Ala | Pro | His | Gly | |
| | | | 490 | | | | | 495 | | | | | 500 |
| CCT | CCA | GCC | CCA | TAT | GCT | CCC | CAG | GGA | TGG | GGA | AAT | GCA | 1565 |
| GGA | GGT | CGG | GGT | ATA | CGA | GGG | GTC | CCT | ACC | CCT | TTA | CGT | |
| Pro | Pro | Ala | Pro | Tyr | Ala | Pro | Gln | Gly | Trp | Gly | Asn | Ala | |
| | | | | 505 | | | | | 510 | | | | |

-continued

| | | | | | | | | | | | | |
|---|---|---|---|---|---|---|---|---|---|---|---|---|
| TAT | CCA | CAC | TGG | CAG | CAG | CAG | GCT | CCT | CCT | GAT | CCA | GCT | 1604 |
| ATA | GGT | GTG | ACC | GTC | GTC | GTC | CGA | GGA | GGA | CTA | GGT | CGA | |
| Tyr | Pro | His | Trp | Gln | Gln | Gln | Ala | Pro | Pro | Asp | Pro | Ala | |
| | 515 | | | | 520 | | | | | 525 | | | |
| AAG | GCA | GGA | ACG | GAT | CCA | AAT | TCA | GCA | GCT | TGG | GCT | GCT | 1643 |
| TTC | CGT | CCT | TGC | CTA | GGT | TTA | AGT | CGT | CGA | ACC | CGA | CGA | |
| Lys | Ala | Gly | Thr | Asp | Pro | Asn | Ser | Ala | Ala | Trp | Ala | Ala | |
| | | | 530 | | | | | 535 | | | | | |
| TAT | TAC | GCT | CAC | TAT | TAT | CAA | CAG | CAA | GCA | CAG | CCA | CCA | 1682 |
| ATA | ATG | CGA | GTG | ATA | ATA | GTT | GTC | GTT | CGT | GTC | GGT | GGT | |
| Tyr | Tyr | Ala | His | Tyr | Tyr | Gln | Gln | Gln | Ala | Gln | Pro | Pro | |
| 540 | | | | | 545 | | | | | 550 | | | |
| CCA | GCA | GCC | CCT | GCA | GGT | GCA | CCA | ACT | ACA | ACT | CAA | ACT | 1721 |
| GGT | CGT | CGG | GGA | CGT | CCA | CGT | GGT | TGA | TGT | TGA | GTT | TGA | |
| Pro | Ala | Ala | Pro | Ala | Gly | Ala | Pro | Thr | Thr | Thr | Gln | Thr | |
| | | 555 | | | | | 560 | | | | | 565 | |
| AAT | GGA | CAA | GGA | GAT | CAG | CAG | AAT | CCA | GCC | CCA | GCT | GGA | 1760 |
| TTA | CCT | GTT | CCT | CTA | GTC | GTC | TTA | GGT | CGG | GGT | CGA | CCT | |
| Asn | Gly | Gln | Gly | Asp | Gln | Gln | Asn | Pro | Ala | Pro | Ala | Gly | |
| | | | | 570 | | | | | 575 | | | | |
| CAG | GTT | GAT | TAT | ACC | AAG | GCT | TGG | GAA | GAG | TAC | TAC | AAG | 1799 |
| GTC | CAA | CTA | ATA | TGG | TTC | CGA | ACC | CTT | CTC | ATG | ATG | TTC | |
| Gln | Val | Asp | Tyr | Thr | Lys | Ala | Trp | Glu | Glu | Tyr | Tyr | Lys | |
| | 580 | | | | | 585 | | | | | 590 | | |
| AAA | ATG | GGT | CAG | GCA | GTT | CCT | GCT | CCG | ACT | GGG | GCT | CCT | 1838 |
| TTT | TAC | CCA | GTC | CGT | CAA | GGA | CGA | GGC | TGA | CCC | CGA | GGA | |
| Lys | Met | Gly | Gln | Ala | Val | Pro | Ala | Pro | Thr | Gly | Ala | Pro | |
| | | | 595 | | | | | 600 | | | | | |
| CCA | GGT | GGT | CAG | CCA | GAT | TAT | AGT | GCA | GCC | TGG | GCT | GAG | 1877 |
| GGT | CCA | CCA | GTC | GGT | CTA | ATA | TCA | CGT | CGG | ACC | CGA | CTC | |
| Pro | Gly | Gly | Gln | Pro | Asp | Tyr | Ser | Ala | Ala | Trp | Ala | Glu | |
| 605 | | | | | 610 | | | | | 615 | | | |
| CAT | TAT | AGA | CAA | CAA | GCA | GCC | TAT | TAT | GCC | CAG | ACA | AGT | 1916 |
| GTA | ATA | TCT | GTT | GTT | CGT | CGG | ATA | ATA | CGG | GTC | TGT | TCA | |
| His | Tyr | Arg | Gln | Gln | Ala | Ala | Tyr | Tyr | Ala | Gln | Thr | Ser | |
| | | 620 | | | | | 625 | | | | | 630 | |
| CCC | CAG | GGA | ATG | CCA | CAG | CAT | CCT | CCA | GCA | CCT | CAG | GGC | 1955 |
| GGG | GTC | CCT | TAC | GGT | GTC | GTA | GGA | GGT | CGT | GGA | GTC | CCG | |
| Pro | Gln | Gly | Met | Pro | Gln | His | Pro | Pro | Ala | Pro | Gln | Gly | |
| | | | | 635 | | | | | 640 | | | | |
| CAA | TAA | TAA | GAAGTGGACA | | ATACAGTATT | | TGCTTCATTG | | | | | | 1994 |
| GTT | ATT | ATT | CTTCACCTGT | | TATGTCATAA | | ACGAAGTAAC | | | | | | |
| Gln | | | | | | | | | | | | | |

| | | | | |
|---|---|---|---|---|
| TGTGGGGGAA | AAAAACCTTT | GTTAAATATA | TGGATGCAGA | 2034 |
| ACACCCCCTT | TTTTTGGAAA | CAATTTATAT | ACCTACGTCT | |
| CGACTTGATG | AAGATCTTAA | TTTTGTTTTT | GGTTTAAAAT | 2074 |
| GCTGAACTAC | TTCTAGAATT | AAAACAAAAA | CCAAATTTTA | |
| AGTGTTTCCT | TTTTTTTTTT | TTTTTTTTG | AAAATGTACA | 2114 |
| TCACAAGGA | AAAAAAAAAA | AAAAAAAAAC | TTTTACATGT | |
| AAATATCTAT | CACTACTGAT | AGGAGGTTAA | TATTTCTGTG | 2154 |
| TTTATAGATA | GTGATGACTA | TCCTCCAATT | ATAAAGACAC | |
| TAGAAATGAA | AATTGGTTTG | TTTTTAGTAT | TTAGTGTAGA | 2194 |
| ATCTTTACTT | TTAACCAAAC | AAAAATCATA | AATCACATCT | |
| TGTACACATT | CCAGCAAATG | TATTTGCAAT | TATGTGGTTG | 2234 |
| ACATGTGTAA | GGTCGTTTAC | ATAAACGTTA | ATACACCAAC | |
| ATGCTTTGTG | ATATAAATGT | ACTTTTTCAA | TGTATACTTT | 2274 |
| TACGAAACAC | TATATTTACA | TGAAAAAGTT | ACATATGAAA | |
| CACTTTCCAA | ATGCCTGTTT | TGTGCTTTAC | AATAAATGAT | 2314 |
| GTGAAAGGTT | TACGGACAAA | ACACGAAATG | TTATTTACTA | |
| ATGAAACCTC | AAAAAAAAAA | AAAAAAAAAA | AAAAAAAAAA | 2354 |
| TACTTTGGAG | TTTTTTTTTT | TTTTTTTTTT | TTTTTTTTTT | |
| AAAAAAAAAA | AAAAAAAAAA | AAAAAAAAAA | | 2384 |
| TTTTTTTTTT | TTTTTTTTTT | TTTTTTTTTT | | |

Three clones from a BJAB cDNA library and three clones from an activated, human peripheral blood lymphocyte cDNA library contain the above sequence. Three clones from the same BJAB library and two clones from the activated lymphocyte library are lacking nucleotides 316, 317 and 318 (SEQ ID NO:9). The mRNA lacking these three nucleotides would encode a variant protein lacking serine 97 (SEQ ID NO:10).

Though the 5' untranslated region of the message appears to be unusually short and contains no in-frame stop codons, the initiator methionine is contained in a nine out of ten match with the Kozak consensus. (M. Kozak, "Structural features in eukaryotic mRNAs that modulate the initiation of translation". *J. Biol. Chem.* 266(30), 19867–19870 (1991)). The deduced polypeptide, 644 amino acids in length, has a calculated molecular weight of 67.5 kd consistent with the molecular weight of the purified protein. The amino acid sequence can be found in SEQ ID NO:2.

To create the full length cDNA, pools of degenerate oligonucleotides were synthesized to correspond to the amino acid sequence of the peptide encoded by nucleotides 843 to 860 and used as primers in a PCR reaction. The oligo sequences (SEQ ID NO:3) are:

5'-CAGAATTCGGIGGIAAYGARGGIANCG-3' where I indicates an inosine residue, and Y is either T or C, R is either A or G, and N is either I or T.

Degenerate oligonucleotides were also synthesized to correspond to the peptide encoded by nucleotides 957 to 971 and used together with the above primer (SEQ ID NO:3) in a PCR reaction which amplified the PCR product encoded by nucleotides 861 to 956 from human cDNA. The sequences (SEQ ID NO:4) of this degenerate oligo pool are:

5'-GAGTCGACRTCRTCRTCIGGYTTRAA-3' where R is either A or G, and Y is either C or T.

The full length cDNA sequence has features which suggest multiple modes of FBP regulation. There is an unusual codon bias. For every amino acid with a degenerate codon, except glutamine, the FBP sequence avoids the codons preferred in a survey of 2,681 human genes (K-n. Wada, Y. Wada, F. Ishibashi, T. Gojobori and T. Ikemura. Codon usage tabulated from the GenBank genetic sequence data. *Nucleic Acids Res.* 20(supplement), 2111–2118 (1992)) suggesting translational regulation. The existence of alternate isoforms of FBP generated by regulation of RNA processing is suggested by multiple independent clones, half of which exhibit a precise deletion of 3 nucleotides at basepair 316, 317 and 318, removing serine 97 (see FIG. 2B). The surrounding sequence is consistent with an alternate splice acceptor site (S. M. Mount, *Nuc. Acids Res.* 10,459 (1982)) which could generate this deletion.

Other variations of the cDNA sequence and encoded protein were found in separate clones. In a clone labeled "25-1" an A residue was found at nucleic acid position 473, which resulted in a complementary base T and a codon specifying an isoleucine at amino acid 149.

The clone from an HL60 cDNA library labeled "3-1" contains 10 basepairs of 5' untranslated sequence, followed by an open reading frame comprised of the nucleotides from position 858 to position 1561 shown above in SEQ ID NO:1 and a unique 3' end cDNA sequence of 25 base pairs, followed by two adjacent stop codons and additional 3' untranslated sequence. The sequence of clone 3-1 is as follows (SEQ ID NO: 5):

| GGAATTCCGG | ATA | GAT | GTC | CCC | ATT | CCA | AGA | TTT | GCT | GTT | 40 |
|---|---|---|---|---|---|---|---|---|---|---|---|
| CCTTAAGGCC | TAT | CTA | CAG | GGG | TAA | GGT | TCT | AAA | CGA | CAA | |
| | Ile | Asp | Val | Pro | Ile | Pro | Arg | Phe | Ala | Val | |
| | 1 | | | | 5 | | | | | 10 | |
| GGC | ATT | GTA | ATA | GGA | AGA | AAT | GGA | GAG | ATG | ATC | AAA | AAA | 79 |
| CCG | TAA | CAT | TAT | CCT | TCT | TTA | CCT | CTC | TAC | TAG | TTT | TTT | |
| Gly | Ile | Val | Ile | Gly | Arg | Asn | Gly | Glu | Met | Ile | Lys | Lys | |
| | | | | 15 | | | | | 20 | | | | |
| ATA | CAA | AAT | GAT | GCT | GGT | GTT | CGC | ATT | CAG | TTT | AAG | CCA | 118 |
| TAT | GTT | TTA | CTA | CGA | CCA | CAA | GCG | TAA | GTC | AAA | TTC | GGT | |
| Ile | Gln | Asn | Asp | Ala | Gly | Val | Arg | Ile | Gln | Phe | Lys | Pro | |
| | 25 | | | | 30 | | | | | 35 | | | |
| GAT | GAT | GGG | ACA | ACA | CCC | GAA | AGG | ATA | GCA | CAA | ATA | ACA | 157 |
| CTA | CTA | CCC | TGT | TGT | GGG | CTT | TCC | TAT | CGT | GTT | TAT | TGT | |
| Asp | Asp | Gly | Thr | Thr | Pro | Glu | Arg | Ile | Ala | Gln | Ile | Thr | |
| | | | 40 | | | | | 45 | | | | | |
| GGA | CCT | CCA | GAC | CGA | TGT | CAA | CAT | GCT | GCA | GAA | ATT | ATT | 196 |
| CCT | GGA | GGT | CTG | GCT | ACA | GTT | GTA | CGA | CGT | CTT | TAA | TAA | |
| Gly | Pro | Pro | Asp | Arg | Cys | Gln | His | Ala | Ala | Glu | Ile | Ile | |
| 50 | | | | | 55 | | | | | 60 | | | |
| ACA | GAC | CTT | CTT | CGA | AGT | GTT | CAG | GCT | GGT | AAT | CCT | GGT | 235 |
| TGT | CTG | GAA | GAA | GCT | TCA | CAA | GTC | CGA | CCA | TTA | GGA | CCA | |
| Thr | Asp | Leu | Leu | Arg | Ser | Val | Gln | Ala | Gly | Asn | Pro | Gly | |
| | | 65 | | | | | 70 | | | | | 75 | |
| GGA | CCT | GGA | CCT | GGT | GGT | CGA | GGA | AGA | GGT | AGA | GGT | CAA | 274 |
| CCT | GGA | CCT | GGA | CCA | CCA | GCT | CCT | TCT | CCA | TCT | CCA | GTT | |
| Gly | Pro | Gly | Pro | Gly | Gly | Arg | Gly | Arg | Gly | Arg | Gly | Gln | |
| | | | | 80 | | | | | 85 | | | | |
| GGC | AAC | TGG | AAC | ATG | GGA | CCA | CCT | GGT | GGA | TTA | CAG | GAA | 313 |
| CCG | TTG | ACC | TTG | TAC | CCT | GGT | GGA | CCA | CCT | AAT | GTC | CTT | |
| Gly | Asn | Trp | Asn | Met | Gly | Pro | Pro | Gly | Gly | Leu | Gln | Glu | |
| | | 90 | | | | | 95 | | | | | 100 | |
| TTT | AAT | TTT | ATT | GTG | CCA | ACT | GGG | AAA | ACT | GGA | TTA | ATA | 352 |
| AAA | TTA | AAA | TAA | CAC | GGT | TGA | CCC | TTT | TGA | CCT | AAT | TAT | |
| Phe | Asn | Phe | Ile | Val | Pro | Thr | Gly | Lys | Thr | Gly | Leu | Ile | |
| | | | 105 | | | | | 110 | | | | | |
| ATA | GGA | AAA | GGA | GGT | GAA | ACC | ATA | AAA | AGC | ATA | AGC | CAG | 391 |
| TAT | CCT | TTT | CCT | CCA | CTT | TGG | TAT | TTT | TCG | TAT | TCG | GTC | |
| Ile | Gly | Lys | Gly | Gly | Glu | Thr | Ile | Lys | Ser | Ile | Ser | Gln | |
| 115 | | | | | 120 | | | | | 125 | | | |
| CAG | TCT | GGT | GCA | AGA | ATA | GAA | CTT | CAG | AGA | AAT | CCT | CCA | 430 |
| GTC | AGA | CCA | CGT | TCT | TAT | CTT | GAA | GTC | TCT | TTA | GGA | GGT | |
| Gln | Ser | Gly | Ala | Arg | Ile | Glu | Leu | Gln | Arg | Asn | Pro | Pro | |
| | | 130 | | | | | 135 | | | | | 140 | |
| CCA | AAT | GCA | GAT | CCT | AAT | ATG | AAG | TTA | TTT | ACA | ATT | CGT | 469 |
| GGT | TTA | CGT | CTA | GGA | TTA | TAC | TTC | AAT | AAA | TGT | TAA | GCA | |
| Pro | Asn | Ala | Asp | Pro | Asn | Met | Lys | Leu | Phe | Thr | Ile | Arg | |
| | | | 145 | | | | | 150 | | | | | |
| GGC | ACT | CCA | CAA | CAG | ATA | GAC | TAT | GCT | CGG | CAA | CTC | ATA | 508 |
| CCG | TGA | GGT | GTT | GTC | TAT | CTG | ATA | CGA | GCC | GTT | GAG | TAT | |
| Gly | Thr | Pro | Gln | Gln | Ile | Asp | Tyr | Ala | Arg | Gln | Leu | Ile | |
| | 155 | | | | 160 | | | | | 165 | | | |
| GAA | GAA | AAG | ATT | GGT | GGC | CCA | GTA | AAT | CCT | TTA | GGG | CCA | 547 |
| CTT | CTT | TTC | TAA | CCA | CCG | GGT | CAT | TTA | GGA | AAT | CCC | GGT | |
| Glu | Glu | Lys | Ile | Gly | Gly | Pro | Val | Asn | Pro | Leu | Gly | Pro | |

|     |     |     |     | 170 |     |     |     | 175 |     |     |     |     |     |
|-----|-----|-----|-----|-----|-----|-----|-----|-----|-----|-----|-----|-----|-----|
| CCT | GTA | CCC | CAT | GGG | CCC | CAT | GGT | GTC | CCA | GGC | CCC | CAT | 586 |
| GGA | CAT | GGG | GTA | CCC | GGG | GTA | CCA | CAG | GGT | CCG | GGG | GTA |     |
| Pro | Val | Pro | His | Gly | Pro | His | Gly | Val | Pro | Gly | Pro | His |     |
| 180 |     |     |     |     | 185 |     |     |     |     | 190 |     |     |     |
| GGA | CCT | CCT | GGG | CCT | CCA | GGG | CCT | GGA | ACT | CCA | ATG | GGA | 625 |
| CCT | GGA | GGA | CCC | GGA | GGT | CCC | GGA | CCT | TGA | GGT | TAC | CCT |     |
| Gly | Pro | Pro | Gly | Pro | Pro | Gly | Pro | Gly | Thr | Pro | Met | Gly |     |
|     |     | 195 |     |     |     |     | 200 |     |     |     |     | 205 |     |
| CCA | TAC | AAC | CCT | GCA | CCT | TAT | AAT | CCT | GGA | CCA | CCA | GGC | 664 |
| GGT | ATG | TTG | GGA | CGT | GGA | ATA | TTA | GGA | CCT | GGT | GGT | CCG |     |
| Pro | Tyr | Asn | Pro | Ala | Pro | Tyr | Asn | Pro | Gly | Pro | Pro | Gly |     |
|     |     |     |     | 210 |     |     |     |     | 215 |     |     |     |     |
| CCG | GCT | CCT | CAT | GGT | CCT | CCA | GCC | CCA | TAT | GCT | CCC | CAG | 703 |
| GGC | CGA | GGA | GTA | CCA | GGA | GGT | CGG | GGT | ATA | CGA | GGG | GTC |     |
| Pro | Ala | Pro | His | Gly | Pro | Pro | Ala | Pro | Tyr | Ala | Pro | Gln |     |
|     |     | 220 |     |     |     |     | 225 |     |     |     |     | 230 |     |
| GGA | TGG | GGA | AAG | GAA | ATT | GAG | CAG | AAG | GTA | CAG | GAG | TAA | 742 |
| CCT | ACC | CCT | TTC | CTT | TAA | CTC | GTC | TTC | CAT | GTC | CTC | ATT |     |
| Gly | Trp | Gly | Lys | Glu | Ile | Glu | Gln | Lys | Val | Gln | Glu |     |     |
|     |     |     |     | 235 |     |     |     |     | 240 |     |     |     |     |

| | | | |
|---|---|---|---|
| TAG CAATTCCCTG | TAGCTCTCAA | AGCAAATTTT | GAGCTCATTT | 785 |
| ATC GTTAAGGGAC | ATCGAGAGTT | TCGTTTAAAA | CTCGAGTAAA |     |
| TTCTTTTTCT | GCAAGCTCAG | CAGCAGAATG | CCCAGAGTCT | 825 |
| AAGAAAAAGA | CGTTCGAGTC | GTCGTCTTAC | GGGTCTCAGA |     |
| TCCCTGGTAG | ATGCAGGTTC | CATAGCGACG | TTCTCCTGCA | 865 |
| AGGGACCATC | TACGTCCAAG | GTATCGCTGC | AAGAGGACGT |     |
| ATGCACGCTG | GTATTCTGCA | ATAGCAGGCC | ATGTTTTCCT | 905 |
| TACGTGCGAC | CATAAGACGT | TATCGTCCGG | TACAAAAGGA |     |
| TGAGCCTGGA | TGCTTTGGAG | CCAAGCTTTC | GTCCCATGCA | 945 |
| ACTCGGACCT | ACGAAACCTC | GGTTCGAAAG | CAGGGTACGT |     |
| AGGGAAACAA | CCACTTCTGG | GATGTCCGCT | GCAATCTGCT | 985 |
| TCCCTTTGTT | GGTGAAGACC | CTACAGGCGA | CGTTAGACGA |     |
| CCGGGGCTGC | AGCAACCTCA | TCAGCTCTCT | TGCCTGGAGT | 1025 |
| GGCCCCGACG | TCGTTGGAGT | AGTCGAGAGA | ACGGACCTCA |     |
| GGCTCAGCCT | GGCCTGCAGG | GCCACCAGGA | GAATGGCAGC | 1065 |
| CCGAGTCGGA | CCGGACGTCC | CGGTGGTCCT | CTTACCGTCG |     |
| AAGGATGGCG | AGGGTCCTCA | TGGCTGGAAT | TC | 1097 |
| TTCCTACGC | TCCCAGGAGT | ACCGACCTTA | AG |     |

The amino acid sequence for the protein encoded by the cDNA sequence for clone 3-1 can be found in SEQ ID NO:6.

In addition, the clone from an activated, human peripheral blood lymphocyte cDNA library labeled "31-10" contains 24 basepairs of 5' untranslated sequence, followed by an open reading frame comprised of the basepairs from position 135 to position 1991 of the DROME sequence given in SEQ ID NO:1 with two exceptions. Clone 31-10 contains 63 nucleotides inserted at position 238 in the DROME cDNA sequence which probably result from an intron which had not been spliced out in the DROME mRNA molecule that gave rise to the 31-10 clone. The inserted nucleotides remain in the open reading frame and are translated into an alternate form of the DROME protein.

The 31-10 clone also deviates in that nucleotides from position 1807 to 1952 in the DROME cDNA sequence are deleted. This deletion shifts out of frame the stop codons which would terminate translation in the other clones. When the mRNA represented by the 31-10 cDNA is translated, additional amino acids must be added to the C-terminal end of the DROME protein.

The sequence of clone 31-10 is as follows (SEQ ID NO:7):

| | | | | | | | | | | | | |
|---|---|---|---|---|---|---|---|---|---|---|---|---|
| GAATTCCGGA | CGACAGCGGC | TCTG | AGA | GCC | CGG | CAG | ATT | GCA | 42 |
| CTTAAGGCCT | GCTGTCGCCG | AGAC | TCT | CGG | GCC | GTC | TAA | CGT |    |
|            |            |      | Arg | Ala | Arg | Gln | Ile | Ala |    |
|            |            |      | 1   |     |     |     | 5   |     |    |
| GCA | AAA | ATT | GGA | GGT | GAT | GCA | GGG | ACA | TCA | CTG | AAT | TCA | 81 |
| CGT | TTT | TAA | CCT | CCA | CTA | CGT | CCC | TGT | AGT | GAC | TTA | AGT |    |
| Ala | Lys | Ile | Gly | Gly | Asp | Ala | Gly | Thr | Ser | Leu | Asn | Ser |    |
|     |     |     | 10  |     |     |     |     | 15  |     |     |     |     |    |
| AAT | GAC | TAT | GGT | TAT | GGG | GGA | CAA | AAA | AGA | CCT | TTA | GAA | 120 |
| TTA | CTG | ATA | CCA | ATA | CCC | CCT | GTT | TTT | TCT | GGA | AAT | CTT |     |
| Asn | Asp | Tyr | Gly | Tyr | Gly | Gly | Gln | Lys | Arg | Pro | Leu | Glu |     |
| 20  |     |     |     |     | 25  |     |     |     |     | 30  |     |     |     |
| GAT | GGA | GAT | GGC | TCT | TGG | ACA | AGT | CCG | AGC | AGT | ACA | ACA | 159 |
| CTA | CCT | CTA | CCG | AGA | ACC | TGT | TCA | GGC | TCG | TCA | TGT | TGT |     |
| Asp | Gly | Asp | Gly | Ser | Trp | Thr | Ser | Pro | Ser | Ser | Thr | Thr |     |
|     |     | 35  |     |     |     |     | 40  |     |     |     |     | 45  |     |
| CAC | TGG | GAG | GGA | ATG | CCC | TCT | CCT | TTT | AAA | GAT | CAA | CCA | 198 |
| GTG | ACC | CTC | CCT | TAC | GGG | AGA | GGA | AAA | TTT | CTA | GTT | GGT |     |
| His | Trp | Glu | Gly | Met | Pro | Ser | Pro | Phe | Lys | Asp | Gln | Pro |     |
|     |     |     |     | 50  |     |     |     |     | 55  |     |     |     |     |

-continued

| | | | | | | | | | | | | |
|---|---|---|---|---|---|---|---|---|---|---|---|---|
| GAT | GCT | AAG | AAA | GTT | GCT | CCT | CAA | AAT | GAC | TCT | TTT | GGA | 237 |
| CTA | CGA | TTC | TTT | CAA | CGA | GGA | GTT | TTA | CTG | AGA | AAA | CCT | |
| Asp | Ala | Lys | Lys | Val | Ala | Pro | Gln | Asn | Asp | Ser | Phe | Gly | |
| | 60 | | | | | 65 | | | | | 70 | | |
| ACA | CAG | TTA | CCA | CCG | ATG | CAT | CAG | CAG | CAA | AGA | TCT | GTA | 276 |
| TGT | GTC | AAT | GGT | GGC | TAC | GTA | GTC | GTC | GTT | TCT | AGA | CAT | |
| Thr | Gln | Leu | Pro | Pro | Met | His | Gln | Gln | Gln | Arg | Ser | Val | |
| | | | 75 | | | | | 80 | | | | | |
| ATG | ACA | GAA | GAA | TAC | AAA | GTT | CCA | GAT | GGA | ATG | GTT | GGA | 315 |
| TAC | TGT | CTT | CTT | ATG | TTT | CAA | GGT | CTA | CCT | TAC | CAA | CCT | |
| Met | Thr | Glu | Glu | Tyr | Lys | Val | Pro | Asp | Gly | Met | Val | Gly | |
| 85 | | | | | 90 | | | | | 95 | | | |
| TTC | ATA | ATT | GGC | AGA | GGA | GGT | GAA | CAG | ATC | TCA | CGC | ATA | 354 |
| AAG | TAT | TAA | CCG | TCT | CCT | CCA | CTT | GTC | TAG | AGT | GCG | TAT | |
| Phe | Ile | Ile | Gly | Arg | Gly | Gly | Glu | Gln | Ile | Ser | Arg | Ile | |
| | | 100 | | | | | 105 | | | | | 110 | |
| CAA | CAG | GAA | TCT | GGA | TGC | AAA | ATA | CAG | ATA | GCT | CCT | GAC | 393 |
| GTT | GTC | CTT | AGA | CCT | ACG | TTT | TAT | GTC | TAT | CGA | GGA | CTG | |
| Gln | Gln | Glu | Ser | Gly | Cys | Lys | Ile | Gln | Ile | Ala | Pro | Asp | |
| | | | | 115 | | | | | 120 | | | | |
| AGT | GGT | GGC | CTT | CCA | GAA | AGG | TCC | TGT | ATG | TTA | ACT | GGA | 432 |
| TCA | CCA | CCG | GAA | GGT | CTT | TCC | AGG | ACA | TAC | AAT | TGA | CCT | |
| Ser | Gly | Gly | Leu | Pro | Glu | Arg | Ser | Cys | Met | Leu | Thr | Gly | |
| | 125 | | | | | 130 | | | | | 135 | | |
| ACA | CCT | GAA | TCT | GTC | CAG | TCA | GCA | AAA | CGG | TTA | CTG | GAC | 471 |
| TGT | GGA | CTT | AGA | CAG | GTC | AGT | CGT | TTT | GCC | AAT | GAC | CTG | |
| Thr | Pro | Glu | Ser | Val | Gln | Ser | Ala | Lys | Arg | Leu | Leu | Asp | |
| | | | 140 | | | | | 145 | | | | | |
| CAG | ATT | GTT | GAA | AAA | GGA | AGA | CCA | GCT | CCT | GGC | TTC | CAT | 510 |
| GTC | TAA | CAA | CTT | TTT | CCT | TCT | GGT | CGA | GGA | CCG | AAG | GTA | |
| Gln | Ile | Val | Glu | Lys | Gly | Arg | Pro | Ala | Pro | Gly | Phe | His | |
| 150 | | | | | 155 | | | | | 160 | | | |
| CAT | GGC | GAT | GGA | CCG | GGA | AAT | GCA | GTT | CAA | GAA | ATC | ATG | 549 |
| GTA | CCG | CTA | CCT | GGC | CCT | TTA | CGT | CAA | GTT | CTT | TAG | TAC | |
| His | Gly | Asp | Gly | Pro | Gly | Asn | Ala | Val | Gln | Glu | Ile | Met | |
| | | 165 | | | | | 170 | | | | | 175 | |
| ATT | CCA | GCT | AGC | AAG | GCA | GGA | TTA | GTC | ATT | GGA | AAA | GGG | 588 |
| TAA | GGT | CGA | TCG | TTC | CGT | CCT | AAT | CAG | TAA | CCT | TTT | CCC | |
| Ile | Pro | Ala | Ser | Lys | Ala | Gly | Leu | Val | Ile | Gly | Lys | Gly | |
| | | | | 180 | | | | | 185 | | | | |
| GGA | GAA | ACT | ATT | AAA | CAG | CTT | CAG | GAA | CGG | GCT | GGA | GTT | 627 |
| CCT | CTT | TGA | TAA | TTT | GTC | GAA | GTC | CTT | GCC | CGA | CCT | CAA | |
| Gly | Glu | Thr | Ile | Lys | Gln | Leu | Gln | Glu | Arg | Ala | Gly | Val | |
| | 190 | | | | | 195 | | | | | 200 | | |
| AAA | ATG | GTT | ATG | ATT | CAA | GAC | GGG | CCG | CAG | AAC | ACT | GGT | 666 |
| TTT | TAC | CAA | TAC | TAA | GTT | CTG | CCC | GGC | GTC | TTG | TGA | CCA | |
| Lys | Met | Val | Met | Ile | Gln | Asp | Gly | Pro | Gln | Asn | Thr | Gly | |
| | | | 205 | | | | | 210 | | | | | |
| GCT | GAC | AAA | CCT | CTT | AGG | ATT | ACA | GGA | GAC | CCA | TAT | AAA | 705 |
| CGA | CTG | TTT | GGA | GAA | TCC | TAA | TGT | CCT | CTG | GGT | ATA | TTT | |
| Ala | Asp | Lys | Pro | Leu | Arg | Ile | Thr | Gly | Asp | Pro | Tyr | Lys | |
| 215 | | | | | 220 | | | | | 225 | | | |
| GTT | CAA | CAA | GCC | AAG | GAA | ATG | GTG | TTA | GAG | TTA | ATT | CGT | 744 |
| CAA | GTT | GTT | CGG | TTC | CTT | TAC | CAC | AAT | CTC | AAT | TAA | GCA | |
| Val | Gln | Gln | Ala | Lys | Glu | Met | Val | Leu | Glu | Leu | Ile | Arg | |
| | | 230 | | | | | 235 | | | | | 240 | |
| GAT | CAA | GGC | GGT | TTC | AGA | GAA | GTT | CGG | AAT | GAG | TAT | GGG | 783 |
| CTA | GTT | CCG | CCA | AAG | TCT | CTT | CAA | GCC | TTA | CTC | ATA | CCC | |
| Asp | Gln | Gly | Gly | Phe | Arg | Glu | Val | Arg | Asn | Glu | Tyr | Gly | |
| | | | | 245 | | | | | 250 | | | | |
| TCA | AGA | ATA | GGA | GGA | AAT | GAA | GGG | ATA | GAT | GTC | CCC | ATT | 822 |
| AGT | TCT | TAT | CCT | CCT | TTA | CTT | CCC | TAT | CTA | CAG | GGG | TAA | |
| Ser | Arg | Ile | Gly | Gly | Asn | Glu | Gly | Ile | Asp | Val | Pro | Ile | |
| | 255 | | | | | 260 | | | | | 265 | | |
| CCA | AGA | TTT | GCT | GTT | GGC | ATT | GTA | ATA | GGA | AGA | AAT | GGA | 861 |
| GGT | TCT | AAA | CGA | CAA | CCG | TAA | CAT | TAT | CCT | TCT | TTA | CCT | |
| Pro | Arg | Phe | Ala | Val | Gly | Ile | Val | Ile | Gly | Arg | Asn | Gly | |
| | | | 270 | | | | | 275 | | | | | |
| GAG | ATG | ATC | AAA | AAA | ATA | CAA | AAT | GAT | GCT | GGT | GTT | CGC | 900 |
| CTC | TAC | TAG | TTT | TTT | TAT | GTT | TTA | CTA | CGA | CCA | CAA | GCG | |
| Glu | Met | Ile | Lys | Lys | Ile | Gln | Asn | Asp | Ala | Gly | Val | Arg | |
| 280 | | | | | 285 | | | | | 290 | | | |
| ATT | CAG | TTT | AAG | CCA | GAT | GAT | GGG | ACA | ACA | CCC | GAA | AGG | 939 |
| TAA | GTC | AAA | TTC | GGT | CTA | CTA | CCC | TGT | TGT | GGG | CTT | TCC | |
| Ile | Gln | Phe | Lys | Pro | Asp | Asp | Gly | Thr | Thr | Pro | Glu | Arg | |
| | | 295 | | | | | 300 | | | | | 305 | |
| ATA | GCA | CAA | ATA | ACA | GGA | CCT | CCA | GAC | CGA | TGT | CAA | CAT | 978 |
| TAT | CGT | GTT | TAT | TGT | CCT | GGA | GGT | CTG | GCT | ACA | GTT | GTA | |
| Ile | Ala | Gln | Ile | Thr | Gly | Pro | Pro | Asp | Arg | Cys | Gln | His | |
| | | | | 310 | | | | | 315 | | | | |

-continued

| | | | | | | | | | | | | |
|---|---|---|---|---|---|---|---|---|---|---|---|---|
| GCT | GCA | GAA | ATT | ATT | ACA | GAC | CTT | CTT | CGA | AGT | GTT | CAG | 1017
| CGA | CGT | CTT | TAA | TAA | TGT | CTG | GAA | GAA | GCT | TCA | CAA | GTC |
| Ala | Ala | Glu | Ile | Ile | Thr | Asp | Leu | Leu | Arg | Ser | Val | Gln |
|  | 320 |  |  |  |  | 325 |  |  |  |  | 330 |  |
| GCT | GGT | AAT | CCT | GGT | GGA | CCT | GGA | CCT | GGT | GGT | CGA | GGA | 1056
| CGA | CCA | TTA | GGA | CCA | CCT | GGA | CCT | GGA | CCA | CCA | GCT | CCT |
| Ala | Gly | Asn | Pro | Gly | Gly | Pro | Gly | Pro | Gly | Gly | Arg | Gly |
|  |  |  | 335 |  |  |  |  | 340 |  |  |  |  |
| AGA | GGT | AGA | GGT | CAA | GGC | AAC | TGG | AAC | ATG | GGA | CCA | CCT | 1095
| TCT | CCA | TCT | CCA | GTT | CCG | TTG | ACC | TTG | TAC | CCT | GGT | GGA |
| Arg | Gly | Arg | Gly | Gln | Gly | Asn | Trp | Asn | Met | Gly | Pro | Pro |
| 345 |  |  |  |  | 350 |  |  |  |  | 355 |  |  |
| GGT | GGA | TTA | CAG | GAA | TTT | AAT | TTT | ATT | GTG | CCA | ACT | GGG | 1134
| CCA | CCT | AAT | GTC | CTT | AAA | TTA | AAA | TAA | CAC | GGT | TGA | CCC |
| Gly | Gly | Leu | Gln | Glu | Phe | Asn | Phe | Ile | Val | Pro | Thr | Gly |
|  |  | 360 |  |  |  |  | 365 |  |  |  |  | 370 |
| AAA | ACT | GGA | TTA | ATA | ATA | GGA | AAA | GGA | GGT | GAA | ACC | ATA | 1173
| TTT | TGA | CCT | AAT | TAT | TAT | CCT | TTT | CCT | CCA | CTT | TGG | TGT |
| Lys | Thr | Gly | Leu | Ile | Ile | Gly | Lys | Gly | Gly | Glu | Thr | Ile |
|  |  |  |  | 375 |  |  |  |  | 380 |  |  |  |
| AAA | AGC | ATA | AGC | CAG | CAG | TCT | GGT | GCA | AGA | ATA | GAA | CTT | 1212
| TTT | TCG | TAT | TCG | GTC | GTC | AGA | CCA | CGT | TCT | TAT | CTT | GAA |
| Lys | Ser | Ile | Ser | Gln | Gln | Ser | Gly | Ala | Arg | Ile | Glu | Leu |
|  | 385 |  |  |  |  | 390 |  |  |  |  | 395 |  |
| CAG | AGA | AAT | CCT | CCA | CCA | AAT | GCA | GAT | CCT | AAT | ATG | AAG | 1251
| GTC | TCT | TTA | GGA | GGT | GGT | TTA | CGT | CTA | GGA | TTA | TAC | TTC |
| Gln | Arg | Asn | Pro | Pro | Pro | Asn | Ala | Asp | Pro | Asn | Met | Lys |
|  |  |  | 400 |  |  |  |  | 405 |  |  |  |  |
| TTA | TTT | ACA | ATT | CGT | GGC | ACT | CCA | CAA | CAG | ATA | GAC | TAT | 1290
| AAT | AAA | TGT | TAA | GCA | CCG | TGA | GGT | GTT | GTC | TAT | CTG | ATA |
| Leu | Phe | Thr | Ile | Arg | Gly | Thr | Pro | Gln | Gln | Ile | Asp | Tyr |
| 410 |  |  |  |  | 415 |  |  |  |  | 420 |  |  |
| GCT | CGG | CAA | CTC | ATA | GAA | GAA | AAG | ATT | GGT | GGC | CCA | GTA | 1329
| CGA | GCC | GTT | GAG | TAT | CTT | CTT | TTC | TAA | CCA | CCG | GGT | CAT |
| Ala | Arg | Gln | Leu | Ile | Glu | Glu | Lys | Ile | Gly | Gly | Pro | Val |
|  |  | 425 |  |  |  |  | 430 |  |  |  |  | 435 |
| AAT | CCT | TTA | GGG | CCA | CCT | GTA | CCC | CAT | GGG | CCC | CAT | GGT | 1368
| TTA | GGA | AAT | CCC | GGT | GGA | CAT | GGG | GTA | CCC | GGG | GTA | CCA |
| Asn | Pro | Leu | Gly | Pro | Pro | Val | Pro | His | Gly | Pro | His | Gly |
|  |  |  |  | 440 |  |  |  |  | 445 |  |  |  |
| GTC | CCA | GGC | CCC | CAT | GGA | CCT | CCT | GGG | CCT | CCA | GGG | CCT | 1407
| CAG | GGT | CCG | GGG | GTA | CCT | GGA | GGA | CCC | GGA | GGT | CCC | GGA |
| Val | Pro | Gly | Pro | His | Gly | Pro | Pro | Gly | Pro | Pro | Gly | Pro |
|  | 450 |  |  |  |  | 455 |  |  |  |  | 460 |  |
| GGA | ACT | CCA | ATG | GGA | CCA | TAC | AAC | CCT | GCA | CCT | TAT | AAT | 1446
| CCT | TGA | GGT | TAC | CCT | GGT | ATG | TTG | GGA | CGT | GGA | ATA | TTA |
| Gly | Thr | Pro | Met | Gly | Pro | Tyr | Asn | Pro | Ala | Pro | Tyr | Asn |
|  |  |  | 465 |  |  |  |  | 470 |  |  |  |  |
| CCT | GGA | CCA | CCA | GGC | CCG | GCT | CCT | CAT | GGT | CCT | CCA | GCC | 1485
| GGA | CCT | GGT | GGT | CCG | GGC | CGA | GGA | GTA | CCA | GGA | GGT | CGG |
| Pro | Gly | Pro | Pro | Gly | Pro | Ala | Pro | His | Gly | Pro | Pro | Ala |
| 475 |  |  |  |  | 480 |  |  |  |  | 485 |  |  |
| CCA | TAT | GCT | CCC | CAG | GGA | TGG | GGA | AAT | GCA | TAT | CCA | CAC | 1524
| GGT | ATA | CGA | GGG | GTC | CCT | ACC | CCT | TTA | CGT | ATA | GGT | GTG |
| Pro | Tyr | Ala | Pro | Gln | Gly | Trp | Gly | Asn | Ala | Tyr | Pro | His |
|  |  | 490 |  |  |  |  | 495 |  |  |  |  | 500 |
| TGG | CAG | CAG | CAG | GCT | CCT | CCT | GAT | CCA | GCT | AAG | GCA | GGA | 1563
| ACC | GTC | GTC | GTC | CGA | GGA | GGA | CTA | GGT | CGA | TTC | CGT | CCT |
| Trp | Gln | Gln | Gln | Ala | Pro | Pro | Asp | Pro | Ala | Lys | Ala | Gly |
|  |  |  |  | 505 |  |  |  |  | 510 |  |  |  |
| ACG | GAT | CCA | AAT | TCA | GCA | GCT | TGG | GCT | GCT | TAT | TAC | GCT | 1602
| TGC | CTA | GGT | TTA | AGT | CGT | CGA | ACC | CGA | CGA | ATA | ATG | CGA |
| Thr | Asp | Pro | Asn | Ser | Ala | Ala | Trp | Ala | Ala | Tyr | Tyr | Ala |
|  | 515 |  |  |  |  | 520 |  |  |  |  | 525 |  |
| CAC | TAT | TAT | CAA | CAG | CAA | GCA | CAG | CCA | CCA | CCA | GCA | GCC | 1641
| GTG | ATA | ATA | GTT | GTC | GTT | CGT | GTC | GGT | GGT | GGT | CGT | CGG |
| His | Tyr | Tyr | Gln | Gln | Gln | Ala | Gln | Pro | Pro | Pro | Ala | Ala |
|  |  |  | 530 |  |  |  | 535 |  |  |  |  |  |
| CCT | GCA | GGT | GCA | CCA | ACT | ACA | ACT | CAA | ACT | AAT | GGA | CAA | 1680
| GGA | CGT | CCA | CGT | GGT | TGA | TGT | TGA | GTT | TGA | TTA | CCT | GTT |
| Pro | Ala | Gly | Ala | Pro | Thr | Thr | Thr | Gln | Thr | Asn | Gly | Gln |
| 540 |  |  |  |  | 545 |  |  |  |  | 550 |  |  |
| GGA | GAT | CAG | CAG | AAT | CCA | GCC | CCA | GCT | GGA | CAG | GTT | GAT | 1719
| CCT | CTA | GTC | GTC | TTA | GGT | CGG | GGT | CGA | CCT | GTC | CAA | CTA |
| Gly | Asp | Gln | Gln | Asn | Pro | Ala | Pro | Ala | Gly | Gln | Val | Asp |
|  |  | 555 |  |  |  | 560 |  |  |  |  |  | 565 |
| TAT | ACC | AAG | GCT | TGG | GAA | GAG | TAC | TAC | AAG | AAA | ATG | GGG | 1758
| ATA | TGG | TTC | CGA | ACC | CTT | CTC | ATG | ATG | TTC | TTT | TAC | CCC |
| Tyr | Thr | Lys | Ala | Trp | Glu | Glu | Tyr | Tyr | Lys | Lys | Met | Gly |
|  |  |  |  | 570 |  |  |  |  | 575 |  |  |  |

-continued

| CCA | ATA | ATA | AGA | AGT | GGA | CAA | TAC | AGT | ATT | TGC | TTC | 1794 |
| GGT | TAT | TAT | TCT | TCA | CCT | GGT | ATG | TCA | TAA | ACG | AAG | |
| Pro | Ile | Ile | Arg | Ser | Gly | Gln | Tyr | Ser | Ile | Cys | Phe | |
| | 580 | | | | | 585 | | | | | 590 | |
| AGGAATTCC | | | | | | | | | | | | 1803 |
| TCCTTAAGG | | | | | | | | | | | | |

The amino acid sequence for the protein encoded by the cDNA sequence for clone 31-10 can be found in SEQ ID NO:8.

The following examples are for illustration only, and should not be used to limit the scope of the invention.

EXAMPLE 1

The cloned cDNA encodes a protein with FUSE binding activity, referred to as DROME or FUSE binding protein ("FBP"). The coding region contained in the HL60 clones was expressed as a fusion protein in bacteria, purified from extracts and tested with electrophoretic mobility shift assays (EMSAs) for binding to an oligonucleotide containing the FUSE site. Recombinant fusion protein (GST-FBP) bound effectively to the FUSE oligonucleotide.

The open reading frame present in the HL60-1 and HL60-2 clones (amino acid residues 145 to 511) was expressed as a Glutathione-S-transferase fusion protein (GST-FBP) in the pGEX system. The inserts from the HL60-1 and HL60-2 clones were spliced together and the open reading frame region subcloned into the Sma I site of the pGEX-2T plasmid (AMARAD Corp.; D. B. Smith and K. S. Johnson, Gene. 67,31 (1988)) to express a GST-FBP fusion protein. Recombinant protein was purified from E. coli extracts on a glutathione-agarose matrix (Sigma Chemical Co.), GST alone was prepared from a pGEX-2T plasmid with no insert in a similar manner. Fusion proteins were eluted with 20 mM glutathione, checked for purity, correct size and concentration with SDS PAGE.

Purified recombinant proteins were incubated with double stranded, $^{32}$P labeled, oligonucleotide (Probe) in the presence or absence of the indicated quantity of unlabeled, double stranded oligonucleotide as competitor, and subjected to EMSA. (M. Fried and D. M. Crothers, Nucleic Acids Res. 9, 6505 (1981)).

DNA binding assays were performed with an equivalent amount of GST-FBP or GST alone incubated in 25 mM Tris, 200 mM Glycine, 1mM EDTA, 0.5 mg/ml BSA, 0.1% Tween20, 10% glycerol, 100 µg/ml poly(dI:dC), and 0.2 ng of labeled probe. The probe was prepared by annealing two complementary synthetic oligonucleotides and 5' end labeling with T$_4$ polynucleotide kinase in the presence of γ-$^{32}$P-ATP. The top strand of the FUSE oligonucleotide was 5'-GATCACAAAATAAAAATCCCGAGGGAATATAG-3' (SEQ ID NO:11). The top strand of Mut A was 5'-GATCACAAAAAATCCGAGGAATATAG-3' (SEQ ID NO:12) (lower case indicates changes from FUSE oligomer sequence). The top strand of CRE was 5'-GATCTGACGTCATGACTGACGTCATGACTGACGT-CATCA-3' (SEQ ID NO:13). The top strand of CTE was 5'-AATTCTCCTCCCCACCTTCCCCACCTCCCCA-3' (SEQ ID NO:14). Reaction mixtures were incubated 30 minutes at room temperature and protein-DNA complexes resolved by electrophoresis on a 4.2% acrylamide gel in 25 mM Tris, 200 mM Glycine, 1 mM EDTA buffer.

Figure 3A:
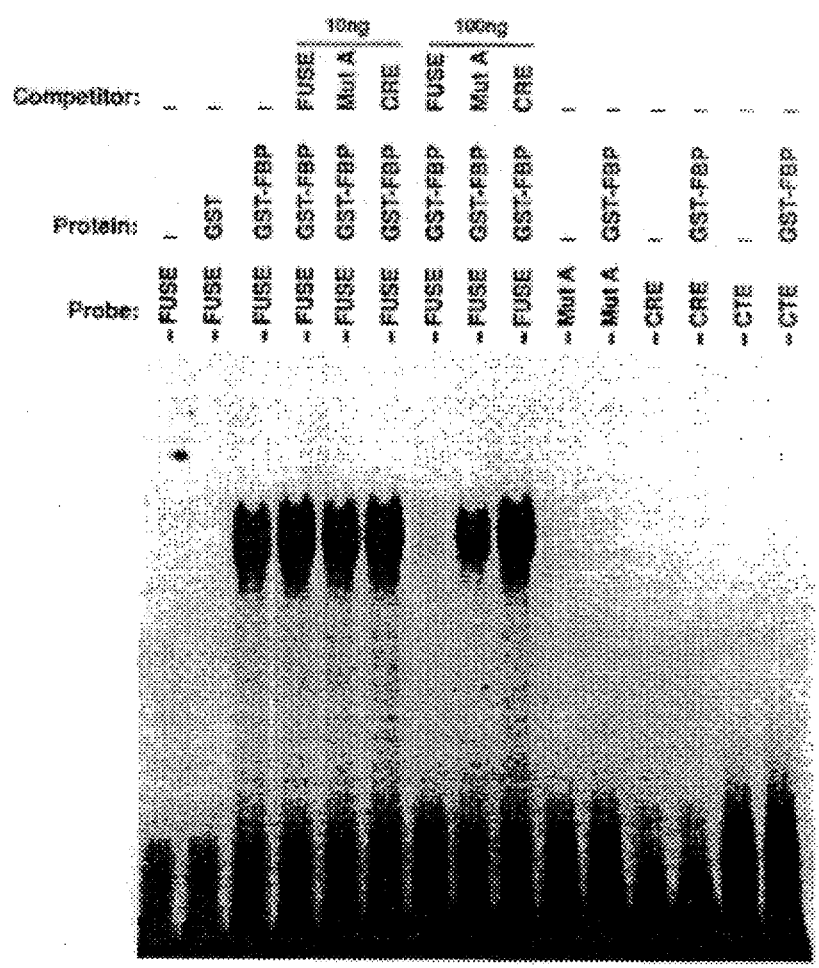
FIGS. 3A and 3B depict DNA binding assay radiographs showing that recombinant FBP binds specifically to the far upstream element.

Radioactive DNA and DNA-protein complexes were visualized by autoradiography (FIG. 3A). Glutathione-S-transferase (GST) alone did not bind to the probe. Competitor oligonucleotides were as follows: Mut A, a mutant FUSE oligonucleotide with 17 residues covering the binding site changed; CRE, cAMP response element; CTE, CT element in c-myc 5' flanking region.

Figure 3B:
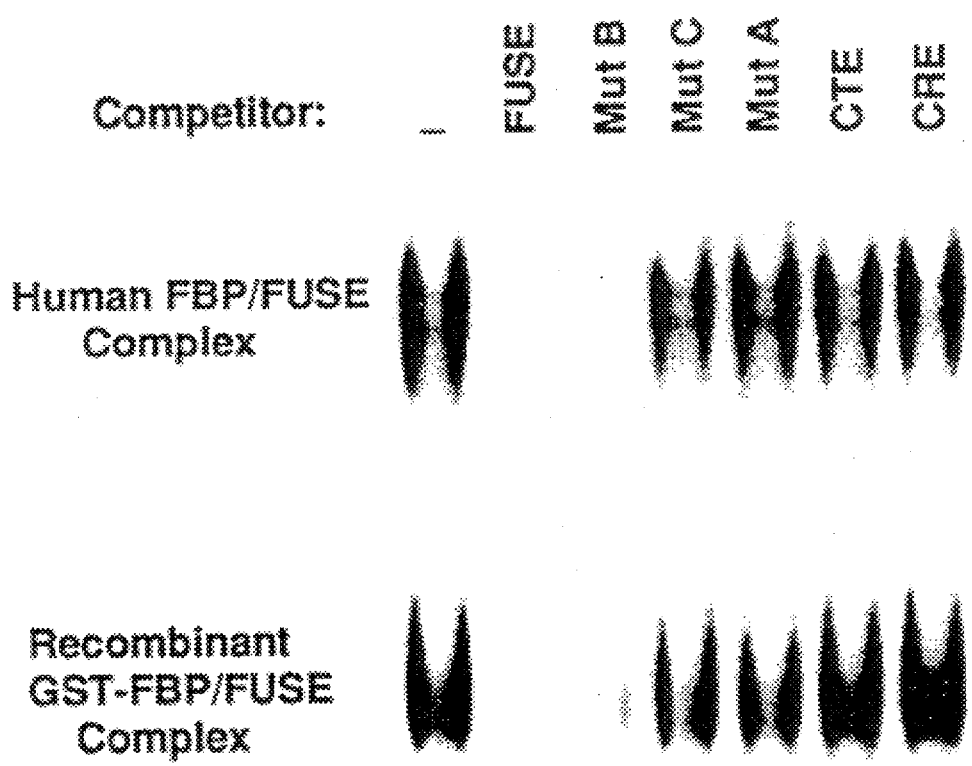

Recombinant FBP and purified human FBP were also demonstrated to display similar DNA binding specificity. Full length GST-FBP and human FBP purified from HL60 cells by oligo-affinity chromatography were assayed for FUSE binding using EMSA. The DNA-protein complexes formed by human FBP in the presence of 25ng of the indicated non-radioactive competitors, visualized by autoradiography, are shown in the upper panel of FIG. 3B. The lower panel of FIG. 3B shows recombinant GST-FBP binding the FUSE probe in the presence of 25 ng of the same competitors. Competitor oligonucleotides are the same as in (A) with the addition of Mut B and Mut C, each with a different mutation in the FUSE sequence. The top strand of Mut B was 5'-GATCACAAAATAAAAAATggacgccGAATATAG-3' (SEQ ID NO:15) and the top strand of Mut C was 5' AATTCTCCTCCCACCTCCCACCTCCCA-GATCACAActacgtgctaggCGAGGGAATATAG-3' (SEQ ID NO:16).

Recombinant fusion protein also failed to bind to the nonhomologous oligonucleotides when they were used as radioactive probes. The full length recombinant protein, and purified human FBP shared the same DNA binding specificity as indicated by challenging their binding to FUSE with a panel of competitors (FIG. 3B). An excess of cold FUSE significantly reduced binding of human and recombinant FBP to the radioactive probe; the same amount of the Mut B oligo which has minor changes in the FUSE sequence, bound both as well; but more divergent oligonucleotides did not significantly compete for binding to either protein.

EXAMPLE 2

Figure 4:
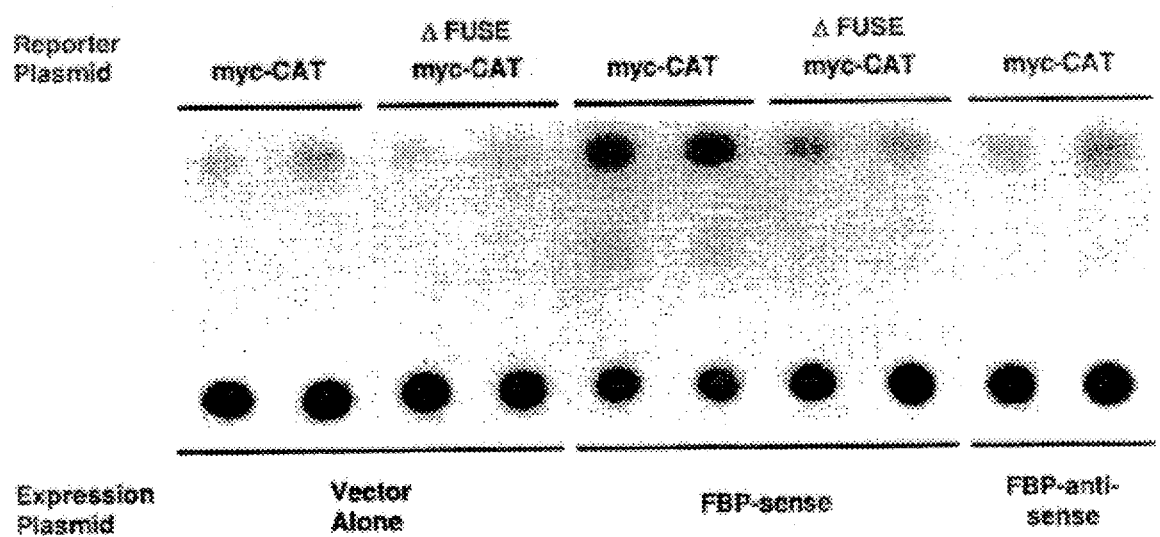
FIG. 4 shows assays depicting recombinant FBP activated expression of a chloramphenicol acetyltransferase (CAT) gene under the control of human c-myc regulatory sequence.

Recombinant FBP activated expression of a chloramphenicol acetyltransferase (CAT) gene under the control of human c-myc regulatory sequence was tested in co-transection experiments (FIG. 4).

Full length FBP was inserted into an expression vector downstream from the cytomegalovirus enhancer/promoter in both the sense and anti-sense orientations. These plasmids or the expression vector alone were transfected into U937 cells with another vector containing a CAT gene under the control of myc regulator sequence (myc-CAT) or the reporter plasmid with the FUSE site deleted (ΔFUSE myc-CAT). The myc-CAT and ΔFUSE myc-CAT reporter plasmids are derivatives of pMP CAT (M. Avigan, B. Strober, and D. Levens, J. Biol. Chem., 265,18538 (1990)) with the deletion of a 580 bp Nsi I fragment from position −669 to −1249 relative to the myc P1 promoter. The Nsi I deletion results in more consistent CAT expression without disrupting FUSE mediated activation. The ΔFUSE myc-CAT plasmid was produced from pMP CAT by cutting the parent plasmid at the Ava I site located in the FUSE element, partial digestion with mung bean exonuclease (Bethesda Research Labs) and religation. The DNA sequence of the deleted plasmid revealed that 68 nucleotides between position −1493 and −1561 relative to myc P1 were removed, completely deleting the FUSE element.

U937 cells ($5 \times 10^6$) were electroporated (Cell-porator, BRL, 200V, 1180 μF) with 10 μg of each plasmid in 250 μl of RPMI supplemented with 10% fetal calf serum. Transfected cells were added to 8 ml additional medium and incubated 48 hours before harvesting for CAT assays. (C. M. Gorman, L. F. Moffat, B. H. Howard, *Mol. Cell. Biol.* 2, 1044 (1982)). The same quantity of protein (Bradford method) was assayed for each extract. Two independent transfections are shown for each plasmid combination.

In the presence of the FBP expression plasmid (FBP-sense), the FUSE containing myc-CAT plasmid (myc-CAT) gave a 5-fold higher level of CAT activity than in the presence of the expression vector alone. In contrast, this level of stimulation did not occur when the reporter plasmid had a 68 bp deletion that eliminated the FUSE site (ΔFUSE myc-CAT) nor when the expression plasmid contained the FBP cDNA in the reverse orientation (FBP-antisense). The minor increase in the ΔFUSE myc-CAT expression with FBP co-transection could be due to secondary binding sites present in the myc regulatory sequence.

FBP shows no significant homology to known DNA binding motifs in a search against the GenBank databases, however the primary amino acid sequence of FBP has distinct structural features which could constitute a DNA binding domain, as well as other features with potential functional significance.

EXAMPLE 3

A Pustell matrix self-comparison of FBP revealed three domains in the primary amino acid sequence, each containing internally repeated sequences.

Figure 5A:
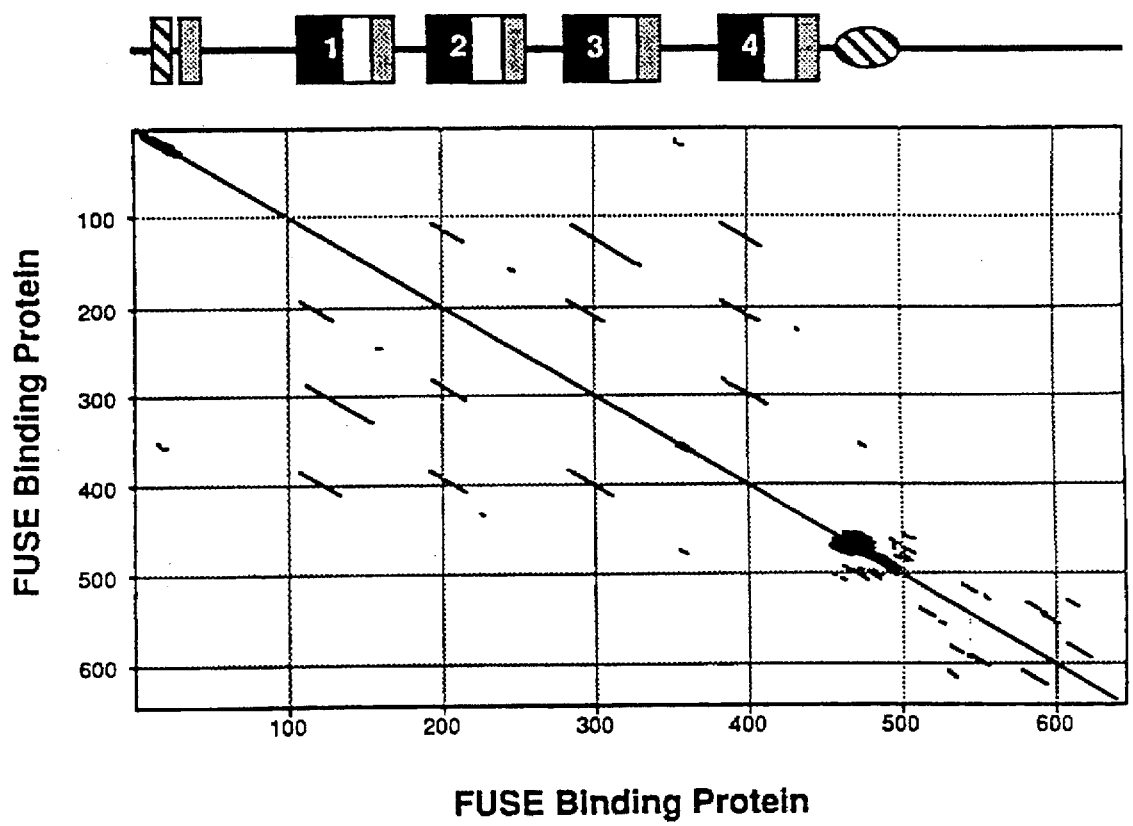
FIGS. 5A–5C show the structural features of the primary amino acid sequence of FBP.

The Pustell matrix (J. Pustell, F. C. Kafatos, N. A. R. 10, 4765 (1982); W. R. Pearson, *Meth. Enzymol.* 183, 63 (1990); MacVector software, International Biotechnologies, Inc.) revealed the repeated sequences in the three domains of FBP. The repeated glycines in the N-terminal domain, the four copies of the FBP repeat in the central domain, the proline/glycine rich segment and the WAAYY (where W is Trp, A is Ala and Y is Tyr) repeat in the C-terminal domain all score as diagonals. A window size of 20 residues and a minimum score of 35% were used for this analysis. The diagram above the box in FIG. 5A symbolizes the structures in FBP: striped fill indicates glycine rich segments, the solid boxes indicate the FBP repeats, and the shaded boxes represent amphipathic helices.

The amino-terminal domain is comprised of 106 amino acids featuring a string of 11 repeated glycine residues and the first of 5 predicted amphipathic alpha helices found in FBP. Following the helix, residues 63 to 106 are enriched for glutamine (16%) relative to the whole protein (9%).

Figures 5B, 5C:
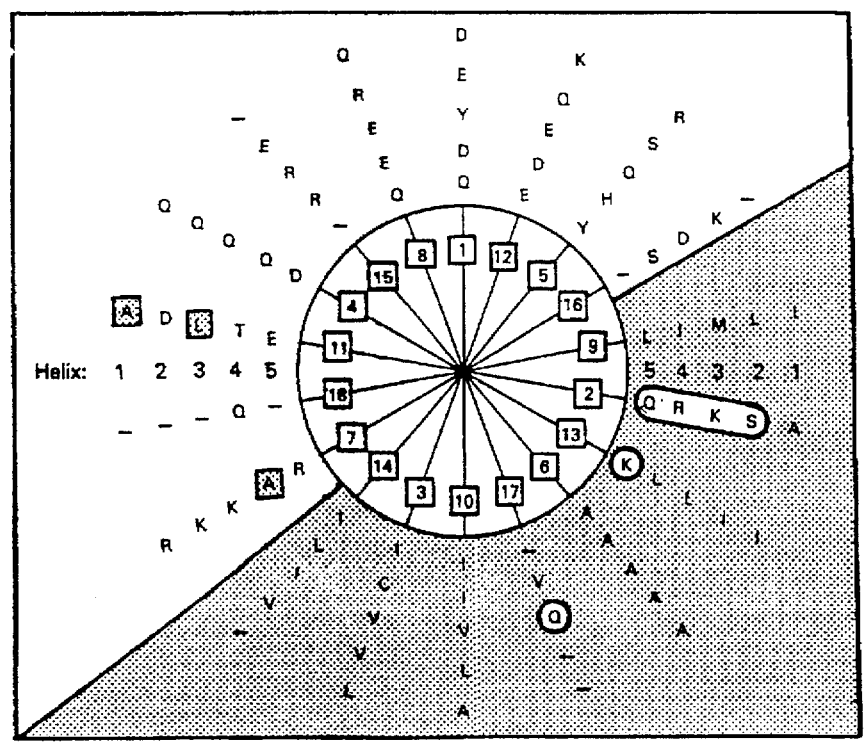

The central and largest FBP domain contains structures sufficient for sequence specific binding because a recombinant protein comprised of only this domain bound DNA specifically. The central domain is made up of four evenly spaced units each unit containing (1) a highly conserved 30 residue segment termed here the FBP repeat (FIG. 5B), followed by (2) a potential amphipathic alpha helix (FIG. 5C). Each FBP repeat is comprised of three structures in sequential order: a region of predicted β-sheet, separated by a turn at conserved glycines 13 and 14, from a segment of alpha-helix as predicted by Chou-Fasman and Robson-Garnier analysis. (P. Y. Chou and G. D. Fasman, "Prediction of the secondary structure of proteins from their amino acid sequence." *Adv. Enzymol. Relat. Areas Mol. Biol.* 47:45–148 (1978); B. Robson and E. Suzuki, "Conformational properties of amino acid residues in globular proteins." *J. Mol. Biol.* 107:327–356 (1976); J. Garnier, D. J. Osguthorpe, and B. Robson, "Analysis of the accuracy and implications of simple methods for predicting the secondary structure of globular proteins." *J. Mol. Biol.* 120:97–120 (1978). Analysis was performed with MacVector Software (International Biotechnologies, Inc.)). The FBP repeats are found at amino acid positions 107-136, 192-221, 282-311 and 383-412.

The invariant glycine at position 25 may not disrupt helix formation due to the hydrophilic character of neighboring residues in the predicted helix. (L. Serrano, J. L. Neira, J. Sancho, and A. R. Fersht, "Effect of alanine versus glycine in alpha-helices on protein stability." *Nature*, 356:453–455 (1992)). This sheet-turn-helix pattern evokes the DNA-binding domain of the papilloma virus E2 protein. (R. S. Hegde, S. R. Grossman, L. A. Laimins, and P. Sigler, "Crystal structure at 1.7 Å of the bovine papillomavirus-1 E2 DNA-binding domain bound to its DNA target." *Nature* 359:505–512 (1992)). An amphipathic helix follows each repeat after a spacer of 18-21 residues. The amphipathic helices are found at amino acid positions 155-170, 242-258, 330-347 and 434-447. The amphipathic character of the four central domain helices extends uniformly over their 16-18 residue lengths with the exception of hydrophilic residues at position 2 (FIG. 5C). The lack of a hydrophobic residue at this position deviates from the heptad repeat pattern shown to be important in coiled-coiled interactions. (F. H. C. Crick, *Nature*. 170, 882 (1952)). The helices are not flanked by basic regions as in basic-coiled-coil (S. C. Harrison, "Structural taxonomy of DNA-binding proteins." *Nature*, 353:715–719 (1991); W. H. Landschulz, P. F. Johnson, and S. L. McKnight. *Science*, 240:1759–1764 (1988)) or helix-loop-helix motifs. (C. Murre, P. Schonleber McCaw, and D. Baltimore, "A new DNA binding and dimerization motif in immunoglobulin enhancer binding, daughterless, MyoD, and myc proteins." *Cell* 56:777–783 (1989)). Thus the repeat-helix unit found in the central domain of FBP does not resemble known DNA binding motifs.

The C-terminal domain is separated from the central domain by a highly flexible, proline-glycine rich segment. This domain is also glutamine rich (22/140=15.7% from amino acid 505 to the C-terminal) and tyrosine rich (13/140=9.3%) including repeated tyrosine dyad motifs some of which conform to a tyrosine phosphorylation recognition site. (J. A. Cooper, F. S. Esch, S. S. Taylor, and T. Hunter, "Phosphorylation sites in enolase and lactate dehydrogenase utilized by tyrosine protein kinases in vivo and in vitro." *J. Biol. Chem.* 259:7835–7841 (1984)).

EXAMPLE 4

To define a minimum DNA binding motif within the central domain, further truncations were constructed as well as short insertions to disrupt the predicted structures. Mutant constructs were expressed as bacterial fusion proteins, purified and tested for DNA binding to the FUSE oligonucleotide.

The plasmid which encodes the 278-511 mutant was constructed by inserting an EcoR I-Sac I fragment from the HL60-2 clone into the pGEX-1 vector. The fusion protein contains amino acids 278-511 of FBP plus the residues KEIEQKVQE (SEQ ID NO:17) (where K is Lys, E is Glu, I is Ile, Q is Gln, and V is Val) at the carboxyterminal end stopping at a termination codon unique to the HL60-2 clone. The 278-474 encoding plasmid was constructed from the 278-511 plasmid by inserting a 12 bp double stranded oligonucleotide with the sequence TTAGTTAACTAA (SEQ ID NO:18) into an Sfi I site. This oligonucleotide encodes stop codons in all 3 reading frames so that a truncated protein is produced. The 278-372 encoding plasmid was similarly constructed by inserting the termination oligonucleotide into a Dra III site. The 298-511 encoding plasmid was constructed from the 278-511 plasmid by deleting a fragment between the BamH I site in the pGEX vector and a Bcl I in the FBP cDNA.

Figure 6A:
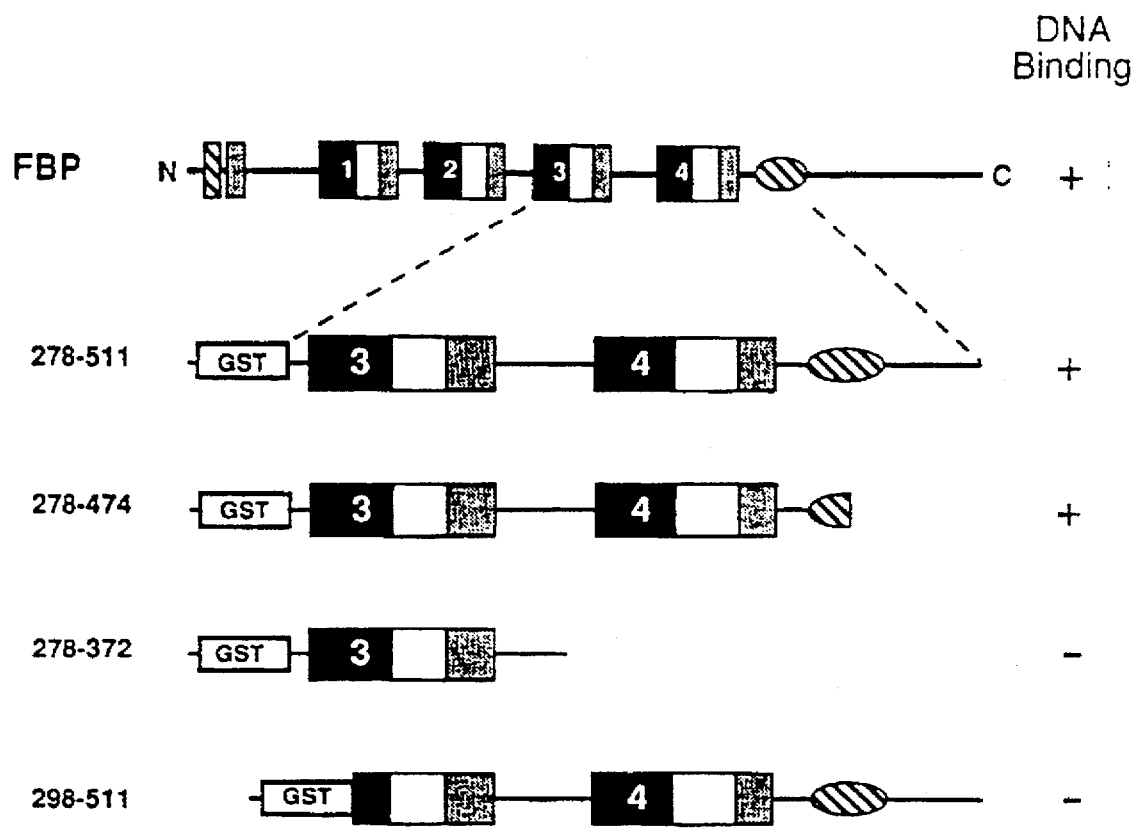
FIGS. 6A–6C illustrates a mutational analysis of the minimum DNA binding domain of recombinant FBP.

The ability of each construct to bind (+) or failure to bind (−) the FUSE DNA sequence is indicated at the right in FIG. 6A. The open boxes labeled "GST" indicate the glutathione-S-transferase fragment present in the fusion proteins. Other symbols are the same as in FIG. 5A.

Figure 6B:
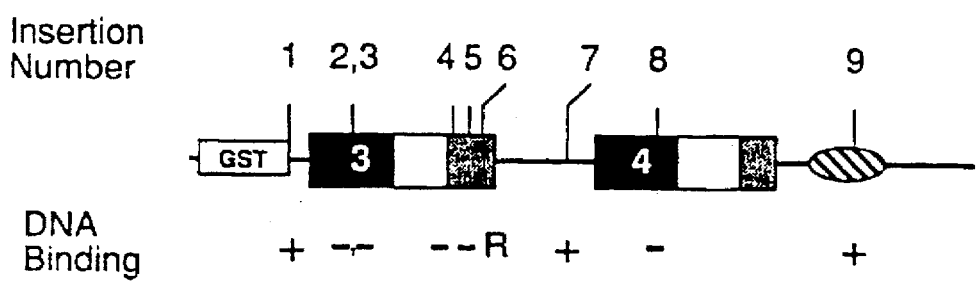
Figure 6C:
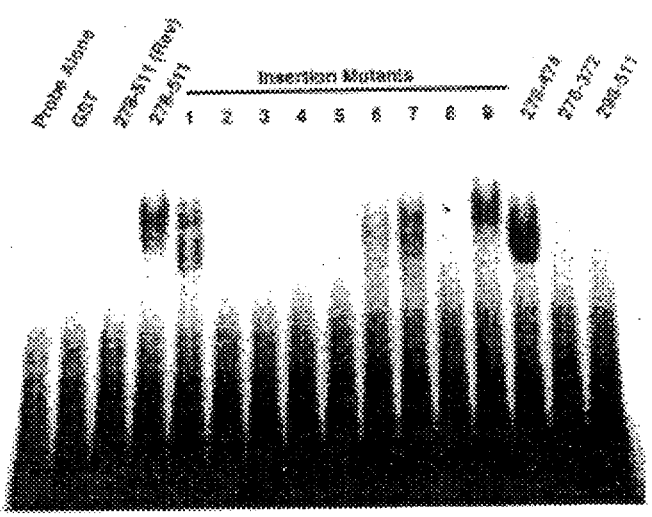

The truncated protein containing the third and fourth units of the central domain and the proline/glycine rich region (278-511, FIG. 6A) bound DNA with the same specificity as full length DROME or FPB (FIG. 6C). A truncation mutant lacking a portion of the proline-glycine rich region (278-474) still bound DNA. In contrast, the removal of FBP repeat 4 and the rest of the C-terminus in a mutant with a larger truncation (278-372) or removal of the NH2-terminal portion of repeat 3 (298-511) abrogated binding. These truncations suggest that at least two intact FBP repeat-helix units are required to constitute a DNA binding domain and that at least half of the Pro-Gly region is not required.

EXAMPLE 5

Insertion mutants further demonstrated the importance of two repeat-helix units for DNA binding. Three to six amino acids were introduced at eight positions throughout the 278-511 construct (FIG. 6B) without altering the reading frame.

The insertion mutants were constructed by cutting the 278-511 plasmid at restriction sites, treating the ends with the large fragment of DNA polymerase I (if not already blunt) and inserting linkers of 8, 10 or 12 base pairs. The appropriate length was chosen to insert a small number of amino acids but restore the original reading frame leaving the rest of the sequence unchanged. Insertion mutant 1 had the amino acids ArgIleArg added between GST and the FBP polypeptide. Mutant 2 had residues IleGlySerArgIleArg (SEQ ID NO:19) added after the Met at position 297 in FBP, mutant 3 had IleArgIleArg (SEQ ID NO:20) added after Met297. Mutant 4 had ProArgIleArgGlu (SEQ ID NO:21) added while deleting Gln at amino acid 333. Mutant 5 had GlyIlePro added after amino acid 336. Mutant 6 had GlyIleProArg (SEQ ID NO:22) added after amino acid 343. Mutant 7 ArgIleArg added after amino acid 373. Mutant 8 had ArgAspProAla (SEQ ID NO:23) added while deleting GlnSer after amino acid 404. Mutant 9 had ArgGlySerGly (SEQ ID NO:24) inserted while deleting Pro after amino acid 475. All constructs were confirmed by DNA sequencing. The DNA binding property of each insertion mutant is indicated by a +, − or R (reduced binding) below the insertion site.

An insertion at the junction between GST and the FBP sequence (insertion mutant number 1) does not effect binding. Neither do insertions into the region between helix 4 and repeat 4 (number 7) or the Pro-Gly region (number 9). In contrast, insertions 2 and 3 in repeat three, insertions 4 and 5 in helix four, and insertion 8 in repeat four all resulted in mutant proteins failing to bind DNA. Insertion number 6, near the end of helix four, reduced but did not eliminate binding.

The combined evidence from RNA expression, DNA binding specificity and transection experiments indicate the presence of a human FUSE binding protein (referred to as FBP or DROME) that activates myc expression. FBP binds DNA through a novel, repeated motif. The presence of four sets of the repeat-helix unit in FBP, when only two are required for FUSE binding, suggests that this protein has the potential to form at least two binding sites. A dual binding capability may be important for its cellular function. For example, binding of FBP could facilitate DNA looping which stimulates the interaction of distant elements, a mechanism consistent with the far upstream location and the requirement for additional regulatory sequence to observe the stimulatory effect of the FUSE site.

EXAMPLE 6

The purified FUSE binding protein is also useful in the production of monoclonal antibodies. Thus, a mouse is injected with purified FUSE binding protein, or a fragment thereof, which activates a number of B-lymphocytes in the mouse which produce antibodies against the protein. The mouse is sacrificed and spleen lymphoid cells, containing large quantities of these B-lymphocytes, are isolated and tested to assure production of antibody to FUSE binding protein. The lymphocytes producing antibody to FUSE binding protein are then fused with mouse plasmacytoma cells, ensuring a reproducible source of monoclonal antibody (Kohler, G. and Milstein, C. *Nature*, 256:495–97 (1975)). These antibodies, or fragments thereof, can then be used to detect and quantitate the FUSE binding protein.

EXAMPLE 7

The anti-sense sequence for the FUSE binding protein cDNA is useful therapeutically to arrest cell development in a target area of uncontrolled cell growth. An expression vector or oligonucleotide is constructed incorporating the anti-sense sequence of the FUSE binding protein cDNA. The oligonucleotide or vector is then incorporated into the cells of the target area, and acts to antagonize or block expression of the FUSE binding protein, inhibiting cell division and proliferation.

This is effective, for example, in arresting tumor cell growth, or an unwarranted immune response (i.e., arresting B- or T-lymphocytes).

The invention has been described in detail with particular reference to a preferred embodiment thereof, but it will be understood that the invention is capable of other and different embodiments. As is readily apparent to those skilled in the art, variations and modifications can be effected within the spirit and scope of the invention. Accordingly, the foregoing disclosure, description, and figures are for illustrative purposes only, and do not in any way limit the invention, which is defined only by the claims.

SEQUENCE LISTING ( 1 ) GENERAL INFORMATION:

( i i i ) NUMBER OF SEQUENCES: 24

( 2 ) INFORMATION FOR SEQ ID NO: 1:

( i ) SEQUENCE CHARACTERISTICS:
        ( A ) LENGTH: 2384
        ( B ) TYPE: Nucleic acid
        ( C ) STRANDEDNESS: Double
        ( D ) TOPOLOGY: Unknown ( i i ) MOLECULE TYPE: cDNA ( i i i ) HYPOTHETICAL: No ( i v ) ANTI-SENSE: YES ( v i ) ORIGINAL SOURCE:
        ( A ) ORGANISM: Human
        ( H ) CELL LINE: HL60

( i x ) FEATURE:
        ( D ) OTHER INFORMATION: 473 bp
        variable region where R is A or G.

( x i ) SEQUENCE DESCRIPTION: SEQ ID NO: 1:

```
GCGGCAGCGG CTCTTATAGT GCAACC ATG GCA GAC TAT TCA ACA        44
GTG CCT CCC CCC TCT TCT GGC TCA GCT GGT GGC GGT GGT         83
GGC GGT GGT GGT GGA GGA GTT AAC GAC GCT TTC AAA            122
GAT GCA CTG CAG AGA GCC CGG CAG ATT GCA GCA AAA ATT        161
GGA GGT GAT GCA GGG ACA TCA CTG AAT TCA AAT GAC TAT        200
GGT TAT GGG GGA CAA AAA AGA CCT TTA GAA GAT GGA GAT        239
CAA CCA GAT GCT AAG AAA GTT GCT CCT CAA AAT GAC TCT        278
TTT GGA ACA CAG TTA CCA CCG ATG CAT CAG CAG CAA AGC        317
AGA TCT GTA ATG ACA GAA GAA TAC AAA GTT CCA GAT GGA        356
ATG GTT GGA TTC ATA ATT GGC AGA GGA GGT GAA CAG ATC        395
TCA CGC ATA CAA CAG GAA TCT GGA TGC AAA ATA CAG ATA        434
GCT CCT GAC AGT GGT GGC CTT CCA GAA AGG TCC TGT ATR        473
TTA ACT GGA ACA CCT GAA TCT GTC AGT CA GCA AAA CGG         512
TTA CTG GAC CAG ATT GTT GAA AAA GGA AGA CCA GCT CCT        551
GGC TTC CAT CAT GGC GAT GGA CCG GGA AAT GCA GTT CAA        590
GAA ATC ATG ATT CCA GCT AGC AAG GCA GGA TTA GTC ATT        629
GGA AAA GGG GGA GAA ACT ATT AAA CAG CTT CAG GAA CGG        668
GCT GGA GTT AAA ATG GTT ATG ATT CAA GAC GGG CCG CAG        707
AAC ACT GGT GCT GAC AAA CCT CTT AGG ATT ACA GGA GAC        746
CCA TAT AAA GTT CAA CAA GCC AAG GAA ATG GTG TTA GAG        785
TTA ATT CGT GAT CAA GGC GGT TTC AGA GAA GTT CGG AAT        824
GAG TAT GGG TCA AGA ATA GGA GGA AAT GAA GGG ATA GAT        863
GTC CCC ATT CCA AGA TTT GCT GTT GGC ATT GTA ATA GGA        902
AGA AAT GGA GAG ATG ATC AAA AAA ATA CAA AAT GAT GCT        941
```

```
GGT GTT CGC ATT CAG TTT AAG CCA GAT GAT GGG ACA ACA      980
CCC GAA AGG ATA GCA CAA ATA ACA GGA CCT CCA GAC CGA     1019
TGT CAA CAT GCT GCA GAA ATT ATT ACA GAC CTT CTT CGA     1058
AGT GTT CAG GCT GGT AAT CCT GGT GGA CCT GGA CCT GGT     1097
GGT CGA GGA AGA GGT AGA GGT CAA GGC AAC TGG AAC ATG     1136
GGA CCA CCT GGT GGA TTA CAG GAA TTT AAT TTT ATT GTG     1175
CCA ACT GGG AAA ACT GGA TTA ATA ATA GGA AAA GGA GGT     1214
GAA ACC ATA AAA AGC ATA AGC CAG CAG TCT GGT GCA AGA     1253
ATA GAA CTT CAG AGA AAT CCT CCA CCA AAT GCA GAT CCT     1292
AAT ATG AAG TTA TTT ACA ATT CGT GGC ACT CCA CAA CAG     1331
ATA GAC TAT GCT CGG CAA CTC ATA GAA GAA AAG ATT GGT     1370
GGC CCA GTA AAT CCT TTA GGG CCA CCT GTA CCC CAT GGG     1409
CCC CAT GGT GTC CCA GGC CCC CAT GGA CCT CCT GGG CCT     1448
CCA GGG CCT GGA ACT CCA ATG GGA CCA TAC AAC CCT GCA     1487
CCT TAT AAT CCT GGA CCA CCA GGC CCG GCT CCT CAT GGT     1526
CCT CCA GCC CCA TAT GCT CCC CAG GGA TGG GGA AAT GCA     1565
TAT CCA CAC TGG CAG CAG CAG GCT CCT CCT GAT CCA GCT     1604
AAG GCA GGA ACG GAT CCA AAT TCA GCA GCT TGG GCT GCT     1643
TAT TAC GCT CAC TAT TAT CAA CAG CAA GCA CAG CCA CCA     1682
CCA GCA GCC CCT GCA GGT GCA CCA ACT ACA ACT CAA ACT     1721
AAT GGA CAA GGA GAT CAG CAG AAT CCA GCC CCA GCT GGA     1760
CAG GTT GAT TAT ACC AAG GCT TGG GAA GAG TAC TAC AAG     1799
AAA ATG GGT CAG GCA GTT CCT GCT CCG ACT GGG GCT CCT     1838
CCA GGT GGT CAG CCA GAT TAT AGT GCA GCC TGG GCT GAG     1877
CAT TAT AGA CAA CAA GCA GCC TAT TAT GCC CAG ACA AGT     1916
CCC CAG GGA ATG CCA CAG CAT CCT CCA GCA CCT CAG GGC     1955
CAA TAA TAA GAAGTGGACA ATACAGTATT TGCTTCATTG            1994
TGTGGGGGAA AAAAACCTTT GTTAAATATA TGGATGCAGA             2034
CGACTTGATG AAGATCTTAA TTTTGTTTTT GGTTTAAAAT             2074
AGTGTTTCCT TTTTTTTTTT TTTTTTTTG AAAATGTACA              2114
AAATATCTAT CACTACTGAT AGGAGGTTAA TATTTCTGTG             2154
TAGAAATGAA AATTGGTTTG TTTTAGTAT TTAGTGTAGA              2194
TGTACACATT CCAGCAAATG TATTTGCAAT TATGTGGTTG             2234
ATGCTTTGTG ATATAAATGT ACTTTTCAA TGTATACTTT              2274
CACTTTCCAA ATGCCTGTTT TGTGCTTTAC AATAAATGAT             2314
ATGAAACCTC AAAAAAAAAA AAAAAAAAAA AAAAAAAAAA             2354
AAAAAAAAAA AAAAAAAAAA AAAAAAAAA                         2384
```

( 2 ) INFORMATION FOR SEQ ID NO: 2:

( i ) SEQUENCE CHARACTERISTICS:
  ( A ) LENGTH: 644
  ( B ) TYPE: Amino Acid ( C ) STRANDEDNESS: Single
( D ) TOPOLOGY: Unknown ( i i ) MOLECULE TYPE: Peptide/Protein ( i i i ) HYPOTHETICAL: No ( v i ) ORIGINAL SOURCE:
    ( A ) ORGANISM: Human
    ( H ) CELL LINE: HL60

( i x ) FEATURE:
    ( D ) OTHER INFORMATION:
        Amino Acid 149 (Xaa) is Met or Ile ( x i ) SEQUENCE DESCRIPTION: SEQ ID NO: 2:

```
Met Ala Asp Tyr Ser Thr Val Pro Pro Ser Ser Gly
 1               5                  10
Ser Ala Gly Gly Gly Gly Gly Gly Gly Gly Gly Gly
    15                  20                  25
Val Asn Asp Ala Phe Lys Asp Ala Leu Gln Arg Ala Arg
             30              35
Gln Ile Ala Ala Lys Ile Gly Gly Asp Ala Gly Thr Ser
 40              45                  50
Leu Asn Ser Asn Asp Tyr Gly Tyr Gly Gly Gln Lys Arg
        55              60                      65
Pro Leu Glu Asp Gly Asp Gln Pro Asp Ala Lys Lys Val
             70                  75
Ala Pro Gln Asn Asp Ser Phe Gly Thr Gln Leu Pro Pro
 80              85                          90
Met His Gln Gln Gln Ser Arg Ser Val Met Thr Glu Glu
         95                  100
Tyr Lys Val Pro Asp Gly Met Val Gly Phe Ile Ile Gly
105              110                 115
Arg Gly Gly Glu Gln Ile Ser Arg Ile Gln Gln Glu Ser
    120                 125                     130
Gly Cys Lys Ile Gln Ile Ala Pro Asp Ser Gly Gly Leu
             135                 140
Pro Glu Arg Ser Cys Xaa Leu Thr Gly Thr Pro Glu Ser
145                 150                     155
Val Gln Ser Ala Lys Arg Leu Leu Asp Gln Ile Val Glu
        160                 165
Lys Gly Arg Pro Ala Pro Gly Phe His His Gly Asp Gly
170             175                 180
Pro Gly Asn Ala Val Gln Glu Ile Met Ile Pro Ala Ser
        185                 190                 195
Lys Ala Gly Leu Val Ile Gly Lys Gly Gly Glu Thr Ile
                200                 205
Lys Gln Leu Gln Glu Arg Ala Gly Val Lys Met Val Met
    210                 215                 220
Ile Gln Asp Gly Pro Gln Asn Thr Gly Ala Asp Lys Pro
            225                 230
Leu Arg Ile Thr Gly Asp Pro Tyr Lys Val Gln Gln Ala
235                 240                 245
Lys Glu Met Val Leu Glu Leu Ile Arg Asp Gln Gly Gly
        250                 255                 260
Phe Arg Glu Val Arg Asn Glu Tyr Gly Ser Arg Ile Gly
                265                 270
```

```
Gly  Asn  Glu  Gly  Ile  Asp  Val  Pro  Ile  Pro  Arg  Phe  Ala
     275                 280                 285

Val  Gly  Ile  Val  Ile  Gly  Arg  Asn  Gly  Glu  Met  Ile  Lys
               290                 295

Lys  Ile  Gln  Asn  Asp  Ala  Gly  Val  Arg  Ile  Gln  Phe  Lys
300                      305                      310

Pro  Asp  Asp  Gly  Thr  Thr  Pro  Glu  Arg  Ile  Ala  Gln  Ile
          315                 320                      325

Thr  Gly  Pro  Pro  Asp  Arg  Cys  Gln  His  Ala  Ala  Glu  Ile
                    330                 335

Ile  Thr  Asp  Leu  Leu  Arg  Ser  Val  Gln  Ala  Gly  Asn  Pro
     340                 345                      350

Gly  Gly  Pro  Gly  Pro  Gly  Gly  Arg  Gly  Arg  Gly  Arg  Gly
               355                      360

Gln  Gly  Asn  Trp  Asn  Met  Gly  Pro  Pro  Gly  Gly  Leu  Gln
365                      370                      375

Glu  Phe  Asn  Phe  Ile  Val  Pro  Thr  Gly  Lys  Thr  Gly  Leu
          380                      385                      390

Ile  Ile  Gly  Lys  Gly  Gly  Glu  Thr  Ile  Lys  Ser  Ile  Ser
               395                      400

Gln  Gln  Ser  Gly  Ala  Arg  Ile  Glu  Leu  Gln  Arg  Asn  Pro
     405                      410                      415

Pro  Pro  Asn  Ala  Asp  Pro  Asn  Met  Lys  Leu  Phe  Thr  Ile
               420                      425

Arg  Gly  Thr  Pro  Gln  Gln  Ile  Asp  Tyr  Ala  Arg  Gln  Leu
430                      435                      440

Ile  Glu  Glu  Lys  Ile  Gly  Gly  Pro  Val  Asn  Pro  Leu  Gly
               445                      450                      455

Pro  Pro  Val  Pro  His  Gly  Pro  His  Gly  Val  Pro  Gly  Pro
                    460                      465

His  Gly  Pro  Pro  Gly  Pro  Pro  Gly  Pro  Gly  Thr  Pro  Met
     470                      475                      480

Gly  Pro  Tyr  Asn  Pro  Ala  Pro  Tyr  Asn  Pro  Gly  Pro  Pro
               485                      490

Gly  Pro  Ala  Pro  His  Gly  Pro  Pro  Ala  Pro  Tyr  Ala  Pro
495                      500                      505

Gln  Gly  Trp  Gly  Asn  Ala  Tyr  Pro  His  Trp  Gln  Gln  Gln
          510                      515                      520

Ala  Pro  Pro  Asp  Pro  Ala  Lys  Ala  Gly  Thr  Asp  Pro  Asn
                    525                      530

Ser  Ala  Ala  Trp  Ala  Ala  Tyr  Tyr  Ala  His  Tyr  Tyr  Gln
     535                 540                      545

Gln  Gln  Ala  Gln  Pro  Pro  Pro  Ala  Ala  Pro  Ala  Gly  Ala
               550                      555

Pro  Thr  Thr  Thr  Gln  Thr  Asn  Gly  Gln  Gly  Asp  Gln  Gln
560                      565                      570

Asn  Pro  Ala  Pro  Ala  Gly  Gln  Val  Asp  Tyr  Thr  Lys  Ala
          575                      580                      585

Trp  Glu  Glu  Tyr  Tyr  Lys  Lys  Met  Gly  Gln  Ala  Val  Pro
                    590                      595

Ala  Pro  Thr  Gly  Ala  Pro  Pro  Gly  Gly  Gln  Pro  Asp  Tyr
     600                      605                      610

Ser  Ala  Ala  Trp  Ala  Glu  His  Tyr  Arg  Gln  Gln  Ala  Ala
               615                      620
```

Tyr Tyr Ala Gln Thr Ser Pro Gln Gly Met Pro Gln His
625                 630                 635

Pro Pro Ala Pro Gln Gly Gln
            640

( 2 ) INFORMATION FOR SEQ ID NO:3:

( i ) SEQUENCE CHARACTERISTICS:
        ( A ) LENGTH: 27
        ( B ) TYPE: Nucleic acid
        ( C ) STRANDEDNESS: Single
        ( D ) TOPOLOGY: Unknown ( i i ) MOLECULE TYPE: cDNA ( i i i ) HYPOTHETICAL: No ( v i ) ORIGINAL SOURCE:
        ( A ) ORGANISM: Human ( i x ) FEATURE:
        ( A ) NAME/KEY:
        ( B ) LOCATION:
        ( C ) IDENTIFICATION METHOD:
        ( D ) OTHER INFORMATION: N at positions
            11, 14, and 23 is inosine (I);
            Y is either T or C; R is either
            A or G; N at position 25 is either
            I or T.

( i x ) SEQUENCE DESCRIPTION: SEQ ID NO: 3:

CAGAATTCGG NGGNAA Y GAR GGNANCG        27

( 2 ) INFORMATION FOR SEQ ID NO:4:

( i ) SEQUENCE CHARACTERISTICS:
        ( A ) LENGTH: 26
        ( B ) TYPE: Nucleic acid
        ( C ) STRANDEDNESS: Single
        ( D ) TOPOLOGY: Unknown ( i i ) MOLECULE TYPE: cDNA ( i i i ) HYPOTHETICAL: No ( v i ) ORIGINAL SOURCE:
        ( A ) ORGANISM: Human ( i x ) FEATURE:
        ( D ) OTHER INFORMATION: N is inosine;
            R is either A or G; Y is
            either C or T.

( x i ) SEQUENCE DESCRIPTION: SEQ ID NO: 4:

GAGTCGACRT CRTCRTCNGG Y TTRAA        26

( 2 ) INFORMATION FOR SEQ ID NO: 5:

( i ) SEQUENCE CHARACTERISTICS:
        ( A ) LENGTH: 1097
        ( B ) TYPE: Nucleic acid
        ( C ) STRANDEDNESS: Double
        ( D ) TOPOLOGY: Unknown ( i i ) MOLECULE TYPE: cDNA ( i i i ) HYPOTHETICAL: No ( i v ) ANTI-SENSE: YES ( v i ) ORIGINAL SOURCE:
        ( A ) ORGANISM: Human
        ( H ) CELL LINE: HL60

( x i ) SEQUENCE DESCRIPTION: SEQ ID NO: 5:

```
GGAATTCCGG ATA GAT GTC CCC ATT CCA AGA TTT GCT GTT      40
GGC ATT GTA ATA GGA AGA AAT GGA GAG ATG ATC AAA AAA     79
ATA CAA AAT GAT GCT GGT GTT CGC ATT CAG TTT AAG CCA    118
GAT GAT GGG ACA ACA CCC GAA AGG ATA GCA CAA ATA ACA    157
GGA CCT CCA GAC CGA TGT CAA CAT GCT GCA GAA ATT ATT    196
ACA GAC CTT CTT CGA AGT GTT CAG GCT GGT AAT CCT GGT    235
GGA CCT GGA CCT GGT GGT CGA GGA AGA GGT AGA GGT CAA    274
GGC AAC TGG AAC ATG GGA CCA CCT GGT GGA TTA CAG GAA    313
TTT AAT TTT ATT GTG CCA ACT GGG AAA ACT GGA TTA ATA    352
ATA GGA AAA GGA GGT GAA ACC ATA AAA AGC ATA AGC CAG    391
CAG TCT GGT GCA AGA ATA GAA CTT CAG AGA AAT CCT CCA    430
CCA AAT GCA GAT CCT AAT ATG AAG TTA TTT ACA ATT CGT    469
GGC ACT CCA CAA CAG ATA GAC TAT GCT CGG CAA CTC ATA    508
GAA GAA AAG ATT GGT GGC CCA GTA AAT CCT TTA GGG CCA    547
CCT GTA CCC CAT GGG CCC CAT GGT GTC CCA GGC CCC CAT    586
GGA CCT CCT GGG CCT CCA GGG CCT GGA ACT CCA ATG GGA    625
CCA TAC AAC CCT GCA CCT TAT AAT CCT GGA CCA CCA GGC    664
CCG GCT CCT CAT GGT CCT CCA GCC CCA TAT GCT CCC CAG    703
GGA TGG GGA AAG GAA ATT GAG CAG AAG GTA CAG GAG TAA    742
TAG CAATTCCCTG TAGCTCTCAA AGCAAATTTT GAGCTCATTT        785
TTCTTTTTCT GCAAGCTCAG CAGCAGAATG CCCAGAGTCT            825
TCCCTGGTAG ATGCAGGTTC CATAGCGACG TTCTCCTGCA            865
ATGCACGCTG GTATTCTGCA ATAGCAGGCC ATGTTTTCCT            905
TGAGCCTGGA TGCTTTGGAG CCAAGCTTTC GTCCCATGCA            945
AGGGAAACAA CCACTTCTGG GATGTCCGCT GCAATCTGCT            985
CCGGGGCTGC AGCAACCTCA TCAGCTCTCT TGCCTGGAGT           1025
GGCTCAGCCT GGCCTGCAGG GCCACCAGGA GAATGGCAGC           1065
AAGGATGGCG AGGGTCCTCA TGGCTGGAAT TC                   1097
```

( 2 ) INFORMATION FOR SEQ ID NO: 6:

( i ) SEQUENCE CHARACTERISTICS:
  ( A ) LENGTH: 243
  ( B ) TYPE: Amino Acid
  ( C ) STRANDEDNESS: Single
  ( D ) TOPOLOGY: Unknown ( i i ) MOLECULE TYPE: Peptide/Protein ( i i i ) HYPOTHETICAL: No ( v i ) ORIGINAL SOURCE:
  ( A ) ORGANISM: Human
  ( G ) CELL TYPE: HL60

( i x ) SEQUENCE DESCRIPTION: SEQ ID NO: 6:

```
Ile Asp Val Pro Ile Pro Arg Phe Ala Val
 1           5                        10
```

```
Gly  Ile  Val  Ile  Gly  Arg  Asn  Gly  Glu  Met  Ile  Lys  Lys
                     15                  20

Ile  Gln  Asn  Asp  Ala  Gly  Val  Arg  Ile  Gln  Phe  Lys  Pro
          25                  30                       35

Asp  Asp  Gly  Thr  Thr  Pro  Glu  Arg  Ile  Ala  Gln  Ile  Thr
                    40                   45

Gly  Pro  Pro  Asp  Arg  Cys  Gln  His  Ala  Ala  Glu  Ile  Ile
50                       55                       60

Thr  Asp  Leu  Leu  Arg  Ser  Val  Gln  Ala  Gly  Asn  Pro  Gly
               65                  70                       75

Gly  Pro  Gly  Pro  Gly  Gly  Arg  Gly  Arg  Gly  Arg  Gly  Gln
                    80                   85

Gly  Asn  Trp  Asn  Met  Gly  Pro  Pro  Gly  Gly  Leu  Gln  Glu
     90                       95                       100

Phe  Asn  Phe  Ile  Val  Pro  Thr  Gly  Lys  Thr  Gly  Leu  Ile
               105                 110

Ile  Gly  Lys  Gly  Gly  Glu  Thr  Ile  Lys  Ser  Ile  Ser  Gln
115                 120                      125

Gln  Ser  Gly  Ala  Arg  Ile  Glu  Leu  Gln  Arg  Asn  Pro  Pro
          130                 135                       140

Pro  Asn  Ala  Asp  Pro  Asn  Met  Lys  Leu  Phe  Thr  Ile  Arg
                    145                      150

Gly  Thr  Pro  Gln  Gln  Ile  Asp  Tyr  Ala  Arg  Gln  Leu  Ile
     155                      160                       165

Glu  Glu  Lys  Ile  Gly  Gly  Pro  Val  Asn  Pro  Leu  Gly  Pro
               170                      175

Pro  Val  Pro  His  Gly  Pro  His  Gly  Val  Pro  Gly  Pro  His
180                      185                 190

Gly  Pro  Pro  Gly  Pro  Pro  Gly  Pro  Gly  Thr  Pro  Met  Gly
          195                 200                       205

Pro  Tyr  Asn  Pro  Ala  Pro  Tyr  Asn  Pro  Gly  Pro  Pro  Gly
                    210                      215

Pro  Ala  Pro  His  Gly  Pro  Pro  Ala  Pro  Tyr  Ala  Pro  Gln
     220                 225                            230

Gly  Trp  Gly  Lys  Glu  Ile  Glu  Gln  Lys  Val  Gln  Glu
               235                 240
```

( 2 ) INFORMATION FOR SEQ ID NO: 7:

( i ) SEQUENCE CHARACTERISTICS:
        ( A ) LENGTH: 1803
        ( B ) TYPE: Nucleic acid
        ( C ) STRANDEDNESS: Double
        ( D ) TOPOLOGY: Unknown ( i i ) MOLECULE TYPE: cDNA ( i i i ) HYPOTHETICAL: No ( i v ) ANTI-SENSE: YES ( v i ) ORIGINAL SOURCE:
        ( A ) ORGANISM: Human
        ( H ) CELL LINE: HL60

( x i ) SEQUENCE DESCRIPTION: SEQ ID NO: 7:

```
GAATTCCGGA CGACAGCGGC TCTG AGA GCC CGG CAG ATT GCA          42

GCA AAA ATT GGA GGT GAT GCA GGG ACA TCA CTG AAT TCA         81
```

```
AAT GAC TAT GGT TAT GGG GGA CAA AAA AGA CCT TTA GAA         120
GAT GGA GAT GGC TCT TGG ACA AGT CCG AGC AGT ACA ACA         159
CAC TGG GAG GGA ATG CCC TCT CCT TTT AAA GAT CAA CCA         198
GAT GCT AAG AAA GTT GCT CCT CAA AAT GAC TCT TTT GGA         237
ACA CAG TTA CCA CCG ATG CAT CAG CAG CAA AGA TCT GTA         276
ATG ACA GAA GAA TAC AAA GTT CCA GAT GGA ATG GTT GGA         315
TTC ATA ATT GGC AGA GGA GGT GAA CAG ATC TCA CGC ATA         354
CAA CAG GAA TCT GGA TGC AAA ATA CAG ATA GCT CCT GAC         393
AGT GGT GGC CTT CCA GAA AGG TCC TGT ATG TTA ACT GGA         432
ACA CCT GAA TCT GTC CAG TCA GCA AAA CGG TTA CTG GAC         471
CAG ATT GTT GAA AAA GGA AGA CCA GCT CCT GGC TTC CAT         510
CAT GGC GAT GGA CCG GGA AAT GCA GTT CAA GAA ATC ATG         549
ATT CCA GCT AGC AAG GCA GGA TTA GTC ATT GGA AAA GGG         588
GGA GAA ACT ATT AAA CAG CTT CAG GAA CGG GCT GGA GTT         627
AAA ATG GTT ATG ATT CAA GAC GGG CCG CAG AAC ACT GGT         666
GCT GAC AAA CCT CTT AGG ATT ACA GGA GAC CCA TAT AAA         705
GTT CAA CAA GCC AAG GAA ATG GTG TTA GAG TTA ATT CGT         744
GAT CAA GGC GGT TTC AGA GAA GTT CGG AAT GAG TAT GGG         783
TCA AGA ATA GGA GGA AAT GAA GGG ATA GAT GTC CCC ATT         822
CCA AGA TTT GCT GTT GGC ATT GTA ATA GGA AGA AAT GGA         861
GAG ATG ATC AAA AAA ATA CAA AAT GAT GCT GGT GTT CGC         900
ATT CAG TTT AAG CCA GAT GAT GGG ACA ACA CCC GAA AGG         939
ATA GCA CAA ATA ACA GGA CCT CCA GAC CGA TGT CAA CAT         978
GCT GCA GAA ATT ATT ACA GAC CTT CTT CGA AGT GTT CAG        1017
GCT GGT AAT CCT GGT GGA CCT GGA CCT GGT GGT CGA GGA        1056
AGA GGT AGA GGT CAA GGC AAC TGG AAC ATG GGA CCA CCT        1095
GGT GGA TTA CAG GAA TTT AAT TTT ATT GTG CCA ACT GGG        1134
AAA ACT GGA TTA ATA ATA GGA AAA GGA GGT GAA ACC ATA        1173
AAA AGC ATA AGC CAG CAG TCT GGT GCA AGA ATA GAA CTT        1212
CAG AGA AAT CCT CCA CCA AAT GCA GAT CCT AAT ATG AAG        1251
TTA TTT ACA ATT CGT GGC ACT CCA CAA CAG ATA GAC TAT        1290
GCT CGG CAA CTC ATA GAA GAA AAG ATT GGT GGC CCA GTA        1329
AAT CCT TTA GGG CCA CCT GTA CCC CAT GGG CCC CAT GGT        1368
GTC CCA GGC CCC CAT GGA CCT CCT GGG CCT CCA GGG CCT        1407
GGA ACT CCA ATG GGA CCA TAC AAC CCT GCA CCT TAT AAT        1446
CCT GGA CCA CCA GGC CCG GCT CCT CAT GGT CCT CCA GCC        1485
CCA TAT GCT CCC CAG GGA TGG GGA AAT GCA TAT CCA CAC        1524
TGG CAG CAG CAG GCT CCT CCT GAT CCA GCT AAG GCA GGA        1563
ACG GAT CCA AAT TCA GCA GCT TGG GCT GCT TAT TAC GCT        1602
CAC TAT TAT CAA CAG CAA GCA CAG CCA CCA CCA GCA GCC        1641
```

|  |  |  |  |  |  |  |  |  |  |  |  |  |
|---|---|---|---|---|---|---|---|---|---|---|---|---|
| CCT | GCA | GGT | GCA | CCA | ACT | ACA | ACT | CAA | ACT | AAT | GGA | CAA | 1680 |
| GGA | GAT | CAG | CAG | AAT | CCA | GCC | CCA | GCT | GGA | CAG | GTT | GAT | 1719 |
| TAT | ACC | AAG | GCT | TGG | GAA | GAG | TAC | TAC | AAG | AAA | ATG | GGG | 1758 |
| CCA | ATA | ATA | AGA | AGT | GGA | CAA | TAC | AGT | ATT | TGC | TTC |  | 1794 |
| AGGAATTCC |  |  |  |  |  |  |  |  |  |  |  |  | 1803 |

( 2 ) INFORMATION FOR SEQ ID NO: 8:

( i ) SEQUENCE CHARACTERISTICS:
        ( A ) LENGTH: 590
        ( B ) TYPE: Amino Acid
        ( C ) STRANDEDNESS: Single
        ( D ) TOPOLOGY: Unknown ( i i ) MOLECULE TYPE: Peptide/Protein ( i i i ) HYPOTHETICAL: No ( v i ) ORIGINAL SOURCE:
        ( A ) ORGANISM: Human
        ( H ) CELL LINE: HL60

( x i ) SEQUENCE DESCRIPTION: SEQ ID NO: 8:

```
                              Arg  Ala  Arg  Gln  Ile  Ala
                               1                    5

Ala  Lys  Ile  Gly  Gly  Asp  Ala  Gly  Thr  Ser  Leu  Asn  Ser
               10                  15

Asn  Asp  Tyr  Gly  Tyr  Gly  Gly  Gln  Lys  Arg  Pro  Leu  Glu
 20                       25                  30

Asp  Gly  Asp  Gly  Ser  Trp  Thr  Ser  Pro  Ser  Ser  Thr  Thr
          35                       40                        45

His  Trp  Glu  Gly  Met  Pro  Ser  Pro  Phe  Lys  Asp  Gln  Pro
                    50                       55

Asp  Ala  Lys  Lys  Val  Ala  Pro  Gln  Asn  Asp  Ser  Phe  Gly
          60                  65                       70

Thr  Gln  Leu  Pro  Pro  Met  His  Gln  Gln  Arg  Ser  Val
               75                  80

Met  Thr  Glu  Glu  Tyr  Lys  Val  Pro  Asp  Gly  Met  Val  Gly
 85                       90                       95

Phe  Ile  Ile  Gly  Arg  Gly  Gly  Glu  Gln  Ile  Ser  Arg  Ile
               100                 105                      110

Gln  Gln  Glu  Ser  Gly  Cys  Lys  Ile  Gln  Ile  Ala  Pro  Asp
                    115                 120

Ser  Gly  Gly  Leu  Pro  Glu  Arg  Ser  Cys  Met  Leu  Thr  Gly
      125                      130                 135

Thr  Pro  Glu  Ser  Val  Gln  Ser  Ala  Lys  Arg  Leu  Leu  Asp
                140                      145

Gln  Ile  Val  Glu  Lys  Gly  Arg  Pro  Ala  Pro  Gly  Phe  His
 150                 155                      160

His  Gly  Asp  Gly  Pro  Gly  Asn  Ala  Val  Gln  Glu  Ile  Met
           165                      170                 175

Ile  Pro  Ala  Ser  Lys  Ala  Gly  Leu  Val  Ile  Gly  Lys  Gly
                    180                      185

Gly  Glu  Thr  Ile  Lys  Gln  Leu  Gln  Glu  Arg  Ala  Gly  Val
      190                      195                 200

Lys  Met  Val  Met  Ile  Gln  Asp  Gly  Pro  Gln  Asn  Thr  Gly
                205                      210
```

| | | | | | | | | | | | |
|---|---|---|---|---|---|---|---|---|---|---|---|
| Ala | Asp | Lys | Pro | Leu | Arg | Ile | Thr | Gly | Asp | Pro | Tyr | Lys |
| 215 | | | | 220 | | | | | 225 | | |

Val Gln Gln Ala Lys Glu Met Val Leu Glu Leu Ile Arg
230 235 240

Asp Gln Gly Gly Phe Arg Glu Val Arg Asn Glu Tyr Gly
245 250

Ser Arg Ile Gly Gly Asn Glu Gly Ile Asp Val Pro Ile
255 260 265

Pro Arg Phe Ala Val Gly Ile Val Ile Gly Arg Asn Gly
270 275

Glu Met Ile Lys Lys Ile Gln Asn Asp Ala Gly Val Arg
280 285 290

Ile Gln Phe Lys Pro Asp Asp Gly Thr Thr Pro Glu Arg
295 300 305

Ile Ala Gln Ile Thr Gly Pro Pro Asp Arg Cys Gln His
310 315

Ala Ala Glu Ile Ile Thr Asp Leu Leu Arg Ser Val Gln
320 325 330

Ala Gly Asn Pro Gly Gly Pro Gly Pro Gly Gly Arg Gly
335 340

Arg Gly Arg Gly Gln Gly Asn Trp Asn Met Gly Pro Pro
345 350 355

Gly Gly Leu Gln Glu Phe Asn Phe Ile Val Pro Thr Gly
360 365 370

Lys Thr Gly Leu Ile Ile Gly Lys Gly Gly Glu Thr Ile
375 380

Lys Ser Ile Ser Gln Gln Ser Gly Ala Arg Ile Glu Leu
385 390 395

Gln Arg Asn Pro Pro Asn Ala Asp Pro Asn Met Lys
400 405

Leu Phe Thr Ile Arg Gly Thr Pro Gln Gln Ile Asp Tyr
410 415 420

Ala Arg Gln Leu Ile Glu Glu Lys Ile Gly Gly Pro Val
425 430 435

Asn Pro Leu Gly Pro Pro Val Pro His Gly Pro His Gly
440 445

Val Pro Gly Pro His Gly Pro Gly Pro Pro Gly Pro
450 455 460

Gly Thr Pro Met Gly Pro Tyr Asn Pro Ala Pro Tyr Asn
465 470

Pro Gly Pro Pro Gly Pro Ala Pro His Gly Pro Pro Ala
475 480 485

Pro Tyr Ala Pro Gln Gly Trp Gly Asn Ala Tyr Pro His
490 495 500

Trp Gln Gln Gln Ala Pro Pro Asp Pro Ala Lys Ala Gly
505 510

Thr Asp Pro Asn Ser Ala Ala Trp Ala Ala Tyr Tyr Ala
515 520 525

His Tyr Tyr Gln Gln Gln Ala Gln Pro Pro Ala Ala
530 535

Pro Ala Gly Ala Pro Thr Thr Thr Gln Thr Asn Gly Gln
540 545 550

Gly Asp Gln Gln Asn Pro Ala Pro Ala Gly Gln Val Asp
555 560 565

Tyr Thr Lys Ala Trp Glu Glu Tyr Tyr Lys Lys Met Gly
                    570                 575

Pro Ile Ile Arg Ser Gly Gln Tyr Ser Ile Cys Phe
    580                 585                 590

( 2 ) INFORMATION FOR SEQ ID NO: 9:

( i ) SEQUENCE CHARACTERISTICS:
        ( A ) LENGTH: 2381
        ( B ) TYPE: Nucleic acid
        ( C ) STRANDEDNESS: Double
        ( D ) TOPOLOGY: Unknown ( i i ) MOLECULE TYPE: cDNA ( i i i ) HYPOTHETICAL: No ( i v ) ANTI-SENSE: YES ( v i ) ORIGINAL SOURCE:
        ( A ) ORGANISM: Human
        ( H ) CELL LINE: HL60

( i x ) FEATURE:
        ( D ) OTHER INFORMATION: 470 bp variable
        region where R is A or G.

( x i ) SEQUENCE DESCRIPTION: SEQ ID NO: 9:

| | | | | | | | | | | | | |
|---|---|---|---|---|---|---|---|---|---|---|---|---|
| GCGGCAGCGG | CTCTTATAGT | GCAACC | ATG | GCA | GAC | TAT | TCA | ACA | | | | 44 |
| GTG | CCT | CCC | CCC | TCT | TCT | GGC | TCA | GCT | GGT | GGC | GGT | 83 |
| GGC | GGC | GGT | GGT | GGT | GGA | GGA | GTT | AAC | GAC | GCT | TTC | AAA | 122 |
| GAT | GCA | CTG | CAG | AGA | GCC | CGG | CAG | ATT | GCA | GCA | AAA | ATT | 161 |
| GGA | GGT | GAT | GCA | GGG | ACA | TCA | CTG | AAT | TCA | AAT | GAC | TAT | 200 |
| GGT | TAT | GGG | GGA | CAA | AAA | AGA | CCT | TTA | GAA | GAT | GGA | GAT | 239 |
| CAA | CCA | GAT | GCT | AAG | AAA | GTT | GCT | CCT | CAA | AAT | GAC | TCT | 278 |
| TTT | GGA | ACA | CAG | TTA | CCA | CCG | ATG | CAT | CAG | CAG | CAA | | 314 |
| AGA | TCT | GTA | ATG | ACA | GAA | GAA | TAC | AAA | GTT | CCA | GAT | GGA | 353 |
| ATG | GTT | GGA | TTC | ATA | ATT | GGC | AGA | GGA | GGT | GAA | CAG | ATC | 392 |
| TCA | CGC | ATA | CAA | CAG | GAA | TCT | GGA | TGC | AAA | ATA | CAG | ATA | 431 |
| GCT | CCT | GAC | AGT | GGT | GGC | CTT | CCA | GAA | AGG | TCC | TGT | ATR | 470 |
| TTA | ACT | GGA | ACA | CCT | GAA | TCT | GTC | CAG | TCA | GCA | AAA | CGG | 509 |
| TTA | CTG | GAC | CAG | ATT | GTT | GAA | AAA | GGA | AGA | CCA | GCT | CCT | 548 |
| GGC | TTC | CAT | CAT | GGC | GAT | GGA | CCG | GGA | AAT | GCA | GTT | CAA | 587 |
| GAA | ATC | ATG | ATT | CCA | GCT | AGC | AAG | GCA | GGA | TTA | GTC | ATT | 626 |
| GGA | AAA | GGG | GGA | GAA | ACT | ATT | AAA | CAG | CTT | CAG | GAA | CGG | 665 |
| GCT | GGA | GTT | AAA | ATG | GTT | ATG | ATT | CAA | GAC | GGG | CCG | CAG | 704 |
| AAC | ACT | GGT | GCT | GAC | AAA | CCT | CTT | AGG | ATT | ACA | GGA | GAC | 743 |
| CCA | TAT | AAA | GTT | CAA | CAA | GCC | AAG | GAA | ATG | GTG | TTA | GAG | 782 |
| TTA | ATT | CGT | GAT | CAA | GGC | GGT | TTC | AGA | GAA | GTT | CGG | AAT | 821 |
| GAG | TAT | GGG | TCA | AGA | ATA | GGA | GGA | AAT | GAA | GGG | ATA | GAT | 860 |
| GTC | CCC | ATT | CCA | AGA | TTT | GCT | GTT | GGC | ATT | GTA | ATA | GGA | 899 |
| AGA | AAT | GGA | GAG | ATG | ATC | AAA | AAA | ATA | CAA | AAT | GAT | GCT | 938 |

```
GGT GTT CGC ATT CAG TTT AAG CCA GAT GAT GGG ACA ACA      977
CCC GAA AGG ATA GCA CAA ATA ACA GGA CCT CCA GAC CGA     1016
TGT CAA CAT GCT GCA GAA ATT ATT ACA GAC CTT CTT CGA     1055
AGT GTT CAG GCT GGT AAT CCT GGT GGA CCT GGA CCT GGT     1094
GGT CGA GGA AGA GGT AGA GGT CAA GGC AAC TGG AAC ATG     1133
GGA CCA CCT GGT GGA TTA CAG GAA TTT AAT TTT ATT GTG     1172
CCA ACT GGG AAA ACT GGA TTA ATA ATA GGA AAA GGA GGT     1211
GAA ACC ATA AAA AGC ATA AGC CAG CAG TCT GGT GCA AGA     1250
ATA GAA CTT CAG AGA AAT CCT CCA CCA AAT GCA GAT CCT     1289
AAT ATG AAG TTA TTT ACA ATT CGT GGC ACT CCA CAA CAG     1328
ATA GAC TAT GCT CGG CAA CTC ATA GAA GAA AAG ATT GGT     1367
GGC CCA GTA AAT CCT TTA GGG CCA CCT GTA CCC CAT GGG     1406
CCC CAT GGT GTC CCA GGC CCC CAT GGA CCT CCT GGG CCT     1445
CCA GGG CCT GGA ACT CCA ATG GGA CCA TAC AAC CCT GCA     1484
CCT TAT AAT CCT GGA CCA CCA GGC CCG GCT CCT CAT GGT     1523
CCT CCA GCC CCA TAT GCT CCC CAG GGA TGG GGA AAT GCA     1562
TAT CCA CAC TGG CAG CAG CAG GCT CCT CCT GAT CCA GCT     1601
AAG GCA GGA ACG GAT CCA AAT TCA GCA GCT TGG GCT GCT     1640
TAT TAC GCT CAC TAT TAT CAA CAG CAA GCA CAG CCA CCA     1679
CCA GCA GCC CCT GCA GGT GCA CCA ACT ACA ACT CAA ACT     1718
AAT GGA CAA GGA GAT CAG CAG AAT CCA GCC CCA GCT GGA     1757
CAG GTT GAT TAT ACC AAG GCT TGG GAA GAG TAC TAC AAG     1796
AAA ATG GGT CAG GCA GTT CCT GCT CCG ACT GGG GCT CCT     1835
CCA GGT GGT CAG CCA GAT TAT AGT GCA GCC TGG GCT GAG     1874
CAT TAT AGA CAA CAA GCA GCC TAT TAT GCC CAG ACA AGT     1913
CCC CAG GGA ATG CCA CAG CAT CCT CCA GCA CCT CAG GGC     1952
CAA TAA TAA GAAGTGGACA ATACAGTATT TGCTTCATTG            1991
TGTGGGGGAA AAAAACCTTT GTTAAATATA TGGATGCAGA             2031
CGACTTGATG AAGATCTTAA TTTTGTTTTT GGTTTAAAAT             2071
AGTGTTTCCT TTTTTTTTTT TTTTTTTTTG AAAATGTACA             2111
AAATATCTAT CACTACTGAT AGGAGGTTAA TATTTCTGTG             2151
TAGAAATGAA AATTGGTTTG TTTTAGTAT  TTAGTGTAGA             2191
TGTACACATT CCAGCAAATG TATTTGCAAT TATGTGGTTG             2231
ATGCTTTGTG ATATAAATGT ACTTTTTCAA TGTATACTTT             2271
CACTTTCCAA ATGCCTGTTT TGTGCTTTAC AATAAATGAT             2311
ATGAAACCTC AAAAAAAAAA AAAAAAAAAA AAAAAAAAAA             2351
AAAAAAAAAA AAAAAAAAAA AAAAAAAAA                         2381
```

( 2 ) INFORMATION FOR SEQ ID NO: 10:

( i ) SEQUENCE CHARACTERISTICS:
  ( A ) LENGTH: 643
  ( B ) TYPE: Amino Acid ( C ) STRANDEDNESS: Single
( D ) TOPOLOGY: Unknown ( i i ) MOLECULE TYPE: Peptide/Protein ( i i i ) HYPOTHETICAL: No ( v i ) ORIGINAL SOURCE:
    ( A ) ORGANISM: Human
    ( H ) CELL LINE: HL60

( i x ) FEATURE:
    ( D ) OTHER INFORMATION:
        Amino Acid 148 (Xaa) is Met or Ile ( x i ) SEQUENCE DESCRIPTION: SEQ ID NO: 10:

```
Met Ala Asp Tyr Ser Thr Val Pro Pro Pro Ser Ser Gly
 1               5                  10

Ser Ala Gly Gly Gly Gly Gly Gly Gly Gly Gly Gly Gly
        15                  20                  25

Val Asn Asp Ala Phe Lys Asp Ala Leu Gln Arg Ala Arg
                30                  35

Gln Ile Ala Ala Lys Ile Gly Gly Asp Ala Gly Thr Ser
 40                  45                  50

Leu Asn Ser Asn Asp Tyr Gly Tyr Gly Gly Gln Lys Arg
        55                  60                  65

Pro Leu Glu Asp Gly Asp Gln Pro Asp Ala Lys Lys Val
                70                  75

Ala Pro Gln Asn Asp Ser Phe Gly Thr Gln Leu Pro Pro
 80                  85                  90

Met His Gln Gln Gln Arg Ser Val Met Thr Glu Glu
        95                  100

Tyr Lys Val Pro Asp Gly Met Val Gly Phe Ile Ile Gly
    105                 110                 115

Arg Gly Gly Glu Gln Ile Ser Arg Ile Gln Gln Glu Ser
            120                 125

Gly Cys Lys Ile Gln Ile Ala Pro Asp Ser Gly Gly Leu
130                 135                 140

Pro Glu Arg Ser Cys Xaa Leu Thr Gly Thr Pro Glu Ser
        145                 150                 155

Val Gln Ser Ala Lys Arg Leu Leu Asp Gln Ile Val Glu
                160                 165

Lys Gly Arg Pro Ala Pro Gly Phe His His Gly Asp Gly
    170                 175                 180

Pro Gly Asn Ala Val Gln Glu Ile Met Ile Pro Ala Ser
            185                 190

Lys Ala Gly Leu Val Ile Gly Lys Gly Gly Glu Thr Ile
195                 200                 205

Lys Gln Leu Gln Glu Arg Ala Gly Val Lys Met Val Met
        210                 215                 220

Ile Gln Asp Gly Pro Gln Asn Thr Gly Ala Asp Lys Pro
                225                 230

Leu Arg Ile Thr Gly Asp Pro Tyr Lys Val Gln Gln Ala
    235                 240                 245

Lys Glu Met Val Leu Glu Leu Ile Arg Asp Gln Gly Gly
            250                 255

Phe Arg Glu Val Arg Asn Glu Tyr Gly Ser Arg Ile Gly
260                 265                 270
```

```
Gly  Asn  Glu  Gly  Ile  Asp  Val  Pro  Ile  Pro  Arg  Phe  Ala
          275                 280                           285

Val  Gly  Ile  Val  Ile  Gly  Arg  Asn  Gly  Glu  Met  Ile  Lys
               290                      295

Lys  Ile  Gln  Asn  Asp  Ala  Gly  Val  Arg  Ile  Gln  Phe  Lys
          300                 305                      310

Pro  Asp  Asp  Gly  Thr  Thr  Pro  Glu  Arg  Ile  Ala  Gln  Ile
               315                      320

Thr  Gly  Pro  Pro  Asp  Arg  Cys  Gln  His  Ala  Ala  Glu  Ile
325                      330                 335

Ile  Thr  Asp  Leu  Leu  Arg  Ser  Val  Gln  Ala  Gly  Asn  Pro
               340                 345                      350

Gly  Gly  Pro  Gly  Pro  Gly  Gly  Arg  Gly  Arg  Gly  Arg  Gly
                    355                      360

Gln  Gly  Asn  Trp  Asn  Met  Gly  Pro  Pro  Gly  Gly  Leu  Gln
          365                 370                      375

Glu  Phe  Asn  Phe  Ile  Val  Pro  Thr  Gly  Lys  Thr  Gly  Leu
               380                 385

Ile  Ile  Gly  Lys  Gly  Gly  Glu  Thr  Ile  Lys  Ser  Ile  Ser
390                      395                 400

Gln  Gln  Ser  Gly  Ala  Arg  Ile  Glu  Leu  Gln  Arg  Asn  Pro
          405                      410                      415

Pro  Pro  Asn  Ala  Asp  Pro  Asn  Met  Lys  Leu  Phe  Thr  Ile
               420                      425

Arg  Gly  Thr  Pro  Gln  Gln  Ile  Asp  Tyr  Ala  Arg  Gln  Leu
430                      435                      440

Ile  Glu  Glu  Lys  Ile  Gly  Gly  Pro  Val  Asn  Pro  Leu  Gly
               445                 450

Pro  Pro  Val  Pro  His  Gly  Pro  His  Gly  Val  Pro  Gly  Pro
455                 460                      465

His  Gly  Pro  Pro  Gly  Pro  Pro  Gly  Pro  Gly  Thr  Pro  Met
          470                 475                      480

Gly  Pro  Tyr  Asn  Pro  Ala  Pro  Tyr  Asn  Pro  Gly  Pro  Pro
               485                      490

Gly  Pro  Ala  Pro  His  Gly  Pro  Pro  Ala  Pro  Tyr  Ala  Pro
495                      500                      505

Gln  Gly  Trp  Gly  Asn  Ala  Tyr  Pro  His  Trp  Gln  Gln  Gln
               510                      515

Ala  Pro  Pro  Asp  Pro  Ala  Lys  Ala  Gly  Thr  Asp  Pro  Asn
520                      525                 530

Ser  Ala  Ala  Trp  Ala  Ala  Tyr  Tyr  Ala  His  Tyr  Tyr  Gln
               535                 540                      545

Gln  Gln  Ala  Gln  Pro  Pro  Ala  Ala  Pro  Ala  Gly  Ala
                    550                 555

Pro  Thr  Thr  Thr  Gln  Thr  Asn  Gly  Gln  Gly  Asp  Gln  Gln
     560                      565                      570

Asn  Pro  Ala  Pro  Ala  Gly  Gln  Val  Asp  Tyr  Thr  Lys  Ala
               575                 580

Trp  Glu  Glu  Tyr  Tyr  Lys  Lys  Met  Gly  Gln  Ala  Val  Pro
585                 590                      595

Ala  Pro  Thr  Gly  Ala  Pro  Pro  Gly  Gly  Gln  Pro  Asp  Tyr
          600                 605                      610

Ser  Ala  Ala  Trp  Ala  Glu  His  Tyr  Arg  Gln  Gln  Ala  Ala
                    615                      620
```

```
Tyr Tyr Ala Gln Thr Ser Pro Gln Gly Met Pro Gln His
625                 630                 635

Pro Pro Ala Pro Gln Gly Gln
            640
```

( 2 ) INFORMATION FOR SEQ ID NO: 11:

( i ) SEQUENCE CHARACTERISTICS:
        ( A ) LENGTH: 33
        ( B ) TYPE: Nucleic acid
        ( C ) STRANDEDNESS: Double
        ( D ) TOPOLOGY: Unknown ( i i ) MOLECULE TYPE: DNA ( v i ) ORIGINAL SOURCE:
        ( A ) ORGANISM: Human ( i x ) FEATURE:
        ( D ) OTHER INFORMATION: FUSE oligonucleotide ( x i ) SEQUENCE DESCRIPTION: SEQ ID NO: 11:

```
GATCACAAAA TAAAAATCC CGAGGGAATA TAG                          33
```

( 2 ) INFORMATION FOR SEQ ID NO: 12:

( i ) SEQUENCE CHARACTERISTICS:
        ( A ) LENGTH: 33
        ( B ) TYPE: Nucleic acid
        ( C ) STRANDEDNESS: Double
        ( D ) TOPOLOGY: Unknown ( i i ) MOLECULE TYPE: DNA ( i i i ) HYPOTHETICAL: YES ( i x ) FEATURE:
        ( D ) OTHER INFORMATION: Mut A ( x i ) SEQUENCE DESCRIPTION: SEQ ID NO: 12:

```
GATCACAACT ACGTGCTAGG ACGCCGAATA TAG                         33
```

( 2 ) INFORMATION FOR SEQ ID NO: 13:

( i ) SEQUENCE CHARACTERISTICS:
        ( A ) LENGTH: 39
        ( B ) TYPE: Nucleic acid
        ( C ) STRANDEDNESS: Double
        ( D ) TOPOLOGY: Unknown ( i i ) MOLECULE TYPE: DNA ( i i i ) HYPOTHETICAL: No ( i x ) FEATURE:
        ( D ) OTHER INFORMATION: cAMP response element ( x i ) SEQUENCE DESCRIPTION: SEQ ID NO: 13:

```
GATCTGACGT CATGACTGAC GTCATGACTG ACGTCATCA                   39
```

( 2 ) INFORMATION FOR SEQ ID NO: 14:

( i ) SEQUENCE CHARACTERISTICS:
        ( A ) LENGTH: 32
        ( B ) TYPE: Nucleic acid
        ( C ) STRANDEDNESS: Double
        ( D ) TOPOLOGY: Unknown ( i i ) MOLECULE TYPE: DNA ( i i i ) HYPOTHETICAL: NO ( i x ) FEATURE:
  ( D ) OTHER INFORMATION: CT element in c-myc
  5'- flanking region ("CTE")

( x i ) SEQUENCE DESCRIPTION: SEQ ID NO: 14:

AATTCTCCTC CCCACCTTCC CCACCCTCCC CA    32

( 2 ) INFORMATION FOR SEQ ID NO: 15:

( i ) SEQUENCE CHARACTERISTICS:
  ( A ) LENGTH: 33
  ( B ) TYPE: Nucleic acid
  ( C ) STRANDEDNESS: Double
  ( D ) TOPOLOGY: Unknown ( i i ) MOLECULE TYPE: DNA ( i i i ) HYPOTHETICAL: YES ( i x ) FEATURE:
  ( D ) OTHER INFORMATION: Mut B ( x i ) SEQUENCE DESCRIPTION: SEQ ID NO: 15:

GATCACAAAA TAAAAATGG ACGCCGAATA TAG    33

( 2 ) INFORMATION FOR SEQ ID NO: 16:

( i ) SEQUENCE CHARACTERISTICS:
  ( A ) LENGTH: 33
  ( B ) TYPE: Nucleic acid
  ( C ) STRANDEDNESS: Double
  ( D ) TOPOLOGY: Unknown ( i i ) MOLECULE TYPE: DNA ( i i i ) HYPOTHETICAL: YES ( i x ) FEATURE:
  ( D ) OTHER INFORMATION: Mut C ( x i ) SEQUENCE DESCRIPTION: SEQ ID NO: 16:

GATCACAACT ACGTGCTAGG CGAGGGAATA TAG    33

( 2 ) INFORMATION FOR SEQ ID NO: 17:

( i ) SEQUENCE CHARACTERISTICS:
  ( A ) LENGTH: 9
  ( B ) TYPE: Amino Acid
  ( C ) STRANDEDNESS: Single
  ( D ) TOPOLOGY: Unknown ( i i ) MOLECULE TYPE: Peptide/Protein ( i i i ) HYPOTHETICAL: No ( x i ) SEQUENCE DESCRIPTION: SEQ ID NO: 17:

Lys Glu Ile Glu Gln Lys Val Gln Glu
 1      5

( 2 ) INFORMATION FOR SEQ ID NO: 18:

( i ) SEQUENCE CHARACTERISTICS:
  ( A ) LENGTH: 12
  ( B ) TYPE: Nucleic acid
  ( C ) STRANDEDNESS: Double
  ( D ) TOPOLOGY: Unknown ( i i ) MOLECULE TYPE: DNA ( x i ) SEQUENCE DESCRIPTION: SEQ ID NO: 18:

TTAGTTAACT AA                                                                               12

( 2 ) INFORMATION FOR SEQ ID NO: 19:

( i ) SEQUENCE CHARACTERISTICS:
                ( A ) LENGTH: 6
                ( B ) TYPE: Amino Acid
                ( C ) STRANDEDNESS: Single
                ( D ) TOPOLOGY: Unknown ( i i ) MOLECULE TYPE: Peptide/Protein ( i x ) FEATURE:
                ( D ) OTHER INFORMATION: Mutant 2

( x i ) SEQUENCE DESCRIPTION: SEQ ID NO: 19:

Ile Gly Ser Arg Ile Arg
 1               5

( 2 ) INFORMATION FOR SEQ ID NO: 20:

( i ) SEQUENCE CHARACTERISTICS:
                ( A ) LENGTH: 4
                ( B ) TYPE: Amino Acid
                ( C ) STRANDEDNESS: Single
                ( D ) TOPOLOGY: Unknown ( i i ) MOLECULE TYPE: Peptide/Protein ( i x ) FEATURE:
                ( D ) OTHER INFORMATION: Mutant 3

( x i ) SEQUENCE DESCRIPTION: SEQ ID NO: 20:

Ile Arg Ile Arg
 1           5

( 2 ) INFORMATION FOR SEQ ID NO: 21:

( i ) SEQUENCE CHARACTERISTICS:
                ( A ) LENGTH: 5
                ( B ) TYPE: Amino Acid
                ( C ) STRANDEDNESS: Single
                ( D ) TOPOLOGY: Unknown ( i i ) MOLECULE TYPE: Peptide/Protein ( i x ) FEATURE:
                ( D ) OTHER INFORMATION: Mutant 4

( x i ) SEQUENCE DESCRIPTION: SEQ ID NO: 21:

Pro Arg Ile Arg Glu
 1               5

( 2 ) INFORMATION FOR SEQ ID NO: 22:

( i ) SEQUENCE CHARACTERISTICS:
                ( A ) LENGTH: 4
                ( B ) TYPE: Amino Acid
                ( C ) STRANDEDNESS: Single
                ( D ) TOPOLOGY: Unknown ( i i ) MOLECULE TYPE: Peptide/Protein ( i x ) FEATURE:
                ( D ) OTHER INFORMATION: Mutant 6

( x i ) SEQUENCE DESCRIPTION: SEQ ID NO: 22:

Gly Ile Pro Arg
 1           5

( 2 ) INFORMATION FOR SEQ ID NO: 23:

( i ) SEQUENCE CHARACTERISTICS:
        ( A ) LENGTH: 4
        ( B ) TYPE: Amino Acid
        ( C ) STRANDEDNESS: Single
        ( D ) TOPOLOGY: Unknown ( i i ) MOLECULE TYPE: Peptide/Protein ( i x ) FEATURE:
        ( D ) OTHER INFORMATION: Mutant 8

( x i ) SEQUENCE DESCRIPTION: SEQ ID NO: 23:

Arg Asp Pro Ala
1             5

( 2 ) INFORMATION FOR SEQ ID NO: 24:

( i ) SEQUENCE CHARACTERISTICS:
        ( A ) LENGTH: 4
        ( B ) TYPE: Amino Acid
        ( C ) STRANDEDNESS: Single
        ( D ) TOPOLOGY: Unknown ( i i ) MOLECULE TYPE: Peptide/Protein ( i x ) FEATURE:
        ( D ) OTHER INFORMATION: Mutant 9

( x i ) SEQUENCE DESCRIPTION: SEQ ID NO: 24:

Arg Gly Ser Gly
1             5

We claim:

1. A protein which binds specifically to an activator cis-element approximately 1500 basepairs 5' of the human c-myc gene promoter P1, said protein comprised of the amino acid sequence (SEQ ID NO: 2):

| Met 1 | Ala | Asp | Tyr | Ser 5 | Thr | Val | Pro | Pro | Pro 10 |
|---|---|---|---|---|---|---|---|---|---|
| Ser | Ser | Gly | Ser | Ala 15 | Gly | Gly | Gly | Gly | Gly 20 |
| Gly | Gly | Gly | Gly | Gly 25 | Gly | Val | Asn | Asp | Ala 30 |
| Phe | Lys | Asp | Ala | Leu 35 | Gln | Arg | Ala | Arg | Gln 40 |
| Ile | Ala | Ala | Lys | Ile 45 | Gly | Gly | Asp | Ala | Gly 50 |
| Thr | Ser | Leu | Asn | Ser 55 | Asn | Asp | Tyr | Gly | Tyr 60 |
| Gly | Gly | Gln | Lys | Arg 65 | Pro | Leu | Glu | Asp | Gly 70 |
| Asp | Gln | Pro | Asp | Ala 75 | Lys | Lys | Val | Ala | Pro 80 |
| Gln | Asn | Asp | Ser | Phe 85 | Gly | Thr | Gln | Leu | Pro 90 |
| Pro | Met | His | Gln | Gln 95 | Gln | Ser | Arg | Ser | Val 100 |
| Met | Thr | Glu | Glu | Tyr 105 | Lys | Val | Pro | Asp | Gly 110 |
| Met | Val | Gly | Phe | Ile 115 | Ile | Gly | Arg | Gly | Gly 120 |
| Glu | Gln | Ile | Ser | Arg 125 | Ile | Gln | Gln | Glu | Ser 130 |
| Gly | Cys | Lys | Ile | Gln 135 | Ile | Ala | Pro | Asp | Ser 140 |
| Gly | Gly | Leu | Pro | Glu 145 | Arg | Ser | Cys | Xaa | Leu 150 |
| Thr | Gly | Thr | Pro | Glu | Ser | Val | Gln | Ser | Ala |
| Lys | Arg | Leu | Leu | Asp 155 | Gln | Ile | Val | Glu | Lys 160 |
| Gly | Arg | Pro | Ala | Pro 165 | Gly | Phe | His | His | Gly 170 |
| Asp | Gly | Pro | Gly | Asn 175 | Ala | Val | Gln | Glu | Ile 180 |
| Met | Ile | Pro | Ala | Ser 185 | Lys | Ala | Gly | Leu | Val 190 |
| Ile | Gly | Lys | Gly | Gly 195 | Glu | Thr | Ile | Lys | Gln 200 |
| Leu | Gln | Glu | Arg | Ala 205 | Gly | Val | Lys | Met | Val 210 |
| Met | Ile | Gln | Asp | Gly 215 | Pro | Gln | Asn | Thr | Gly 220 |
| Ala | Asp | Lys | Pro | Leu 225 | Arg | Ile | Thr | Gly | Asp 230 |
| Pro | Tyr | Lys | Val | Gln 235 | Gln | Ala | Lys | Glu | Met 240 |
| Val | Leu | Glu | Leu | Ile 245 | Arg | Asp | Gln | Gly | Gly 250 |
| Phe | Arg | Glu | Val | Arg 255 | Asn | Glu | Tyr | Gly | Ser 260 |
| Arg | Ile | Gly | Gly | Asn 265 | Glu | Gly | Ile | Asp | Val 270 |
| Pro | Ile | Pro | Arg | Phe 275 | Ala | Val | Gly | Ile | Val 280 |
| Ile | Gly | Arg | Asn | Gly 285 | Glu | Met | Ile | Lys | Lys 290 |
| Ile | Gln | Asn | Asp | Ala 295 | Gly | Val | Arg | Ile | Gln 300 |
| Phe | Lys | Pro | Asp | Asp 305 | Gly | Thr | Thr | Pro | Glu 310 |
| Arg | Ile | Ala | Gln | Ile 315 | Thr | Gly | Pro | Pro | Asp 320 |
| Arg | Cys | Gln | His | Ala 325 | Ala | Glu | Ile | Ile | Thr 330 |
|  |  |  |  | 335 |  |  |  |  | 340 |

SEQ ID (continued from previous page)

| | | | | | | | | | |
|---|---|---|---|---|---|---|---|---|---|
| Asp | Leu | Leu | Arg | Ser 345 | Val | Gln | Ala | Gly | Asn 350 |
| Pro | Gly | Gly | Pro | Gly 355 | Pro | Gly | Gly | Arg | Gly 360 |
| Arg | Gly | Arg | Gly | Gln 365 | Gly | Asn | Trp | Asn | Met 370 |
| Gly | Pro | Pro | Gly | Gly 375 | Leu | Gln | Glu | Phe | Asn 380 |
| Phe | Ile | Val | Pro | Thr 385 | Gly | Lys | Thr | Gly | Leu 390 |
| Ile | Ile | Gly | Lys | Gly 395 | Gly | Glu | Thr | Ile | Lys 400 |
| Ser | Ile | Ser | Gln | Gln 405 | Ser | Gly | Ala | Arg | Ile 410 |
| Glu | Leu | Gln | Arg | Asn 415 | Pro | Pro | Pro | Asn | Ala 420 |
| Asp | Pro | Asn | Met | Lys 425 | Leu | Phe | Thr | Ile | Arg 430 |
| Gly | Thr | Pro | Gln | Gln 435 | Ile | Asp | Tyr | Ala | Arg 440 |
| Gln | Leu | Ile | Glu | Glu 445 | Lys | Ile | Gly | Gly | Pro 450 |
| Val | Asn | Pro | Leu | Gly 455 | Pro | Pro | Val | Pro | His 460 |
| Gly | Pro | His | Gly | Val 465 | Pro | Gly | Pro | His | Gly 470 |
| Pro | Pro | Gly | Pro | Pro 475 | Gly | Pro | Gly | Thr | Pro 480 |
| Met | Gly | Pro | Tyr | Asn 485 | Pro | Ala | Pro | Tyr | Asn 490 |
| Pro | Gly | Pro | Pro | Gly 495 | Pro | Ala | Pro | His | Gly 500 |
| Pro | Pro | Ala | Pro | Tyr 505 | Ala | Pro | Gln | Gly | Trp 510 |
| Gly | Asn | Ala | Tyr | Pro 515 | His | Trp | Gln | Gln | Gln 520 |
| Ala | Pro | Pro | Asp | Pro 525 | Ala | Lys | Ala | Gly | Thr 530 |
| Asp | Pro | Asn | Ser | Ala 535 | Ala | Trp | Ala | Ala | Tyr 540 |
| Tyr | Ala | His | Tyr | Tyr 545 | Gln | Gln | Gln | Ala | Gln 550 |
| Pro | Pro | Pro | Ala | Ala 555 | Pro | Ala | Gly | Ala | Pro 560 |
| Thr | Thr | Thr | Gln | Thr 565 | Asn | Gly | Gln | Gly | Asp 570 |
| Gln | Gln | Asn | Pro | Ala 575 | Pro | Ala | Gly | Gln | Val 580 |
| Asp | Tyr | Thr | Lys | Ala 585 | Trp | Glu | Glu | Tyr | Tyr 590 |
| Lys | Lys | Met | Gly | Gln 595 | Ala | Val | Pro | Ala | Pro 600 |
| Thr | Gly | Ala | Pro | Pro 605 | Gly | Gly | Gln | Pro | Asp 610 |
| Tyr | Ser | Ala | Ala | Trp 615 | Ala | Glu | His | Tyr | Arg 620 |
| Gln | Gln | Ala | Ala | Tyr 625 | Tyr | Ala | Gln | Thr | Ser 630 |
| Pro | Gln | Gly | Met | Pro 635 | Gln | His | Pro | Pro | Ala 640 |
| Pro | Gln | Gly | Gln | | | | | | | wherein Xaa is Ile or Met.

2. The protein of claim 1, wherein Xaa is Met.

3. The protein of claim 1, wherein Xaa is Ile.

4. A protein which binds specifically to an activator cis-element approximately 1500 basepairs 5' of the human c-myc gene promoter P1, said protein comprised of the amino acid sequence (SEQ ID NO: 10):

| | | | | | | | | | |
|---|---|---|---|---|---|---|---|---|---|
| Met 1 | Ala | Asp | Tyr | Ser 5 | Thr | Val | Pro | Pro | Pro 10 |
| Ser | Ser | Gly | Ser | Ala 15 | Gly | Gly | Gly | Gly | Gly 20 |
| Gly | Gly | Gly | Gly | Gly 25 | Gly | Val | Asn | Asp | Ala 30 |
| Phe | Lys | Asp | Ala | Leu 35 | Gln | Arg | Ala | Arg | Gln 40 |
| Ile | Ala | Ala | Lys | Ile 45 | Gly | Gly | Asp | Ala | Gly 50 |
| Thr | Ser | Leu | Asn | Ser 55 | Asn | Asp | Tyr | Gly | Tyr 60 |
| Gly | Gly | Gln | Lys | Arg 65 | Pro | Leu | Glu | Asp | Gly 70 |
| Asp | Gln | Pro | Asp | Ala 75 | Lys | Lys | Val | Ala | Pro 80 |
| Gln | Asn | Asp | Ser | Phe 85 | Gly | Thr | Gln | Leu | Pro 90 |
| Pro | Met | His | Gln | Gln 95 | Gln | Arg | Ser | Val | Met 100 |
| Thr | Glu | Glu | Tyr | Lys 105 | Val | Pro | Asp | Gly | Met 110 |
| Val | Gly | Phe | Ile | Ile 115 | Gly | Arg | Gly | Gly | Glu 120 |
| Gln | Ile | Ser | Arg | Ile 125 | Gln | Gln | Glu | Ser | Gly 130 |
| Cys | Lys | Ile | Gln | Ile 135 | Ala | Pro | Asp | Ser | Gly 140 |
| Gly | Leu | Pro | Glu | Arg 145 | Ser | Cys | Xaa | Leu | Thr 150 |
| Gly | Thr | Pro | Glu | Ser 155 | Val | Gln | Ser | Ala | Lys 160 |
| Arg | Leu | Leu | Asp | Gln 165 | Ile | Val | Glu | Lys | Gly 170 |
| Arg | Pro | Ala | Pro | Gly 175 | Phe | His | His | Gly | Asp 180 |
| Gly | Pro | Gly | Asn | Ala 185 | Val | Gln | Glu | Ile | Met 190 |
| Ile | Pro | Ala | Ser | Lys 195 | Ala | Gly | Leu | Val | Ile 200 |
| Gly | Lys | Gly | Gly | Glu 205 | Thr | Ile | Lys | Gln | Leu 210 |
| Gln | Glu | Arg | Ala | Gly 215 | Val | Lys | Met | Val | Met 220 |
| Ile | Gln | Asp | Gly | Pro 225 | Gln | Asn | Thr | Gly | Ala 230 |
| Asp | Lys | Pro | Leu | Arg 235 | Ile | Thr | Gly | Asp | Pro 240 |
| Tyr | Lys | Val | Gln | Gln 245 | Ala | Lys | Glu | Met | Val 250 |
| Leu | Glu | Leu | Ile | Arg 255 | Asp | Gln | Gly | Gly | Phe 260 |
| Arg | Glu | Val | Arg | Asn 265 | Glu | Tyr | Gly | Ser | Arg 270 |
| Ile | Gly | Gly | Asn | Glu 275 | Gly | Ile | Asp | Val | Pro 280 |
| Ile | Pro | Arg | Phe | Ala 285 | Val | Gly | Ile | Val | Ile 290 |
| Gly | Arg | Asn | Gly | Glu 295 | Met | Ile | Lys | Lys | Ile 300 |
| Gln | Asn | Asp | Ala | Gly 305 | Val | Arg | Ile | Gln | Phe 310 |
| Lys | Pro | Asp | Asp | Gly 315 | Thr | Thr | Pro | Glu | Arg 320 |
| Ile | Ala | Gln | Ile | Thr 325 | Gly | Pro | Pro | Asp | Arg 330 |
| Cys | Gln | His | Ala | Ala 335 | Glu | Ile | Ile | Thr | Asp 340 |
| Leu | Leu | Arg | Ser | Val 345 | Gln | Ala | Gly | Asn | Pro 350 |
| Gly | Gly | Pro | Gly | Pro 355 | Gly | Gly | Arg | Gly | Arg 360 |
| Gly | Arg | Gly | Gln | Gly 365 | Asn | Trp | Asn | Met | Gly 370 |
| Pro | Pro | Gly | Gly | Leu 375 | Gln | Glu | Phe | Asn | Phe 380 |
| Ile | Val | Pro | Thr | Gly 385 | Lys | Thr | Gly | Leu | Ile 390 |
| Ile | Gly | Lys | Gly | Gly 395 | Glu | Thr | Ile | Lys | Ser 400 |
| Ile | Ser | Gln | Gln | Ser 405 | Gly | Ala | Arg | Ile | Glu 410 |
| Leu | Gln | Arg | Asn | Pro 415 | Pro | Pro | Asn | Ala | Asp 420 |
| Pro | Asn | Met | Lys | Leu 425 | Phe | Thr | Ile | Arg | Gly 430 |

-continued

| Thr | Pro | Gln | Gln | Ile 435 | Asp | Tyr | Ala | Arg | Gln 440 |
|---|---|---|---|---|---|---|---|---|---|
| Leu | Ile | Glu | Glu | Lys 445 | Ile | Gly | Gly | Pro | Val 450 |
| Asn | Pro | Leu | Gly | Pro 455 | Pro | Val | Pro | His | Gly 460 |
| Pro | His | Gly | Val | Pro 465 | Gly | Pro | His | Gly | Pro 470 |
| Pro | Gly | Pro | Pro | Gly 475 | Pro | Gly | Thr | Pro | Met 480 |
| Gly | Pro | Tyr | Asn | Pro 485 | Ala | Pro | Tyr | Asn | Pro 490 |
| Gly | Pro | Pro | Gly | Pro 495 | Ala | Pro | His | Gly | Pro 500 |
| Pro | Ala | Pro | Tyr | Ala 505 | Pro | Gln | Gly | Trp | Gly 510 |
| Asn | Ala | Tyr | Pro | His 515 | Trp | Gln | Gln | Gln | Ala 520 |
| Pro | Pro | Asp | Pro | Ala | Lys | Ala | Gly | Thr | Asp |

-continued

| Lys | Met | Gly | Gln | Ala 595 | Val | Pro | Ala | Pro | Thr 600 |
|---|---|---|---|---|---|---|---|---|---|
| Gly | Ala | Pro | Pro | Gly 605 | Gly | Gln | Pro | Asp | Tyr 610 |
| Ser | Ala | Ala | Trp | Ala 615 | Glu | His | Tyr | Arg | Gln 620 |
| Gln | Ala | Ala | Tyr | Tyr 625 | Ala | Gln | Thr | Ser | Pro 630 |
| Gln | Gly | Met | Pro | Gln 635 | His | Pro | Pro | Ala | Pro 640 |
| Gln | Gly | Gln | | | | | | | | wherein Xaa is Ile or Met.

5. The protein of claim 4, wherein Xaa is Met.

6. The protein of claim 4, wherein Xaa is Ile.

7. A protein which binds specifically to an activator cis-element approximately 1500 basepairs 5' of the human c-myc gene promoter P1 comprised of the amino acid sequence (SEQ NO ID: 6):

| | | | Ile 1 | Asp | Val | Pro | Ile 5 | Pro | Arg | Phe | Ala | Val 10 |
|---|---|---|---|---|---|---|---|---|---|---|---|---|
| Gly | Ile | Val | Ile | Gly 15 | Arg | Asn | Gly | Glu | Met 20 | Ile | Lys | Lys |
| Ile | Gln 25 | Asn | Asp | Ala | Gly | Val 30 | Arg | Ile | Gln | Phe | Lys 35 | Pro |
| Asp | Asp | Gly | Thr 40 | Thr | Pro | Glu | Arg | Ile 45 | Ala | Gln | Ile | Thr |
| Gly 50 | Pro | Pro | Asp | Arg | Cys 55 | Gln | His | Ala | Ala | Glu 60 | Ile | Ile |
| Thr | Asp | Leu 65 | Leu | Arg | Ser | Val | Gln 70 | Ala | Gly | Asn | Pro | Gly 75 |
| Gly | Pro | Gly | Pro | Gly 80 | Gly | Arg | Gly | Arg 85 | Gly | Arg | Gly | Gln |
| Gly | Asn 90 | Trp | Asn | Met | Gly | Pro 95 | Pro | Gly | Gly | Leu | Gln 100 | Glu |
| Phe | Asn | Phe | Ile 105 | Val | Pro | Thr | Gly | Lys 110 | Thr | Gly | Leu | Ile |
| Ile 115 | Gly | Lys | Gly | Gly | Glu 120 | Thr | Ile | Lys | Ser | Ile 125 | Ser | Gln |
| Gln | Ser | Gly 130 | Ala | Arg | Ile | Glu | Leu 135 | Gln | Arg | Asn | Pro | Pro 140 |
| Pro | Asn | Ala | Asp | Pro 145 | Asn | Met | Lys | Leu | Phe 150 | Thr | Ile | Arg |
| Gly | Thr 155 | Pro | Gln | Gln | Ile | Asp 160 | Tyr | Ala | Arg | Gln | Leu 165 | Ile |
| Glu | Glu | Lys | Ile 170 | Gly | Gly | Pro | Val | Asn 175 | Pro | Leu | Gly | Pro |
| Pro 180 | Val | Pro | His | Gly | Pro 185 | His | Gly | Val | Pro | Gly 190 | Pro | His |
| Gly | Pro | Pro 195 | Gly | Pro | Pro | Gly | Pro 200 | Gly | Thr | Pro | Met | Gly 205 |
| Pro | Tyr | Asn | Pro | Ala 210 | Pro | Tyr | Asn | Pro | Gly 215 | Pro | Pro | Gly |
| Pro | Ala 220 | Pro | His | Gly | Pro | Pro 225 | Ala | Pro | Tyr | Ala 230 | Pro | Gln |
| Gly | Trp | Gly 235 | Lys | Glu | Ile | Glu | Gln | Lys 240 | Val | Gln | Glu. | |

-continued

| | | | | 525 | | | | | 530 |
|---|---|---|---|---|---|---|---|---|---|
| Pro | Asn | Ser | Ala | Ala 535 | Trp | Ala | Ala | Tyr | Tyr 540 |
| Ala | His | Tyr | Tyr | Gln 545 | Gln | Ala | Gln | Pro 550 | |
| Pro | Pro | Ala | Ala | Pro 555 | Ala | Gly | Ala | Pro | Thr 560 |
| Thr | Thr | Gln | Thr | Asn 565 | Gly | Gly | Gly | Asp | Gln 570 |
| Gln | Asn | Pro | Ala | Pro 575 | Ala | Gly | Gln | Val | Asp 580 |
| Tyr | Thr | Lys | Ala | Trp 585 | Glu | Glu | Tyr | Tyr | Lys 590 |

8. A protein which binds specifically to an activator cis-element approximately 1500 basepairs 5' of the human c-myc promoter P1 comprised of the amino acid sequence (SEQ ID NO: 8):

|    |    |    |    |    |    | Arg 1 | Ala | Arg | Gln | Ile 5 | Ala |
|----|----|----|----|----|----|-------|-----|-----|-----|-------|-----|
| Ala | Lys | Ile | Gly 10 | Gly | Asp | Ala | Gly | Thr 15 | Ser | Leu | Asn | Ser |
| Asn 20 | Asp | Tyr | Gly | Tyr | Gly 25 | Gly | Gln | Lys | Arg | Pro 30 | Leu | Glu |
| Asp | Gly | Asp 35 | Gly | Ser | Trp | Thr | Ser 40 | Pro | Ser | Ser | Thr | Thr 45 |
| His | Trp | Glu | Gly | Met 50 | Pro | Ser | Pro | Phe | Lys 55 | Asp | Gln | Pro |
| Asp | Ala 60 | Lys | Lys | Val | Ala | Pro 65 | Gln | Asn | Asp | Ser | Phe 70 | Gly |
| Thr | Gln | Leu | Pro 75 | Pro | Met | His | Gln | Gln 80 | Gln | Arg | Ser | Val |
| Met 85 | Thr | Glu | Glu | Tyr | Lys 90 | Val | Pro | Asp | Gly | Met 95 | Val | Gly |
| Phe | Ile | Ile 100 | Gly | Arg | Gly | Gly | Glu 105 | Gln | Ile | Ser | Arg | Ile 110 |
| Gln | Gln | Glu | Ser | Gly 115 | Cys | Lys | Ile | Gln | Ile 120 | Ala | Pro | Asp |
| Ser | Gly 125 | Gly | Leu | Pro | Glu | Arg 130 | Ser | Cys | Met | Leu | Thr 135 | Gly |
| Thr | Pro | Glu | Ser 140 | Val | Gln | Ser | Ala | Lys 145 | Arg | Leu | Leu | Asp |
| Gln 150 | Ile | Val | Glu | Lys | Gly 155 | Arg | Pro | Ala | Pro | Gly 160 | Phe | His |
| His | Gly 165 | Asp | Gly | Pro | Gly | Asn 170 | Ala | Val | Gln | Glu | Ile | Met 175 |
| Ile | Pro | Ala | Ser | Lys 180 | Ala | Gly | Leu | Val | Ile 185 | Gly | Lys | Gly |
| Gly | Glu 190 | Thr | Ile | Lys | Gln | Leu 195 | Gln | Glu | Arg | Ala | Gly 200 | Val |
| Lys | Met | Val | Met 205 | Ile | Gln | Asp | Gly | Pro 210 | Gln | Asn | Thr | Gly |
| Ala 215 | Asp | Lys | Pro | Leu | Arg 220 | Ile | Thr | Gly | Asp | Pro 225 | Tyr | Lys |
| Val | Gln | Gln | Ala 230 | Lys | Glu | Met | Val 235 | Leu | Glu | Leu | Ile | Arg 240 |
| Asp | Gln | Gly | Gly | Phe 245 | Arg | Glu | Val | Arg | Asn 250 | Glu | Tyr | Gly |
| Ser | Arg 255 | Ile | Gly | Gly | Asn | Glu 260 | Gly | Ile | Asp | Val | Pro 265 | Ile |
| Pro | Arg | Phe | Ala 270 | Val | Gly | Ile | Val | Ile 275 | Gly | Arg | Asn | Gly |
| Glu 280 | Met | Ile | Lys | Lys | Ile 285 | Gln | Asn | Asp | Ala | Gly 290 | Val | Arg |
| Ile | Gln | Phe | Lys 295 | Pro | Asp | Asp | Gly | Thr 300 | Thr | Pro | Glu | Arg 305 |
| Ile | Ala | Gln | Ile | Thr 310 | Gly | Pro | Pro | Asp | Arg 315 | Cys | Gln | His |
| Ala | Ala 320 | Glu | Ile | Ile | Thr | Asp 325 | Leu | Leu | Arg | Ser | Val 330 | Gln |
| Ala | Gly | Asn | Pro 335 | Gly | Gly | Pro | Gly | Pro 340 | Gly | Gly | Arg | Gly |
| Arg 345 | Gly | Arg | Gly | Gln | Gly 350 | Asn | Trp | Asn | Met | Gly 355 | Pro | Pro |
| Gly | Gly | Leu | Gln 360 | Glu | Phe | Asn | Phe 365 | Ile | Val | Pro | Thr | Gly 370 |
| Lys | Thr | Gly | Leu | Ile 375 | Ile | Gly | Lys | Gly | Glu 380 | Thr | Ile |
| Lys | Ser 385 | Ile | Ser | Gln | Gln | Ser 390 | Gly | Ala | Arg | Ile | Glu 395 | Leu |
| Gln | Arg | Asn | Pro 400 | Pro | Pro | Asn | Ala | Asp 405 | Pro | Asn | Met | Lys |
| Leu 410 | Phe | Thr | Ile | Arg | Gly 415 | Thr | Pro | Gln | Gln | Ile 420 | Asp | Tyr |
| Ala | Arg | Gln 425 | Leu | Ile | Glu | Glu | Lys 430 | Ile | Gly | Gly | Pro | Val 435 |
| Asn | Pro | Leu | Gly 440 | Pro | Pro | Val | Pro | His 445 | Gly | Pro | His | Gly |
| Val | Pro 450 | Gly | Pro | His | Gly | Pro 455 | Pro | Gly | Pro | Pro | Gly 460 | Pro |
| Gly | Thr | Pro | Met 465 | Gly | Pro | Tyr | Asn | Pro 470 | Ala | Pro | Tyr | Asn |
| Pro 475 | Gly | Pro | Pro | Gly | Pro 480 | Ala | Pro | His | Gly | Pro 485 | Pro | Ala |
| Pro | Tyr | Ala 490 | Pro | Gln | Gly | Trp | Gly 495 | Asn | Ala | Tyr | Pro | His 500 |
| Trp | Gln | Gln | Gln | Ala 505 | Pro | Pro | Asp | Pro | Ala 510 | Lys | Ala | Gly |

-continued

| Thr | Asp 515 | Pro | Asn | Ser | Ala | Ala 520 | Trp | Ala | Ala | Tyr | Tyr 525 | Ala |
| His | Tyr | Tyr | Gln 530 | Gln | Gln | Ala | Gln | Pro 535 | Pro | Pro | Ala | Ala |
| Pro 540 | Ala | Gly | Ala | Pro | Thr 545 | Thr | Thr | Gln | Thr | Asn 550 | Gly | Gln |
| Gly | Asp | Gln 555 | Gln | Asn | Pro | Ala | Pro 560 | Ala | Gly | Gln | Val | Asp 565 |
| Tyr | Thr | Lys | Ala | Trp 570 | Glu | Glu | Tyr | Tyr | Lys 575 | Lys | Met | Gly |
| Pro | Ile 580 | Ile | Arg | Ser | Gly | Gln 585 | Tyr | Ser | Ile | Cys | Phe 590. | | oe a fragment thereof.

9. A protein exhibiting a DNA binding motif, containing at least two repeating helix regions, each of said regions comprised of the following:
   (a) a region comprised of about 20% glycine, followed by
   (b) a short helix comprised of about 10–12 amino acids, followed by
   (c) a long amphipathic helix comprised of about 16–18 amino acids.

10. A protein of claim 9 which binds specifically to an activator cis-element approximately 1500 basepairs 5' of the human c-myc gene promoter P1.

11. A protein of claim 10 selected from the group consisting of SEQ ID NO: 2, SEQ ID NO: 6, SEQ ID NO: 8 and SEQ ID NO: 10.

12. A diagnostic kit for FUSE binding protein including at least one of the proteins shown in SEQ ID NO: 2, SEQ ID NO: 6, SEQ ID NO: 8, or SEQ ID NO: 10.

13. A fragment of the protein of claim 1 comprising at least one intact fuse binding protein repeat unit.

14. A fragment of the protein of claim 4 comprising at least one intact fuse binding protein repeat unit.

15. A fragment of the protein of claim 7 comprising at least one intact fuse binding protein repeat unit.

16. A fragment of the protein of claim 8 comprising at least one intact fuse binding protein repeat unit.

17. A fragment of the protein of claim 9 comprising at least one intact fuse binding protein repeat unit.

18. A diagnostic kit for FUSE binding protein including a fragment of at least one of the proteins shown in SEQ ID NO: 2, SEQ ID NO: 6, SEQ ID NO: 8, or SEQ ID NO: 10, which fragment comprises at least one intact fuse binding protein repeat unit.

19. A fragment of the protein of claim 1 comprising at least 30 amino acids.

20. A fragment of the protein of claim 4 comprising at least 30 amino acids.

21. A fragment of the protein of claim 7 comprising at least 30 amino acids.

22. A fragment of the protein of claim 8 comprising at least 30 amino acids.

23. A fragment of the protein of claim 9 comprising at least 30 amino acids.

24. A diagnostic kit for FUSE binding protein including a fragment of at least one of the proteins shown in SEQ ID NO: 2, SEQ ID NO: 6, SEQ ID NO: 8, or SEQ ID NO: 10, which fragment comprises at least 30 amino acids.

25. A fragment of the protein of claim 1 comprising at least 16 amino acids.

26. A fragment of the protein of claim 4 comprising at least 16 amino acids.

27. A fragment of the protein of claim 7 comprising at least 16 amino acids.

28. A fragment of the protein of claim 8 comprising at least 16 amino acids.

29. A fragment of the protein of claim 9 comprising at least 16 amino acids.

30. A diagnostic kit for FUSE binding protein including a fragment of at least one of the proteins shown in SEQ ID NO: 2, SEQ ID NO: 6, SEQ ID NO: 8, or SEQ ID NO: 10, which fragment comprises at least 16 amino acids.

* * * * *